United States Patent
McKinney et al.

(10) Patent No.: US 9,107,837 B2
(45) Date of Patent: *Aug. 18, 2015

(54) SUSTAINED RELEASE FORMULATION OF NALTREXONE

(71) Applicant: Orexigen Therapeutics, Inc., La Jolla, CA (US)

(72) Inventors: Anthony A. McKinney, San Diego, CA (US); Gary D. Tollefson, Indianapolis, IN (US); Richard Soltero, Holly Springs, NC (US); Thea Elise Dunzo, Durham, NC (US)

(73) Assignee: Orexigen Therapeutics, Inc., La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/555,475

(22) Filed: Nov. 26, 2014

(65) Prior Publication Data

US 2015/0080424 A1   Mar. 19, 2015

Related U.S. Application Data

(63) Continuation of application No. 11/757,773, filed on Jun. 4, 2007, now Pat. No. 8,916,195.

(60) Provisional application No. 60/811,251, filed on Jun. 5, 2006, provisional application No. 60/841,114, filed on Aug. 29, 2006.

(51) Int. Cl.
*A61K 9/20* (2006.01)
*A61K 31/12* (2006.01)
(Continued)

(52) U.S. Cl.
CPC .............. *A61K 9/2054* (2013.01); *A61K 9/2009* (2013.01); *A61K 9/209* (2013.01);
(Continued)

(58) Field of Classification Search
CPC . A61K 9/2054; A61K 31/485; A61K 9/2018; A61K 9/2009; A61K 9/2013; A61K 9/20131; A61K 31/12; A61K 9/209
USPC .................................. 514/282, 649; 424/468
See application file for complete search history.

(56) References Cited

U.S. PATENT DOCUMENTS 3,819,706 A    6/1974   Mehta
3,885,046 A    5/1975   Mehta
(Continued)

FOREIGN PATENT DOCUMENTS

CA    2317044    7/1999
EP    0 005 636  11/1979
(Continued)

OTHER PUBLICATIONS

Ackerman et al., 1998, Clinical characteristics of response to fluoxetine treatment of obsessive-compulsive disorder. Journal of Clinical Psychopharmacology, 18(3):185-192.
(Continued)

*Primary Examiner* — Ernst V Arnold
*Assistant Examiner* — Hong Yu
(74) *Attorney, Agent, or Firm* — Knobbe Martens Olson & Bear LLP

(57) ABSTRACT

A sustained-release oral dosage form of naltrexone or a pharmaceutically acceptable salt thereof is provided. The oral dosage form may be administered with another compound. Administration of the oral dosage form may reduce a side effect, which may be a side effect at least partially attributable to a weight-loss treatment. The oral dosage form may be administered to treat a weight-loss condition.

17 Claims, 20 Drawing Sheets

(51) Int. Cl.
*A61K 9/24* (2006.01)
*A61K 31/485* (2006.01)

(52) U.S. Cl.
CPC ............ *A61K 9/2013* (2013.01); *A61K 9/2018* (2013.01); *A61K 9/2027* (2013.01); *A61K 9/2031* (2013.01); *A61K 31/12* (2013.01); *A61K 31/485* (2013.01)

(56) References Cited

U.S. PATENT DOCUMENTS

| | | | |
|---|---|---|---|
| 3,942,641 | A | 3/1976 | Segre |
| 4,089,855 | A | 5/1978 | Chatterjie et al. |
| 4,172,896 | A | 10/1979 | Uno et al. |
| 4,218,433 | A | 8/1980 | Kooichi et al. |
| 4,295,567 | A | 10/1981 | Knudsen |
| 4,483,846 | A | 11/1984 | Koide et al. |
| 4,513,006 | A | 4/1985 | Maryanoff et al. |
| 4,673,679 | A | 6/1987 | Aungst et al. |
| 4,689,332 | A | 8/1987 | McLaughlin et al. |
| 4,828,836 | A | 5/1989 | Elger et al. |
| 4,831,031 | A | 5/1989 | Lowe et al. |
| 4,855,306 | A | 8/1989 | Markstein et al. |
| 4,895,845 | A | 1/1990 | Seed |
| 5,000,886 | A | 3/1991 | Lawter et al. |
| 5,028,612 | A | 7/1991 | Glover |
| 5,082,864 | A | 1/1992 | Van den Oetelaar et al. |
| 5,202,128 | A | 4/1993 | Morella et al. |
| 5,213,807 | A | 5/1993 | Chemburkar et al. |
| 5,213,808 | A | 5/1993 | Bar-Shalom et al. |
| 5,283,263 | A | 2/1994 | Norden |
| 5,312,925 | A | 5/1994 | Allen et al. |
| 5,358,970 | A | 10/1994 | Ruff et al. |
| 5,364,841 | A | 11/1994 | Cooper et al. |
| 5,403,595 | A | 4/1995 | Kitchell et al. |
| 5,426,112 | A | 6/1995 | Zagon et al. |
| 5,427,798 | A | 6/1995 | Ludwig et al. |
| 5,486,362 | A | 1/1996 | Kitchell et al. |
| 5,512,593 | A | 4/1996 | Dante |
| 5,541,231 | A | 7/1996 | Ruff et al. |
| 5,626,874 | A | 5/1997 | Conte et al. |
| 5,714,519 | A | 2/1998 | Cincotta et al. |
| 5,716,976 | A | 2/1998 | Bernstein |
| 5,719,197 | A | 2/1998 | Kanios et al. |
| 5,731,000 | A | 3/1998 | Ruff et al. |
| 5,738,874 | A | 4/1998 | Conte et al. |
| 5,763,493 | A | 6/1998 | Ruff et al. |
| 5,817,665 | A | 10/1998 | Dante |
| 5,817,666 | A | 10/1998 | Katz |
| 5,856,332 | A | 1/1999 | Dante |
| 5,866,164 | A | 2/1999 | Kuczynski et al. |
| 5,948,799 | A | 9/1999 | Cropp |
| 5,958,962 | A | 9/1999 | Cook |
| 5,977,099 | A | 11/1999 | Nickolson |
| 6,004,970 | A | 12/1999 | O'Malley et al. |
| 6,033,686 | A | 3/2000 | Seth |
| 6,034,091 | A | 3/2000 | Dante |
| 6,048,322 | A | 4/2000 | Kushida |
| 6,071,537 | A | 6/2000 | Shank |
| 6,071,918 | A | 6/2000 | Cook |
| 6,087,386 | A | 7/2000 | Chen et al. |
| 6,096,341 | A | 8/2000 | Seth |
| 6,110,973 | A | 8/2000 | Young |
| 6,120,803 | A | 9/2000 | Wong et al. |
| 6,143,327 | A | 11/2000 | Seth |
| 6,150,366 | A | 11/2000 | Arenson et al. |
| 6,153,223 | A | 11/2000 | Apelian et al. |
| 6,183,778 | B1 | 2/2001 | Conte et al. |
| 6,191,117 | B1 | 2/2001 | Kozachuk |
| 6,197,827 | B1 | 3/2001 | Cary |
| 6,210,716 | B1 | 4/2001 | Chen et al. |
| 6,238,697 | B1 | 5/2001 | Kumar et al. |
| 6,245,766 | B1 | 6/2001 | Watsky |
| 6,248,363 | B1 | 6/2001 | Patel et al. |
| 6,262,049 | B1 | 7/2001 | Coffin et al. |
| 6,274,579 | B1 | 8/2001 | Morgan et al. |
| 6,294,192 | B1 | 9/2001 | Patel et al. |
| 6,306,436 | B1 | 10/2001 | Chungi et al. |
| 6,323,236 | B2 | 11/2001 | McElroy |
| 6,342,496 | B1 | 1/2002 | Jerussi et al. |
| 6,342,515 | B1 | 1/2002 | Masuda et al. |
| 6,344,474 | B1 | 2/2002 | Maruani et al. |
| 6,369,113 | B2 | 4/2002 | Young |
| 6,383,471 | B1 | 5/2002 | Chen et al. |
| 6,387,956 | B1 | 5/2002 | Shapira |
| 6,420,369 | B1 | 7/2002 | Marcotte |
| 6,437,147 | B1 | 8/2002 | Andersen et al. |
| 6,441,038 | B1 | 8/2002 | Loder et al. |
| 6,451,860 | B1 | 9/2002 | Young |
| 6,462,237 | B1 | 10/2002 | Gidwani et al. |
| 6,500,459 | B1 | 12/2002 | Chhabra et al. |
| 6,506,799 | B1 | 1/2003 | Dasseux |
| 6,514,531 | B1 | 2/2003 | Alaux et al. |
| 6,528,520 | B2 | 3/2003 | Clemens |
| 6,541,478 | B1 | 4/2003 | O'Malley et al. |
| 6,548,551 | B2 | 4/2003 | Hinz |
| 6,569,449 | B1 | 5/2003 | Stinchcomb et al. |
| 6,576,256 | B2 | 6/2003 | Liang et al. |
| 6,589,553 | B2 | 7/2003 | Li et al. |
| 6,622,036 | B1 | 9/2003 | Suffin |
| 6,627,223 | B2 | 9/2003 | Percel et al. |
| 6,630,165 | B2 | 10/2003 | Seroff et al. |
| 6,638,535 | B2 | 10/2003 | Lemmens et al. |
| 6,652,882 | B1 | 11/2003 | Odidi et al. |
| 6,682,759 | B2 | 1/2004 | Lim et al. |
| 6,686,337 | B2 | 2/2004 | Connor |
| 6,706,283 | B1 | 3/2004 | Appel et al. |
| 6,713,488 | B2 | 3/2004 | Sadee et al. |
| 6,797,283 | B1 | 9/2004 | Edgren et al. |
| 6,893,660 | B2 | 5/2005 | Li et al. |
| 6,893,661 | B1 | 5/2005 | Odidi et al. |
| 6,905,708 | B2 | 6/2005 | Li et al. |
| 6,923,988 | B2 | 8/2005 | Patel et al. |
| 6,926,907 | B2 | 8/2005 | Plachetka |
| 6,995,169 | B2 | 2/2006 | Chapleo et al. |
| 7,109,198 | B2 | 9/2006 | Gadde et al. |
| 7,375,111 | B2 | 5/2008 | Weber et al. |
| 7,422,110 | B2 | 9/2008 | Zanden et al. |
| 7,425,571 | B2 | 9/2008 | Gadde et al. |
| 7,429,580 | B2 | 9/2008 | Gadde et al. |
| 7,462,626 | B2 | 12/2008 | Weber et al. |
| 7,682,633 | B2 | 3/2010 | Matthews et al. |
| 7,754,748 | B2 | 7/2010 | Gadde et al. |
| 8,088,786 | B2 | 1/2012 | McKinney et al. |
| 8,318,788 | B2 | 11/2012 | McKinney et al. |
| 8,722,085 | B2 | 5/2014 | Mckinney et al. |
| 8,815,889 | B2 | 8/2014 | Cowley et al. |
| 8,916,195 | B2 * | 12/2014 | McKinney et al. ........... 424/468 |
| 8,969,371 | B1 | 3/2015 | Klassen et al. |
| 2001/0025038 | A1 | 9/2001 | Coffin et al. |
| 2001/0046964 | A1 | 11/2001 | Percel et al. |
| 2002/0012680 | A1 | 1/2002 | Patel et al. |
| 2002/0019364 | A1 | 2/2002 | Renshaw |
| 2002/0022054 | A1 | 2/2002 | Sawada et al. |
| 2002/0025972 | A1 | 2/2002 | Hinz |
| 2002/0037836 | A1 | 3/2002 | Henriksen |
| 2002/0044962 | A1 | 4/2002 | Cherukuri et al. |
| 2002/0055512 | A1 | 5/2002 | Marin et al. |
| 2002/0090615 | A1 | 7/2002 | Rosen et al. |
| 2002/0198227 | A1 | 12/2002 | Bernstein |
| 2003/0003151 | A1 | 1/2003 | Chopra |
| 2003/0017189 | A1 | 1/2003 | Wong et al. |
| 2003/0035840 | A1 | 2/2003 | Li et al. |
| 2003/0044462 | A1 | 3/2003 | Subramanian et al. |
| 2003/0054031 | A1 | 3/2003 | Li et al. |
| 2003/0054041 | A1 | 3/2003 | Lemmens et al. |
| 2003/0055008 | A1 | 3/2003 | Marcotte |
| 2003/0055038 | A1 | 3/2003 | Howard et al. |
| 2003/0068371 | A1 | 4/2003 | Oshlack et al. |
| 2003/0087896 | A1 | 5/2003 | Glover |
| 2003/0091630 | A1 | 5/2003 | Louie-Helm et al. |
| 2003/0109546 | A1 | 6/2003 | Fenton |
| 2003/0130322 | A1 | 7/2003 | Howard |
| 2003/0133982 | A1 | 7/2003 | Heimlich et al. |

(56) References Cited

U.S. PATENT DOCUMENTS

| | | |
|---|---|---|
| 2003/0133985 A1 | 7/2003 | Louie-Helm et al. |
| 2003/0135056 A1 | 7/2003 | Anderson et al. |
| 2003/0144174 A1 | 7/2003 | Brennan et al. |
| 2003/0144271 A1 | 7/2003 | Shulman |
| 2003/0147952 A1 | 8/2003 | Lim et al. |
| 2003/0161874 A1 | 8/2003 | Li et al. |
| 2003/0198683 A1 | 10/2003 | Li et al. |
| 2003/0215496 A1 | 11/2003 | Patel et al. |
| 2004/0002462 A1 | 1/2004 | Najarian |
| 2004/0005368 A1 | 1/2004 | Mann et al. |
| 2004/0022852 A1 | 2/2004 | Chopra |
| 2004/0029941 A1 | 2/2004 | Jennings |
| 2004/0047908 A1 | 3/2004 | Lemmens et al. |
| 2004/0059241 A1 | 3/2004 | Suffin |
| 2004/0092504 A1 | 5/2004 | Benja-Athon |
| 2004/0096499 A1 | 5/2004 | Vaya et al. |
| 2004/0101556 A1 | 5/2004 | Li et al. |
| 2004/0105778 A1 | 6/2004 | Lee et al. |
| 2004/0106576 A1 | 6/2004 | Jerussi et al. |
| 2004/0115134 A1 | 6/2004 | Merisko-Liversidge |
| 2004/0122033 A1 | 6/2004 | Nargund et al. |
| 2004/0158194 A1 | 8/2004 | Wolff et al. |
| 2004/0185097 A1 | 9/2004 | Kannan et al. |
| 2004/0204472 A1 | 10/2004 | Briggs et al. |
| 2004/0228915 A1 | 11/2004 | Noack et al. |
| 2004/0228924 A1 | 11/2004 | Oshlack et al. |
| 2004/0242974 A1 | 12/2004 | Glover |
| 2004/0254208 A1* | 12/2004 | Weber et al. .................. 514/282 |
| 2004/0258757 A1 | 12/2004 | Bosch et al. |
| 2005/0004106 A1 | 1/2005 | Romano |
| 2005/0013863 A1 | 1/2005 | Lim et al. |
| 2005/0019385 A1 | 1/2005 | Houze |
| 2005/0019409 A1 | 1/2005 | Edgren et al. |
| 2005/0019412 A1 | 1/2005 | Bosch et al. |
| 2005/0026977 A1 | 2/2005 | Jennings |
| 2005/0026986 A1 | 2/2005 | Maruani et al. |
| 2005/0031691 A1 | 2/2005 | McGurk et al. |
| 2005/0043704 A1 | 2/2005 | Lieberburg |
| 2005/0043705 A1 | 2/2005 | Lieberburg |
| 2005/0043773 A1 | 2/2005 | Lieberburg |
| 2005/0063913 A1 | 3/2005 | Pruitt et al. |
| 2005/0096311 A1 | 5/2005 | Suffin et al. |
| 2005/0112198 A1 | 5/2005 | Challapalli et al. |
| 2005/0112211 A1 | 5/2005 | Gervais et al. |
| 2005/0118268 A1 | 6/2005 | Percel et al. |
| 2005/0137144 A1 | 6/2005 | Gadde et al. |
| 2005/0142195 A1 | 6/2005 | Li et al. |
| 2005/0143322 A1 | 6/2005 | Gadde et al. |
| 2005/0147664 A1 | 7/2005 | Liversidge et al. |
| 2005/0154002 A1 | 7/2005 | Crooks et al. |
| 2005/0163840 A1 | 7/2005 | Sawada et al. |
| 2005/0181049 A1 | 8/2005 | Dong et al. |
| 2005/0214368 A1 | 9/2005 | Kawakami et al. |
| 2005/0214371 A1 | 9/2005 | Di Capua et al. |
| 2005/0214372 A1 | 9/2005 | Di Capua et al. |
| 2005/0215552 A1 | 9/2005 | Gadde et al. |
| 2005/0232990 A1 | 10/2005 | Boehm et al. |
| 2005/0238718 A1 | 10/2005 | Oberegger et al. |
| 2005/0245460 A1 | 11/2005 | Meyerson et al. |
| 2005/0250838 A1 | 11/2005 | Challapalli et al. |
| 2005/0277579 A1 | 12/2005 | Gadde et al. |
| 2006/0009514 A1 | 1/2006 | Gadde et al. |
| 2006/0018933 A1 | 1/2006 | Vaya et al. |
| 2006/0018934 A1 | 1/2006 | Vaya et al. |
| 2006/0024365 A1 | 2/2006 | Vaya et al. |
| 2006/0051418 A1 | 3/2006 | Cowen et al. |
| 2006/0058293 A1 | 3/2006 | Weber et al. |
| 2006/0069086 A1 | 3/2006 | Michalow |
| 2006/0079501 A1 | 4/2006 | Gadde et al. |
| 2006/0100205 A1 | 5/2006 | Weber et al. |
| 2006/0122127 A1 | 6/2006 | Rao et al. |
| 2006/0160750 A1 | 7/2006 | Gadde et al. |
| 2006/0246131 A1 | 11/2006 | Cottinham |
| 2006/0276412 A1 | 12/2006 | Tollefson |
| 2007/0078135 A1 | 4/2007 | Yuan et al. |
| 2007/0099947 A1 | 5/2007 | Dean et al. |
| 2007/0117827 A1 | 5/2007 | Tollefson et al. |
| 2007/0129283 A1 | 6/2007 | McKinney et al. |
| 2007/0148237 A1 | 6/2007 | McKinney et al. |
| 2007/0149451 A1 | 6/2007 | Holmes |
| 2007/0179168 A1 | 8/2007 | Cowley et al. |
| 2007/0185084 A1 | 8/2007 | McKinney et al. |
| 2007/0270450 A1 | 11/2007 | Weber et al. |
| 2007/0275970 A1 | 11/2007 | Weber et al. |
| 2007/0281021 A1 | 12/2007 | McKinney et al. |
| 2008/0027487 A1 | 1/2008 | Patel et al. |
| 2008/0058407 A1 | 3/2008 | Baron et al. |
| 2008/0110792 A1 | 5/2008 | McKinney et al. |
| 2008/0214592 A1 | 9/2008 | Cowley et al. |
| 2009/0018115 A1 | 1/2009 | Gadde et al. |
| 2009/0076108 A1 | 3/2009 | Gadde et al. |
| 2010/0166889 A1 | 7/2010 | Sanfilippo |
| 2010/0190793 A1 | 7/2010 | Weber et al. |
| 2011/0028505 A1 | 2/2011 | McKinney et al. |
| 2011/0098289 A1 | 4/2011 | Gadde et al. |
| 2011/0144145 A1 | 6/2011 | Tollefson |
| 2011/0172260 A1 | 7/2011 | Dunayevich et al. |
| 2012/0010232 A1 | 1/2012 | Weber et al. |
| 2013/0177602 A1 | 7/2013 | McKinney et al. |
| 2013/0245055 A1 | 9/2013 | Wright |
| 2013/0252995 A1 | 9/2013 | Dunayevich et al. |
| 2014/0080857 A1 | 3/2014 | McKinney et al. |
| 2014/0322318 A1 | 10/2014 | McKinney et al. |
| 2014/0364468 A1 | 12/2014 | Gadde et al. |
| 2015/0119417 A1 | 4/2015 | Tollefson |

FOREIGN PATENT DOCUMENTS

| | | |
|---|---|---|
| EP | 0 294 028 | 12/1988 |
| EP | 0 442 769 | 8/1991 |
| EP | 0 541 192 | 5/1993 |
| EP | 0 598 309 | 5/1994 |
| EP | 1 275 373 | 1/2003 |
| EP | 1 759 701 | 7/2007 |
| EP | 1 813 276 | 8/2007 |
| JP | 2003-509349 | 3/2003 |
| RU | 2214241 | 10/2003 |
| WO | WO 83/03197 | 9/1983 |
| WO | WO 90/13294 | 11/1990 |
| WO | WO 94/20100 | 9/1994 |
| WO | WO 96/09047 | 3/1996 |
| WO | WO 97/06786 | 2/1997 |
| WO | WO 97/06787 | 2/1997 |
| WO | WO 97/41873 | 11/1997 |
| WO | WO 98/00130 | 1/1998 |
| WO | WO 99/16375 | 4/1999 |
| WO | WO 99/37305 | 7/1999 |
| WO | WO 99/38504 | 8/1999 |
| WO | WO 00/50020 | 8/2000 |
| WO | WO 00/51546 | 9/2000 |
| WO | WO 00/61139 | 10/2000 |
| WO | WO 00/62757 | 10/2000 |
| WO | WO 00/76493 | 12/2000 |
| WO | WO 01/01973 | 1/2001 |
| WO | WO 01/26641 | 4/2001 |
| WO | WO 01/52833 | 7/2001 |
| WO | WO 01/52851 | 7/2001 |
| WO | WO 01/58447 | 8/2001 |
| WO | WO 01/58451 | 8/2001 |
| WO | WO 01/62257 | 8/2001 |
| WO | WO 01/78725 | 10/2001 |
| WO | WO 01/85257 | 11/2001 |
| WO | WO 02/09694 | 2/2002 |
| WO | WO 02/24214 | 3/2002 |
| WO | WO 02/087590 | 11/2002 |
| WO | WO 03/013524 | 2/2003 |
| WO | WO 03/013525 | 2/2003 |
| WO | WO 03/013479 | 3/2003 |
| WO | WO 03/092682 | 11/2003 |
| WO | WO 03/097051 | 11/2003 |
| WO | WO 2004/002463 | 1/2004 |
| WO | WO 2004/009015 | 1/2004 |
| WO | WO 2004/024096 | 3/2004 |
| WO | WO 2004/052289 | 6/2004 |

(56) References Cited

FOREIGN PATENT DOCUMENTS

| | | |
|---|---|---|
| WO | WO 2004/054570 | 7/2004 |
| WO | WO 2004/054571 | 7/2004 |
| WO | WO 2004/071423 | 8/2004 |
| WO | WO 2004/091593 | 10/2004 |
| WO | WO 2004/100956 | 11/2004 |
| WO | WO 2004/100992 | 11/2004 |
| WO | WO 2004/110368 | 12/2004 |
| WO | WO 2004/110375 | 12/2004 |
| WO | WO 2005/000217 | 1/2005 |
| WO | WO 2005/077362 | 2/2005 |
| WO | WO 2005/032555 | 4/2005 |
| WO | WO 2005/049043 | 6/2005 |
| WO | WO 2005/079773 | 9/2005 |
| WO | WO 2005/089486 | 9/2005 |
| WO | WO 2006/049941 | 5/2006 |
| WO | WO 2006/052542 | 5/2006 |
| WO | WO 2006/055854 | 5/2006 |
| WO | WO 2006/088748 | 8/2006 |
| WO | WO 2007/012064 | 1/2007 |
| WO | WO 2007/047351 | 4/2007 |
| WO | WO 2007/085637 | 8/2007 |
| WO | WO 2008/119978 | 10/2008 |
| WO | WO 2009/158114 | 12/2009 |
| WO | WO 2013/184837 | 12/2013 |

OTHER PUBLICATIONS

Adis Data Information BV, 2010, Naltrexone/Bupropion Contrave®; Naltrexone SR/Bupropion SR, Adis R&D Profile, 10(1):25-32.
Albaugh et al., 2005, Topiramate prevents the rapid weight gain and adiposity in a model of atypical antipsychotic drug-induced obesity, Fed. of American Soc. For Experimental Biology, 19(5, Suppl. S, Part 2):A1130.
Alger et al., Apr. 1991, Effect of a tricyclic antidepressant and opiate antagonist on binge-eating behavior in normoweight bulimic and obese, binge-eating subjects, The American Journal of Clinical Nutrition, 53(4):865-871.
Altman et al., 2005, Standard Deviations and Standard Errors, BMJ, 331:903.
Anderson et al., 2002, Bupropion SR enhances weight loss: a 48-week double-blind, placebo-controlled trial, Obesity R., 10(7):633-641.
Appolinario et al., 2004, Pharmacological Approaches in the Treatment of Binge Eating Disorder, Current Drug Targets, 5:301-307.
Aronne et al., 2003, Weight gain in the treatment of mood disorders, J. Clin Psychiatry, 64(suppl 8).
Asconape, 2002, Some Common Issues in the Use of Antiepileptic Drugs, Seminars in Neurology; 22(1):27-39.
Astrup et al., Mar. 1991, Thermogenic Synergism Between Ephedrine and Caffeine in Healthy Volunteers: A Double-Blind, Placebo-Controlled Study, Metabolism, 40(3):323-329.
Atkinson et al. (Oct. 1985) Effects of long-term therapy with naltrexone on body weight in obesity, Clinical Pharmacology & Therapeutics, 38:419-422.
Atkinson, 2003, Clinical Guidelines on the identification, Evaluation, and pharmacologic treatment of obesity in Adults, Online, 07-25, URL:http://www.endotext.org.obesity/obesity15b/obesity15b.htm.
Atlantis et al., Oct. 6, 2009, Obesity and depression or anxiety, BMJ 2009:339:B3868.
Ayala (2000) Weight Loss Associated With the Administration of Zonisamide, AES Proceedings, Epilepsia 41(Suppl. 7) :99—No.2. 041.
Ayala et al., Dec. 1-6, 2000, Weight loss associated with the administration of zonisamide, a compendium of posters and platform session for ZonegranTM and Diastat®, Annual Meeting 2000 of the American Epilepsy Society, Los Angeles, CA.
Baldassano et al. (2006) Acute treatment of bipolar depression with adjunctive zonisamide: a retrospective chart review, Disorders 6:432-434.

Barr et al. 1993. The serotonin hypothesis of obsessive compulsive disorder. International Clinical Psychopharmacology, 8(2):79-82.
Bastani et al. 1991. Serotonin uptake and imipramine binding in the blood platelets of obsessive-compulsive disorder patients. Biol. Psychiatry, 30:131-139.
Bays et al., Aug. 1, 2007, Adiposopathy: treating pathogenic adipose tissue to reduce cardiovascular disease risk, Current Treatment Options in Cardiovascular Medicine, 9(4):259-271.
Beelen et al. (2001) Asymptomatic QTC prolongation associated with queitiapine fumarate overdose in a patient being treated with risperidone, Human & Experimental Toxicology 20:215-219.
Benjamin et al. 1993. Naltrexone and fluoxetine in Prader-Willi syndrome. J. Am. Acad. Child Adolesc. Psychiatry, 32(4):870-873.
Bergeron et al. 2002. Sertraline and fluoxetine treatment of obsessive-compulsive disorder: Results of a double-blind, 6-month treatment study. Journal of Clinical Psychopharmacology, 22(2):148-154.
Berke et al. (Jul. 15, 2000) Medical Management of Obesity, American Academy of Family Physicians, 62(2):419-26 Abstract.
Billett et al. 1997. Obsessive compulsive disorder, response to serotonin reuptake inhibitors and the serotonin transporter gene. Molecular Psychiatry, 2:403-406.
Blanchard et al. (2003) Pancreatitis Treated with Didanosine and Tenofabir Disoproxil Fumarate Clinical Infectious Diseases, 37:57-62.
Broocks et al. 1998. Higher prevalence of obsessive-compulsive symptoms in patients with blepharospasm than in patients with hemifacial spasm. Am. J. Psychiatry, 155:555-557.
Bupropion (Oral Route), MayoClinic.com, 19 pp., 2009.
Calabrese et al. (Sep. 2000) Letters to the Editors, Lamotrigine and Clozapine for Bipolar Disorder, American J. of Psychiatry, 157:1523.
Campana et al., Jan. 2005, P.6.034 Naltrexone and cravings: does it work with eating disorders?, European Neuropsychopharmacology, 15:S283.
Carlsen et al. (Jan. 1998) Evidence for dissociation of insulin-and weight-reducing effects of metformin in non-diabetic male patients with coronary heart disease, Diabetes Research and Clinical Practice Amersterdam, 39(1):47-54.
Carpenter et al. (Jan. 1, 1999) Mirtazapine Augmentation in the Treatment of Refractory Depression, J Clin Psychiatry, 60:1.
Carrion, 1995. Naltrexone for the treatment of trichotillomania: A case report. J. Clin. Psychopharmacol., 15(6):444-445.
Carroll (2003) Medicinal Chemistry Division Award Address: Monoamine Transporters and Opioid Receptors. Targets for Addiction Therapy, J. Med. Chem; 46(10):1775-1794.
Carter et al. 2003. Pharmacologic treatment of binge-eating disorder, The International Journal of Eating Disorders, 34(Suppl):S74-S88.
Carter et al. 2003. Pharmacologic treatment of binge-eating disorder. Primary Psychiatry, 10(10)31-36.
Casado et al., Apr. 2003, Sibutramine decreases body weight gain and increases energy expenditure in obese Zucker rats without changes in NPY and orexins, Nutr Neurosci, 6(2):103-111 (abstract).
Cash et al. (2000) Attitudes about antidepressants: Influence of information about weight-related side effects, Perceptual and Motor Skills, 90:453-456.
Casner et al. 1996. Naltrexone and self-injurious behavior: A retrospective population study. Journal of Clinical Psychopharmacology, 16(5):389-394.
Chen et al. (Jan. 2004) Synergistic Effects of Cannabinoid inverse agonist AM251 and opioid antagonist nalmefene on food intake, Brain Res, 999:22-230.
Chen et al., 2005, Combination treatment of clozapine and (No Suggestions) in resistant rapid-cycling bipolar disorder, Clin. Neuropharmacol. 28(3):136-138.
Chen et al., Jun. 2003, Nonketotic hyperosmolar syndrome from olanzapine, lithium, and valproic acid cotreatment, Annals of Pharmacotherapy, 37(6):919-920.
Chengappa et al. (2002) Changes in body Weight and Body mass index among psychiatric patients receiving lithium, valproate, or topiramate: an open-label, nonrandomized chart review, Clinical Therapeutics, 24(10): 1576-1584.
Ching, Mar. 1980, Influence of diphenylhydantoin upon oral glucose tolerance test in obesity, Chinese Medical Journal, 27(1):432-439.

(56) References Cited

OTHER PUBLICATIONS

Chouinard et al. 1996. Potentiation of fluoxetine by aminoglutethimide, an adrenal steroid suppressant, in obsessive-compulsive disorder resistant to SSRIs: A case report. Prog. Neuro-Psychopharmacol. & Biol. Psychiat., 20:1067-1079.
Clapham et al. (2001) Anti-obesity drugs: a critical review of current therapies and future opportunities. Pharmacology & Therapeutics. 89:81-121.
Clark et al., 2003, Diabetes mellitus associated with atypical antipsychotic medications, Diabetes Technology & Therapeutics, 5(4):669-683.
Clinical Trial: Drug Treatment for Depressed Alcoholics (Naltrexone/Fluoxetine). (n.d.) Retrieved Jun. 28, 2007, from http://www.clinicaltrials.gov/ct/show/NCT00006204;jsessionid+FED6D0856E098BC0B1940E464179B71B?order=28.
ClinicalTrials.gov archive, Apr. 21, 2008, A phase 3 study comparing the safety and efficacy of naltrexone sr/bupropion sr and placebo in obese subjects with type 2 diabetes mellitus, 3 pp.
ClinicalTrials.gov archive, May 2012, Cardiovascular outcomes study of Naltrexone SR/Bupropion SR in overweight and obese subjects with cardiovascular risk factors (the light study), 4 pp.
Colosimo, et al. 1999. Motor fluctuations in Parkinson's disease: Pathophysiology and treatment. European Journal of Neurology, 6:1-21.
Cone et al. (2001) The arcuate nucleus as a conduit for diverse signals relevant to energy homeostasis, Int'l Journal of Obesity, 25(5):563-567.
Croft et al. (Apr. 2002) Effect on body weight of bupropion sustained-release in patients with major depression treated for 52 weeks, Clinical Therapeutics 24(4):662-672.
Cunningham, May 1963, Diethylpropion in the treatment of obesity, The Journal of the College of General Practitioner, 6(2):347-349.
Cuparencu et al., 1993, Effects of some benzodiazepines on glycemia in albino rats, Romanian Journal of Physiology, 30(1-2):7-15 (abstract).
Dechant et al., 1991, Paroxetine: a review of its pharmacodynamic and pharmacokinetic properties, and therapeutic potential in depressive illness, Drugs, 41:225-253.
Dembowski et al. (2003) Successful Antimanic Treatment and Mood Stabilization with Lamotrigine, Clozapine, and Valproate in a Bipolar Patient after Lithium-induced Cerebellar Deterioration, Letter Pharmacopsychiatry, 36:83-86.
Deshmukh et al. (Jul. 2003) Managing weight gain as a side effect of antidepressant therapy, Cleveland Clinic Journal of Medicine, vol. 70.
DeSimone et al. (2005) Carbonic anhydrase inhibitors. Zonisamide is an effective inhibitor of the cytosolic isozyme II and mitochondrial isozyme V: Solution and x-ray crystallographic studies, Bioorganic & Medicinal Chemistry Letters, 15:2315-2320.
Devlin et al. (2000) Open treatment of overweight binge eaters with phentermine and fluoxetine as an adjunct to cognitive-behavioral therapy. Int. J. Eating Disord; 28:325-332.
Durgin et al., 2005, Pharmaceutical Practice for Technicians, 3rd Edition, Thomson Delmar Learning, p. 174.
Dursun et al. (2001) Accelerated Weight Loss After Treating Refractory Depression with Fluoxetine Plus Topiramate: Possible Mechanism of Action, Canadian Journal of Psychiatry, 46(3):287-288.
Dursun et al. (2001) Augmenting Antipsychotic treatment with Lamotrigine or topiramate in patients with treatment-resistant Schizophrenia: a naturalistic case-series outcome study Journal of Psychopharmacology 15(4):297-301.
Dursun et al. (2001) Psychopharmacology for the Clinician Psychopharmacologie Pratiqu, Journal of Psychiatry Neuroscience, 26(2):168.
Dursun et al. (Oct. 1999) Clozapine Plus Lamotrigine in Treatment-Resistant Schizophrenia, Arch Gen Psychiatry, 56:950-951.
Dursun et al. (Winter 2002) Lamotrgine-Clozapine Combination in Refractory Schizophrenia: Three Cases, J. Neuropsychiatry Clin. Neuroscience, 14(1):86.
Dwyer et al., 2002, Psychoactive drugs affect glucose transport and the regulation of glucose metabolism, International Review of Neurobiology, 51:503-530.
El-Haschimi et al. 2000. Two defects contribute to hypothalamic leptin resistance in mice with diet-induced obesity. The Journal of Clinical Investigation, 105(12):1827-1832.
Erez et al., 1982, Narcotic antagonistic potency of bivalent ligands which contain β-naltrexamine. Evidence for bridging between proximal recognition sites, J. Med. Chem., 25:847-849.
Erfurth et al., Mar. 2002, Bupropion as add-on strategy in difficult-to-treat bipolar depressive patients, Neurophsychobiology, 45(Supplement 1):33-36.
Erzegovesi et al. 2001. Clinical predictors of drug response in obsessive-compulsive disorder. Journal of Clinical Psychopharmacology, 21(5):488-492.
Esposito-Avella et al. (Jan. 1973) Studies on the protective effect of diphenylhyndantoin against alioxan diabetes in mice, Proceedings of the Society for Experimental Biology & Medicine, 142(1):82-85.
Ettmayer et al, May 6, 2004, Lessons learned from marketed and investigational prodrugs, J. Med. Chem, 47(10):2393-2404.
Faught et al. (2001) Randomized Controlled Trial of Zonisamide for the Treatment of Refractory Partial-Onset Seizures., Neurology; 57(10):1774-1779.
Fava, 2000, Weight Gain and Antidepressants. J Clin Psychiatry; 61(suppl 11):37-41.
Ferre et al. (1996) Correction of diabetic alterations by glucokinase. Proc. Natl. Acad. Sci. USA, 93:7225-7230.
Ferre et al. (1996) Evidence from transgenic mice that glucokinase is rate limiting for glucose utilization in the liver, The FASEB Journal, 10:1213-1218.
Fingl et al., The Pharmacological Basis of Therapeutics. Chapter 1: General Principles, pp. 1-46 (1975).
Fontela et al., Mar. 1986, Blocking effect of naloxone, dihydroergotamine and adrenalectomy in lithium-induced hyperglycaemia and glucose intolerance in the rat, Acta Endocrinologica, 111(3):342-348 (abstract).
Fujioka et al., Jan. 1987, Contribution of intra-abdominal fat accumulation to the impairment of glucose and lipid metabolism in human obesity, Metabolism, 36(1):54-59.
Fukagawa et al. (Nov. 2001) Monoaminergic anorectic agents, Nippon Yikurigaku Zasshi, 118(5):303-8, 2001 Abstract.
Fulghesu et al. (Aug. 1993) Long-term naltrexone treatment reduces the exaggerated insulin secretion in patients with polycystic ovary disease, Obstetrics & Gynecology, 82(2):191-197.
Fuller et al. (1989) Fluoxetine: A Serotonergic Appetite Suppressant Drug, Drug Development Research, 17(1):1-15.
Gadde et al, "Zonisamide in Obesity: A 16-Week Randomized Trial", No. NR473, New Research, American Psychiatric Association 2002 Annual Meeting, May 18-23, 2002, Philadelphia, Pennsylvania (abstract).
Gadde et al, Randomized Trial of Weight Loss Efficacy of Zonisamide, No. 304, 26(Suppl. 1), Journal of the International Association for the Study of Obesity, Ninth International Congress on Obesity, Sao Paolo, Brazil, Aug. 24-29, 2002.
Gadde et al. "Bupropion for Weight Loss: An Investigation of Efficacy and Tolerability in Overweight and Obese Women" Obesity Research 9 (9): 544-551 (2001).
Gadde et al. , "Zonisamide for Weight Loss in Obese Adults—A Randomized Controlled Trial" JAMA 289 (14): 1820-1825 (2003).
Gadde et al., 2002, Randomized controlled trial of zonisamide for treating obesity, Epilepsia 43 Suppl. 7:218 (abstract).
Gadde et al., 2003, Zonisamide enhances weight loss in patients with obesity. Inpharma, 1383(84):9.
Gadde et al., May 1999, Bupropion Sustained Release in Obesity: A Randomized Double-Blind, Placebo-Controlled Study, No. NR634, New Research Program & Abstracts, American Psychiatric Association, 1999 Annual Meeting, The Clinician, Washington, D.C.
Gadde et al., Sep. 1999, A randomized double-blind placebo-controlled study of bupropion sustained release in obesity, European Neuropsychopharmacology, 9(5):366.
Gatley et al.,1996, $^{123}$I-labeled AM251: a radioiodinated ligand which binds in vivo to mouse brain cannabinoid $CB_1$ receptors. European Journal of Pharmacology; 307:331-338.

(56) References Cited

OTHER PUBLICATIONS

Gehlert et al. (Oct. 1998) The Selective Norepinephrine Reuptake Inhibitor, LY368975, Reduces Food Consumption in Animal Models of Feeding, J. Pharmacology and Experimental Therapeutics, 87(1):122-7 Abstract.

Gerich et al. (1972) In vitro inhibition of pancreative glucagon secretion by diphenylhydantoin, Journal of Clinical Endocrinology and Metabolism 35(6):823-824.

Gerra et al. 1995. Hostility in heroin abusers subtypes: Fluoxetine and naltrexone treatment. Prog. Neuro-Psychopharmacol. & Biol. Psychiat., 19:1225-1237.

Gerra et al., Sep. 30, 2006, Effects of olanzapine on aggressiveness in heroin dependent patients, Progress in Neuro-Psychopharmacology & Biological Psychiatry, 30(7):1291-1298.

Ginsberg et al. (2000) Effects of Mood Stabilizers on Weight, Primary Psychiatry 7(5):49-58.

Givens et al. (1987) Reduction of hyperinsulinemia and insulin resistance by opiate receptor blockade in the polycystic ovary syndrome with acanthosis nigricans, Journal of Clinical Endocrinology and Metabolism, 64(2):377-382.

Glass et al., 1999, Opioids and food intake: distributed functional neural pathways?, Neuropeptides, 33(5):360-368.

Goldstein et al. (Mar. 1994) Fluoxetine: a randomized clinical trial in the treatment of obesity, International Journal of Obesity and Related Metabolic Disorders, 17(3):129-135, CAS accession #9424430.

Goodman et al. 1989. The Yale-Brown obsessive compulsive scale. Arch. Gen. Psychiatry, 46:1006-1011.

Gordon et al. (Jun. 1999) Mood Stabilization and Weight Loss with Topiramate American Journal of Psychiatry, American Psychiatric Association, Washington D.C., 156(6):968-969.

Gormally et al., 1982, The assessment of binge eating severity among obese persons, Addict Behav, 7(1):47-55.

Grady (Mar. 15, 2003) Quest for Weight-Loss Drug Takes an Unusual Turn, The New York Times—Health, www.nytimes.com, 3 pp.

Grant et al. 2004. Impulse control disorders: Clinical characteristics and pharmacological management. Annals of Clinical Psychiatry, 16:27-34.

Grant et al. 2004. Pharmacotherapy outcome in older pathological gamblers: A preliminary investigation. Journal of Geriatric Psychiatry and Neurology, 17(1):9-12.

Grant et al. 2006. Compulsive aspects of impulse-control disorders. Psychiatr. Clin. North Am., 29(2):539-x.

Greenberg et al. 1998. Delayed obsessive-compulsive disorder symptom exacerbation after a single dose of a serotonin antagonist in fluoxetine-treated but not untreated patients. Psychopharmacology, 140:434-444.

Greenway et al. (2002) A Long-acting Leptin Analog does not Enhance Fat, Visceral Fat, or Weight Loss When Combined with Caffeine Ephedrine in Obese Subjects, International Journal of Obesity, S136.

Greenway et al. (Jul. 1999) Double-Blind, Randomized, Placebo-Controlled Clinical Trials with Non-prescription Medications for the Treatment of Obesity, Obesity Research, 7(4):370-78.

Greenway et al., Dec. 2009, Comparison of combined bupropion and naltrexone therapy for obesity with monotherapy and placebo, J. Clin Endocrinol Metab, 94(12):4898-4906.

Greenway et al., Jan. 2009, Rational design of a combination medication for the treatment of obesity, Obesity, 17(1):30-39.

Greenway et al., Jun. 2006, Bupropion and naltrexone for the treatment of obesity, Diabetes: Abstract Book: 66th Scientific Sessions, 55(Supplement 1):A395.

Greenway et al., Jun. 2006, Bupropion and naltrexone for the treatment of obesity, poster, 1 pg.

Greenway et al., Oct. 22, 2010, Effect of naltrexone plus bupropion on weight loss in overweight and obese adults (COR-I): a multicentre, randomized, double-blind, placebo-controlled, phase 3 trial, Lancet, 376:595-605.

Greist et al. (Apr. 1995) Double-blind Parallel Comparison of Three Dosages of Sertraline and Placebo in Outpatients With Obsessive-compulsive Disorder, Arch Gen Psychiatry, 52:289-295.

Grunenthal, Neo-Eunomin Gebrauschsinformation, Neunomin Prescription Information, Feb. 2004, pp. 1-2.

Hagan et al., Dec. 1997, Combined naloxone and fluoxetine on deprivation-induced binge eating of palatable foods in rats, Pharmacol Biochem Behav, 58(4):1103-1107.

Hahn et al. (1985) Irreversible opiate agonists and antagonists. III. Phenylhydrazone derivatives of naloxone and oxymorphone. J. Pharm. Exper. Therapeutics; 235:846-850.

Halpern et al., Jul. 27, 2010, Combinations of drugs in the treatment of obesity, Pharmaceuticals, 3:2398-2415.

Hamidi et al. 2007. Naltrexone in obsessive-compulsive disorder: An open-label trial. Iranian Journal of Psychiatry and Behavioral Sciences, 1(1):16-21.

Harrison's Principles of Internal Medicine, Braunwald et al., The epilepsies and convulsive disorders, Eleventh Edition, McGraw-Hill Book Company, pp. 1921-1930 (1987).

Hashiguti et al. (1993) Simultaneous determination of in vivo hydroxylation of tyrosine and tryptophan in rat striatum by microdialysis-HPLC: relationship between dopamine and serotonin biosynthesis; Journal of Neural Transmission, 93:213-223.

Hausenloy, 2009, Contrave™: Novel treatment for obesity, Future Lipidology, 4(3):279-285.

Hollander et al. 1991. Effects of chronic fluoxetine treatment on behavioral and neuroendocrine responses to meta-chlorophenylpiperazine in obsessive-compulsive disorder. Psychiatry Research, 36:1-17.

Horne et al., Jul. 1988, Treatment of bulimia with bupropion: a multicenter controlled trial, The Journal of Clinical Psychiatry, 49(7):262-266.

Hussey et al., 2002, Synthesis of a β-estradiol-biotin chimera that potently heterodimerizes estrogen receptor and streptavidin proteins in a yeast three-hybrid system, J. Am. Chem. Soc., 125:3692-3693.

Insulin Resistance and Pre-diabetes, http://diabetes.niddk.hih.gov/DM/pubs/insulineresistance/, NIH Publication No. 09/4893, Oct. 2008, 9 pp.

Islam et al., 1994, Naltrexone, Serotonin Receptor Subtype Antagonists, and Carbohydrate Intake in Rats, Pharmacology Biochemistry and Behavior, 48(1):193-201.

Jain et al. (Oct. 2002) Bupropion SR vs. Placebo for Weight Loss in Obese Patients with Depressive Symptoms, Obesity Research, 10:1049-56.

Jallon et al. (2001) Bodyweight gain and anticonvulsants: a comparative review. Drug Safety; 24(13):969-978.

Janssen et al., 1999, Effects of sex on the change in visceral, subcutaneous adipose tissue and skeletal muscle in response to weight loss, International Journal of Obesity, 23, pp. 1035-1046.

Japanese Journal of Clinical Psychiatry (1987 16(1):123-132), and English-language version of Japanese Office Action citing the same (dated Oct. 28, 2008).

Johnson et al., Oct. 14, 2010, Food effects on the pharmacokinetics of morphine sulfate and naltrexone hydrochloride extended release capsules, Advances in Therapy, 27(11):846-858.

Jonas et al.., 1986, Treatment of binge-eating an open-study of naltrexone, Society for Neuroscience Abstracts, 12(1):595.

Jones et al., 2003, Effect of naltrexone on food intake and body weight in Syrian hamsters depends on metabolic status, Physiology & Behavior 28:67-72.

Kanba et al. (1994) The first open study of zonisamide, a novel anticonvulsant, shows efficacy in mania. Progress in Neuro-Psychopharmacology and Biological Psychiatry; 18(4):707-715.

Kelly et al., 2006, Adjunct divalproex or lithium to clozapine in treatment-resistant schizophrenia, Psychiatric Quarterly, 77(1):81-94.

Kennett et al., Nov. 2010, New approaches to the pharmacological treatment of obesity: can they break through the efficacy barrier?, Pharmacology Biochemistry and Behavior, 97(1):63-83.

Khaylis et al., Nov. 2010, A review of efficacious technology-based weight-loss interventions: five key components, Telemedicine and e-Health, 16(9):931-938.

Kim et al. 1990. Open fixed dose trial of fluoxetine in the treatment of obsessive compulsive disorder. Drug Development Research, 19:315-319.

(56) References Cited

OTHER PUBLICATIONS

Kimura et al., 1992, Pharmacokinetic interaction of zonisamide in rats: effects of other antiepileptics on zonisamide, J. Pharmacobio-Dyn. 15:631-639.

Kiptoo et al. (2006) Enhancement of Transdermal delivery or 6-B-naltrexol via a codrug linked to hydroxybupropion, Journal of Controlled Release 113:137-145.

Kirkham et al. (2001) Synergistic effects of opioid and cannabinoid antagonists on food intake. Psychopharmacology; 153:267-270.

Kirov et al. (2003) Add-on topiramate reduces weight in overweight patients with affective disorders: a clinical case. BMC Psychiatry, 5:19, 8 pp.

Kivimaki et al., Common mental disorder and obesity—insight from four repeat measures over 19 years: prospective Whitehall II cohort study, BMJ 2009; 339:b3765.

Klok et al., 2002, Cholesteryl-(l-lactic acid)n building blocks for self-assembling biomaterials, Macromolecules, 35:746-759.

Kolb et al. (1985) Synthesis and Pharmacological Characterization of Fluorescent Opioid Receptor Probes. A. Pharmaceutical Res, 2(6):266-271.

Korner et al. (2003) The emerging science of body weight regulation and its impact on obesity treatment, J. Clin. Invest. 111(5):565-570.

Kossard, et al. 2006. Defining urticarial dermatitis: A subset of dermal hypersensitivity reaction pattern. Arch. Dermatol., 142:29-34.

Krauss et al. 1997. Tics secondary to craniocerebral trauma, Movement Disorders, 12(5):776-782.

Kristeller et al., Jan. 12, 1999, An exploratory study of a meditation-based intervention for binge eating disorder, J. Health Psychol, 4(3):357-363.

Krupitsky et al. 2006. Naltrexone with or without fluoxetine for preventing relapse to heroin addiction in St. Petersburg, Russia. Journal of Substance Abuse Treatment, 31:319-328.

Kuk et al., 2006, Visceral fat is an independent predictor of all-cause mortality in men, Obesity, 14(2):336-341.

Kushner et al. (Mar. 2002) Obesity pharmacology: past, present, and future, Current Opinion in Gastroenterology, pp. 213-220.

Landabaso et al. 1998. A randomized trial of adding fluoxetine to a naltrexone treatment programme for heroin addicts. Addiction, 93(5):739-744.

Le Bourdonnec et al., 2002, Reporter affinity labels: an o-phthalaldehyde derivative of β-naltrexamine as a fluorogenic ligand for opioid receptors, J. Med. Chem., 43(13):2489-2492.

Leppik (Dec. 2004) Zonisamide: chemistry, mechanism of action, and pharmacokinetics, Seizure, 13(Suppl 1):55-9; discussion S10.

Leppik et al. (1993) Efficacy and safety of zonisamide: results of a multicenter study. Epilepsy Research; 14:165-173.

Lesch et al. 1991. Long-term fluoxetine treatment decreases 5-HT1A receptor responsivity in obsessive-compulsive disorder. Psychopharmacology, 105:415-420.

Lessig et al. (Dec. 2001) Topiramate for Reversing Atypical Antipsychotic Weight Gain, J. Am. Child Adolesc. Psychiatry 40(12):1364.

Levy et al. (Nov. 2002) Topiramate Produced Weight Loss Following Olanzapine-Induced Weight Gain in Schizophrenia, J. Clin. Psychiatry, 63(11):1045.

Levy et al. 1985. Utility of free level monitoring of antiepileptic drugs. Epilepsia, 26(3):199-205.

Lin et al. 2000. Development of high fat diet-induced obesity and leptin resistance in C57B1/6J mice. International Journal of Obesity, 24:639-646.

López-Ibor, Jr. et al. 1996. Double-blind comparison of fluoxetine versus clomipramine in the treatment of obsessive compulsive disorder. European Neuropsychopharmacology, 6:111-118.

Lowry, Feb. 2008, Study: bupropion-naltrexone combo best for weight loss, Clinical Psychiatric News, 1 pp.

Luppino et al., Mar. 2010, Overweight, obesity, and depression: a systematic review and meta-analysis of longitudinal studies, Arch Gen Psychiatry, 67(3):220-229.

Malcolm et al. (Jun. 1985) A Controlled Trial of Naltrexone in Obese Humans, International Journal of Obesity, 9:347-353.

Malhotra et al. (2002) Medical Management of Obesity Associated With Mental Disorders, Journal of Clinical Psychiatry, 63(suppl 4):24-32.

Marrazzi et al., Feb. 1995, Binge eating disorder: response to naltrexone, International Journal of Obesity, 19(2):143-145.

Matsuura (2000) Indication for Anterior Temporal Lobectomy in Patients with Temporal Lobe Epilepsy and Psychopathology, Epilepsia, 41(Suppl. 9):39-42.

McDougle et al. (Aug. 2000) a double-blind, placebo-controlled study of risperidone addition in serotonin reuptake inhibitor-refractory obsessive-compulsive disorder, Archive of General Psychiatry, 57(8):794-801.

McElroy et al. (2000) Pharmacologic agents for the treatment of acute bipolar mania, Biological Psychiatry, 48(6):539-557.

McElroy et al. (2004) Zonisamide in the Treatment of Binge-Eating Disorder: An Open-Label, Prospective Trial, J. Clin. Psychiatry, 65(1):50-56.

McElroy et al. (2004) Zonisamide is effective in the treatment of binge-eating disorder. lnpharma; 1428:10.

McLaughlin et al. (2003) The cannabinoid CB1 antagonists SR 141716A and AM 251 suppress food intake and food-reinforced behavior in a variety of tasks in rats. Behavioral Pharmacology; 14:583:588.

McLaughlin et al., 1983, Nalmefene decreases meal size, food and water intake and weight gain in Zucker rats, Pharmacology Biochemistry and Behavior, 19(2):235-240 (abstract).

Meyer, Dec. 2008, Alleviation of both binge eating and sexual dysfunction with naltrexone, Journal of Clinical Psychopharmacology, 28(6):722-723.

Michelson et al. (Nov. 2001) Atomexetine in the Treatment of Children and Adolescents with Attention Deficit/Hyperactivity Disorder: A Randomized, Placebo-Controlled, Dose-Response Study, Pediatrics,108(5):E83 Abstract.

Midha et al., May 2005, Exposure measures applied to the bioequivalence of two sustained release formulations of bupropion, International Journal of Clinical Pharmacology and Therapeutics, 43(5):244-254.

Millet et al. 1999. Obsessive-compulsive disorder: Evaluation of clinical and biological circadian parameters during fluoxetine treatment. Psychopharmacology, 146:268-274.

Mitchell et al. (1987) High-Dose Naltrexone Therapy and Dietary Counseling for Obesity, Biological Psychiatry, 22:35-42.

Monteleone et al. 1995. Plasma melatonin and cortisol circadian patterns in patients with obsessive-compulsive disorder before and after fluoxetine treatment. Psychoneuroendocrinology, 20(7):763-770.

Morris, III (Dec. 3, 2000) The Effect of Zonisamide Administration on Patient Weight, A Scientific Exhibit at the American Epilepsy Society Annual Meeting, Los Angeles, California.

Must et al. (Oct. 27, 1999) The disease burden associated with overweight and obesity, JAMA, 282(16):1523-1529.

Najim et al., Dec. 1, 1993, Role of endorphins in benzodiazepine-induced hyperglycaemia in mice, Pharmacology Biochemistry and Behavior, 46(4):995-997.

Naltrexone (Oral Route), MayoClinic.com, 11 pp., 2009.

Nash et al., Jul. 1, 2004, Anxiety disorders, Medicine, 32(7):17-21.

National Institutes of Health, Apr. 18, 2008, Efficacy and safety study of combination therapy to treat uncomplicated obesity, http://clinicaltrials.gov/show/NCT00364871, 5 pp.

Navarro et al. (Jun. 2001) Topiramate for Clozapine-Induced Seizures, Am. J. Psychiatry, 158(6):968-969.

NDA 20-711, Approval Letter of Application No. NDA 20-711, Department of Health and Human Services, May 14, 1997, 4 pp.

NDA 20-789/S-005 ZONEGRAN (zonisamide) Capsules 100 mg, FDA Approved Labeling Text dated Oct. 7, 2002, 2 pp.

NDA20-789, ZONEGRAN (zonisamide) Capsules 100 mg, FDA Approved Labeling Text, p. 1-24 (Mar. 27, 2000).

Neumeister et al. 1999. Addition of naltrexone to fluoxetine in the treatment of binge eating disorder. Am. J. Psychiatry, 156(5):797.

NIH Publication No. 05-3892, Dec. 2004, National Diabetes Statistics, 18 pp.

Ninan et al., 1992, An improved synthesis of noroxymorphont, Tetrahedron., 48(32):6709-6716.

(56) References Cited

OTHER PUBLICATIONS

Niswender et al. 1997. Effects of increased glucokinase gene copy number on glucose homeostatis and hepatic glucose metabolism. The Journal of Biological Chemistry, 272(36):22570-22575.
Note for guidance on stability testing of existing active substances and related finished product, Committee for Proprietary Medicinal Products (CPMP), Apr. 22, 1998, 9 pp.
Novi et al. (Apr-Jun 1990) The role of opioid antagonists in the treatment of obesity. Results of a clinical trial with naltrexone, Minerva Endocrinol. 15(2):121-123, Abstract.
O'Byrne et al., Jan. 1, 1990, Effects of drugs on glucose tolerance in non-insulin-dependent diabetes (part II), Drugs, Adis International Ltd., 40(2):204-219.
Okada et al. (1992) Effects of zonisamide on extracellular levels of monoamine and its metabolite, and on Ca2+ dependent dopamine release Epilepsy Research, 13:113-119.
Okada et al. (1995) Effects of zonisamide on dopaminergic system, Epilepsy Research, 22:198-205.
Olsen et al., (1990) Conjugate Addition Ligands of Opioid Antagonists. Methacrylate Esters and Ethers of 6Alpha- And 6Beta-Naltrexol, Journal of Medicinal Chemistry, American Chemical Society, 33(2):737-741.
Olszewski et al. (Jun. 13, 2001) Evidence of Interactions Between Melanocortin and Opioid Systems in Regulation of Feeding, NeuroReport, 12(8):1727-1730.
Oommen et al. (1999) Zonisamide: A new antiepileptic drug. Clinical Neuropharmacology, 22(4):192-200.
Ortho-Novum Tablets and Modicon Tablets Prescribing Information, Apr. 2002, 8 pp.
Otake et al. (May 15, 2005) Association of visceral fat accumulation and plasma adiponectin and colorectal ademona: evidence for participation of insulin resistance, Clinical Cancer Research 11:3642-3646.
Ovadia, Oct. 1999, A Novel Twist on Binge Eating Treatment, Psychiatric Dispatches in Primary Psychiatry; 6(10):24-29.
Paar et al., 2002, Bivalent ligands with rigid double-stranded DNA spacers reveal structural constraints on signaling by FcεRI, J. Immunol., 169:856-864.
Padwal, Oct. 6, 2009, Contrave, a bupropion and naltrexone combination therapy for the potential treatment of obesity, Curr. Opin. Investig. Drugs, 10(10):1117-1125 (abstract).
Paile-Hyvarinen et al., Mar. 14, 2003, Quality of life and metabolic status in mildly depressed women with type 2 diabetes treated with paroxetine: a single blind randomised placebo controlled trial, BMC Family Practice, Biomed Central, 4(1), 6 pp.
Pandit, 2007, Introduction to the Pharmaceutical Sciences, 1st Ed., Lippincott Williams & Wilkins, Baltimore, MD, p. 154.
Pasternak et al. (1980) Long-acting opiate agonists and antagonists: 14-hydroxydihydromorphinone hydrazones, Med. Chem, 23:674-676.
Pavuluri et al. (2002) Topiramate Plus Risperidone for Controlling Weight Gain and Symptoms in Preschool Mania, Journal of Child and Adolescent Psychopharmacology, 12(3):271-273.
Penn et al., 2003, Pharmacotherapy of obesity in the near term, Current Opinion in Endocrinology and Diabetes, 18(2):311-316.
Portoghese et al., 1982, Opioid agonist and antagonist bivalent ligands as receptor probes, Life Sciences, 31:1283-1286.
Portoghese et al., 1986, Opioid agonist and antagonist bivalent ligands. The relationship between spacer length and selectivity at multiple opioid receptors, J. Med. Chem., 29:1855-1861.
Portoghese et al., 1986, Synthesis and Opioid antagonist potencies of naltrexamine bivalent ligands with conformationally restricted spacers J. Med. Chem., 29:1650-1653.
Portoghese, 1992, The role of concepts in structure-activity relationship studies of opioid ligands, J. Med. Chem., 35:1927-1937.
Potter et al., 1997, Sustained Weight Loss Associated with 12-month topiramate Therapy, Epilepsia, Raven Press Ltd. New York, 38(Suppl 8):97.
Rao et al. (1998) Fixed-does combination therapy: panacea or poison?, Intensive Care Med, 24:283-285.

Reaven, G. M. 1995. Pathophysiology of insulin resistance in human disease. Physiological Reviews, 75(3):473-486.
Reents et al. (1988) Nalozone and naltrexone, Chest, 93(1):217-219.
Remington's Pharmaceutical Sciences. 18$^{th}$ Edition; Easton, PA: Mack Publishing Co. (1990).
Reneric et al. (Nov. 1998) Opioid Receptor Antagonists in Psychiatry, CNS Drugs, 10(5):365-382.
Rezvani et al. 2000. Combination pharmacotherapy: A mixture of small doses of naltrexone, fluoxetine, and thyrotropin-releasing hormone analogue reduces alcohol intake in three strains of alcohol-preferring rats. Alcohol & Alcoholism, 35(1):76-83.
Romano et al. 2001. Long-term treatment of obsessive-compulsive disorder after an acute response: A comparison of fluoxetine versus placebo. Journal of Clinical Psychopharmacology, 21(1):46-52.
Rotzinger et al. (1999) Metabolism of some 'second' and 'fourth' generation antidepressants: iprindole, viloxazine, bupropion, mianserin, maprotiline, trazadone, nefazodone, and vaniafaxine, Cellular and Molecular Neurobiology, 19:430.
Rowland et al. (2001) Effects of the cannabinoid receptor antagonist SR 141716, alone and in combination with dexfenfluramine or naloxone, on food intake in rats. Psychopharmacology; 159:111-116.
Saba et al. 2002. Lamotrigine-clozapine combination in refractory schizophrenia: Three cases. The Journal of Neuropsychiatry and Clinical Neurosciences, 14(1):86.
Sackellares et al. (1985) Pilot study of zonisamide (1,2-benzisoxazole-3-methanesulfonamide) in patients with refractory partial seizures. Epilepsia, 26(3):206-211.
Saper et al. (2002) The need to feed: Homeostatic and hedonic control of eating, Neuron, 36:199-211.
Sashiwa et al., 2000, Chemical modification of chitosan. 3. Hyperbranched chitosan-sialic acid dendrimer hybrid with tetraethylene glycol spacer, Macromolecules, 33:6913-6915.
Sayre et al., 1984, Design and synthesis of naltrexone-derived affinity labels with nonequilibrium opioid agonist and antagonist activities. Evidence for the existence of different receptor subtypes in different tissues, J. Med. Chem., 27:1325-1335.
Scheen et al., May 1, 2005, Diabete sucre iatrogene: l'exemple des anti-phsychogiques atypiques, Revue Medicale de Liege, 60(5-6):455-460.
Schimmel et al., 1974, Inhibition by diphenylhydantoin of the diabetogenic action of streptozocin, Horm. Metab. Res. 6:475-477.
Schmidhammer et al. (1994) Mixed Azines of Naloxone with Dihydromorphinone Derivatives. A. Hely. Chim. Acta; 77:999-1002.
Schmidt et al. (1993) Zonisamide for add-on treatment of refractory partial epilepsy: a European double-blind trial. Epilepsy Research; 15:67-73.
Shapira et al. (2000) Treatment of Binge-Eating Disorder with Topiramate: A Clinical Case Series. J. Clin. Psychiatry; 61(5):368-371.
Shapira et al. 2004. A double-blind, placebo-controlled trial of olanzapine addition in fluoxetine-refractory obsessive-compulsive disorder. Biol. Psychiatry, 550:553-555.
Shapiro et al. (2005) Additive Benefits of Combination Therapy with Sibutramine and Rimonabant on Body Weight, Insulin Sensitivity and Lipoproteins in Diet-Induced Obese Mice, 2005 NAASO Annual Meeting, Poster 405-P.
Shelton (2003) Classification of Antidepressants and their Clinical Implications, Primary Care Companion J. Clin. Psychiatry, 5(Supp. 7):27-32.
Shriqui et al. (Jul. 2002) Atypical Antipsychotics, The Canadian Journal of CME, pp. 65-80.
Shuman et al., Jun. 1986, Abnormal body fat distribution detected by computed tomography in diabetic men, Investigative Radiology, 21(6):483-487.
Sitsen et al., 2001, Drug-drug interaction studies with mirtazapine and carbamazepine in healthy male subjects, European Journal of Drug Metabolism and Pharmacokinetics, 26(1-2):109-121.
Sleep Disorders, in Diagnostic and Statistical Manual of Mental Disorders, 4$^{th}$ Edition, American Psychiatric Association, p. 583-595 (2000).
Sneer et al., Protective effect of diphenylhydantoin on the diabetes-inducing effect of alioxan, database accession No. 1980:34024.

(56) References Cited

OTHER PUBLICATIONS

Spigset et al. (2001) Therapeutic Approaches to Bulimia Nervosa, Expert Opinion on Therapeutic Patents, 11(3):463-477.
Srivastava et al. 1975. Organic disulfides and related substances. 38. Some disulfide and trisulfide sulfinate salts as antiradiation drugs. Journal of Medicinal Chemistry, 18(8):798-802.
Stansfeld et al., Aug. 1992, Social class and minor psychiatric disorder in British civil servants: a validated screening survey using the General Health Questionnaire, Psychological Medicine, 22:739-749.
Steffen et al. 2006. Emerging drugs for eating disorder treatment. Expert Opin. Emerging Drugs, 11(2):315-336.
Stein (Feb. 15, 2000) Neurobiology of the obsessive-compulsive spectrum disorders, Biological Psychiatry 47(4):296-304.
Stein (Aug. 3, 2002) Obsessive-compulsive disorder, Lancet 360(9330):397-405.
Stepinski et al., 1991, Use of hydrophilic diamines for bridging of two opioid peptide pharmacophores, Internat. J. of Peptide & Protein Res., 38:588-592.
Storch et al. 2006. Clinical predictors of early fluoxetine treatment response in obsessive-compulsive disorder. Depression and Anxiety, 23:429-433.
Stromberg et al. (2002) A comparison of the effects of 6-beta naltrexol and naltrexone on the consumption of ethanol or sucrose using a limited-access procedure in rats. Pharmacology, Biochemistry, and Behavior, 72:483-490.
Swedo et al. 1998. Pediatric autoimmune neuropsychiatric disorders associated with streptococcal infections: Clinical description of the first 50 cases. Am. J. Psychiatry, 155(2):264-271.
Symons et al. 2004. Self-injurious behavior and the efficacy of naltrexone treatment: A quantitative synthesis. Mental Retardation and Developmental Disabilities Research Reviews, 10:193-200.
Tamiz et al., 2000, Application of the bivalent ligand approach to the design of novel dimeric serotonin reuptake inhibitors, J. Am. Chem. Soc., 122:5393-5394.
Tamiz et al., 2001, Pharmacological and behavioral analysis of the effects of some bivalent ligand-based monoamine reuptake inhibitors, J. Med. Chem., 44:1615-1622.
Tavakoli et al., Jul. 2003, Diabetic ketoacidosis in a patient with olanzapine, valproic acid, and venlafaxine, Southern Medical Journal, 96(7):729-730.
Testa, 2004, Prodrug research: futile or fertile?, Biochemical Pharmacology, 68:2097-2106.
Thearle et al. (2003) Obesity and Pharmacology, Endocrinology and Metabolism Clinics of North American, W.B. Suanders Company, Philadelphia US 32(4):1005-1024.
Thombre et al. (2004) Osmotic drug delivery using swellable-core technology, Journal of Controlled Release 94:75-89.
Tollefson et al. (1997) Olanzapine versus haloperidol in the treatment of schizophrenia and schizoaffective and schizophreniform disorders: results of an international collaborative trial, Am J. Psychiatry, 154(5):457-465.
Turnbull et al., Jan. 1985, The effect of valproate on blood metabolite concentrations in spontaneously diabetic, ketoacidotic, bb/e wistar rats, Diabetes Research 2(1):45-48.
Tutka et al., 2004, Convulsant and anticonvulsant effects of bupropion in mice, European Journal of Pharmacology, 499:117-120.
Van Gaal et al., Aug. 1998, Sibutramine and fat distribution: is there a role for pharmacotherapy in abdominal/visceral fat reduction?, Int J Obes Relat Metab Disord, Suppl 1:S38-40; discussion S41-2 (abstract).
Van Schaftingen et al. (1992) The regulatory protein of liver glucokinase. Advan. Enzyme Regul., 32:133-148.
Vieta et al. (2003) 1-year follow-up of patients treated with risperidone and topiramate for a manic episode, J Clin Psychiatry, 64(7):834-829.
Vieta et al. (2004) Effects on weight and outcome of long-term olanzapine-topiramate combination treatment in bipolar disorder. Journal of Clinical Psychopharmacology 24(4):374-378.
Vythilingum et al. 2005. Obsessive-compulsive disorders and dermatologic disease. Dermatologic Clinics, 23:675-680.
Wadden et al. (2000) Effects of Sibutramine Plus Orlistat in Obese Women Following 1 Year of Treatment by Sibutramine Alone: A Placebo-Controlled Trial, Obesity Research; 8(6):431.
Wadden et al., Jan. 2011, Weight loss with naltrexone SR/bupropion SR combination therapy as an adjunct to behavior modification: the COR-BMOD trial, Obesity, 19(1):110-120.
Walker et al. (1988) Chronic Toxicity of the Anticonvulsant Zonisamide in Beagle Dogs, Fundamental and Applied Toxicology 11:333-342.
Wang et al. (2002) Gabapentin augmentation therapy in bipolar depression, Bipolar Disorders 4:296-301.
Weintraub et al. (1992) Long-term Weight Control Study I (weeks 0 to 34) 'The Enhancement of Behavior Modification, Caloric Restriction, and Exercise by Fenfluramine Plus Phentermine versus Placebo', Clinical Pharmacology & Therapeutics, 51(5):586-94.
Welty et al. (Nov. 30—Dec. 5, 2001) Weight Loss Associated With Use of Zonisamide in European and US Clinical Trials, A Compendium of Posters and Platform Sessions for Zonegran®, Presented at the Annual Meeting 2001 of the American Epilepsy Society, Philadelphia, Pennsylvania.
Wermuth, Apr. 2006, Similarity in drugs: reflections on analogue design, Drug Discovery Today, 11(7/8):348-354.
Werneke et al. (2002) Options for Pharmacological Management of Obesity in patients Treated with Atypical Antipsychotics, International Clinical Psychopharmacology, 17(4):145-160.
Wheatley et al., 1998, Mirtazapine: efficacy and tolerability in comparison with fluoxetine in patients with moderate to severe major depressive disorder, J. Clin Psychiatry, 59(6):306-312, Abstract.
White et al. 2002. Development and validation of the food-craving inventory. Obesity Research, 10(2):107-114.
Wieczorek et al., 2001, The effects of the selective serotonin reuptake-inhibitor fluvoxamine on body weight in Zucker rats are mediated by cortocotrophin-releasing hormone, International Journal of Obesity, 25(10):1566-1569.
Wilcox et al., 2009, An open-label study of naltrexone and bupropion combination therapy for smoking cessation in overweight and obese subjects, Addictive Behaviors, 35(3):229-234.
Wilding (2004) Clinical evaluation of anti-obesity drugs. Current Drug Targets; 5:325-332.
Willmore, L. J. 2004. Commentary on Leppik. Seizure, 13S:S10.
Wilner, 2002, Is Weight Loss With Zonisamide Gender-Specific?, Annual Meeting of the American Epilepsy Society, https://secure.neurohub.net/cgi-perl/get.cgi?pub=52318&ext=htm, 1 pp.
Wolff (1995) Burger's Medicinal Chemistry and Drug Discovery, John Wiley & Sons, 5th Ed. 1:975-977.
Yeomans et al. (2002) Opioid peptides and the control of human ingestive behaviour, Neuroscience and Biobehavioral Reviews, 26:712-728.
Yoshimasu et al. (2003) Psychotropic Drug-Induced Obesity, Nippon Rinsho, 61(Suppl. 6):825-829. (English translation of Japanese Office Action containing Examiner's characterization of reference is appended to reference: Notice of Reasons for Rejection, Application No. 2006-549530).
Yu et al. (2005) Influence of insulin treatment on insulin sensitivity in insulin requiring type 2 diabetes patents, Diabetes Research and Clinical Practice, 68S1:S54-S59.
Zeng et al., 1988, Convenient synthesis of 9-alkyl and 9-arylacridines from [2-(trimethylsilyl)ethoxy]methyl (sem) protected acridone, Tetrahedron Letters, 29(40):5123-5124.
Zhang et al. (1994) Positional Cloning of the Mouse obese gen and its humane homologue, Nature, 372:425-432.
Zhu et al. (Apr. 3, 2002) Pharmacologic Treatment of Eating Disorders, Canadian Journal of Psychiatry, 47(3):227-234.
Zitterl et al. 1999. Efficacy of fluoxetine in Austrian patients with obsessive-compulsive disorder. Wiener Klinische Wochenschrift, 111(11):439-442.
Zohar et al. 1987. Serotonergic responsivity in obsessive-compulsive disorder. Arch. Gen. Psychiatry, 44:946-951.
Zonisamide (Oral Route), MayoClinic.com, 12 pp., 2009.
ISR and WO for PCT/US07/013030, dated Apr. 3, 2008.

(56) References Cited

OTHER PUBLICATIONS

A multicenter, randomized, double-blind, placebo-controlled study assessing the occurrence of major adverse cardiovascular events (MACE) in overweight and obese subjects with cardiovascular risk factors receiving naltrexone SR/bupropion SR, Adis Clinical Trials Insight (Nov. 15, 2011), 5 pp.
Bakris et al., 2002, Orlistat improves blood pressure and control in obese subjects with treated but inadequately controlled hypertension, Journal of Hypertension, 20(11):2257-2267.
Eckel et al., Apr. 16, 2005, The metabolic syndrome, The Lancet 365:1415-1428.
Ioannides-Demos et al., 2005, Pharmacotherapy for obesity, Drugs, 65(10):1391-1418.
Klein et al., Jun. 1, 2009, Naltrexone plus bupropion combination causes significant weight loss without worsening psychiatric symptoms, Diabetes, 58(Suppl. 1):A444.
Ludman et al., "Does depression reduce the effectiveness of behavioral weight loss treatment?" Behav Med. 2010; 35(4):126-134.
McElroy et al., Jun. 1, 2010, An open-label study evaluating the naltrexone SR/bupropion SR combination therapy in overweight or obese subjects with major depression, Diabetes, 59(Suppl. 1):A483.
Orexigen Therapeutics, Inc., A safety and efficacy study comparing naltrexone SR/bupropion SR and placebo in obese type 2 diabetics, http://clinicaltrials.gov/ct2/show/NCT00474630, 4 pp. Apr. 31, 2008.
Orexigen Therapeutics, Inc., Method-of-use study assessing the effect of naltrexone sustained release (SR)/bupropion SR on body weight and cardiovascular risk factors in overweight and obese subjects, http://clinicaltrials.gov/ct2/show/NCT01764386, 5 pp. Feb. 9, 2013.
Pagoto et al., Association of Major Depression and Binge Eating Disorder with Weight Loss in a Clinical Setting, Obesity, Nov. 2007; 15(11):2557-2559.
Plodkowski et al., 2009, Bupropion and naltrexone: a review of their use individually and in combination for the treatment of obesity, Expert Opin. Pharmacother. 10(6):1069-1081.
Brown et al., 2012, Current and emerging directions in the treatment of eating disorders, Substance Abuse: Research and Treatment, 6:33-61.
Brunk, Sep. 1, 2009, Significant weight loss shown with naltrexone/bupropion combo, Thoracic Surgery News, http://www.thoracicsurgerynews.com/?id=95937&tx_ttnews[tt_news]=86987& cHash=a97b7f3c0f6a8c6a3b3ca96df9a6b73f, 1 pp.
Chakraborty et al., 2010, Management of anorexia and bulimia nervosa: an evidence-based review, Indian J Psychiatry, 52:174-186.
Clinical Trials.gov, Jul. 13, 2009, An open-label study assessing the safety and efficacy of naltrexone sustained release (SR)/bupropion sustained release (SR) in overweight or obese subjects with major depression, 2 pp.
Glod et al., Jul.-Sep. 2003, Open trial of bupropion sr in adolescent major depression, J Child Adolesc Psychiatr Nurs, 16(3):123-130.
McElroy et al., Jun. 2013, Naltrexone/bupropion combination therapy in overweight or obese patients with major depressive disorder: results of a pilot study, Prim Care Companion CNS Disord, 15(3), 17 pp.
McElroy et al., May 7, 2012, Pharmacological management of binge-eating disorder: current and emerging treatment options, Therapeutics and Clinical Risk Management, 8:219-241.
Milano et al., May-Jun. 2005, Treatment of bulimia nervosa with fluvoxamine: a randomized controlled trial, Advances in Therapy, 22(3):278-283.
Pearlstein et al., 2003, A double-blind, placebo-controlled trial of fluvoxamine in binge eating disorder; a high placebo response, Arch Womens Ment Health, 6:147-151.
Ricca et al., 2001, Fluoxetine and fluvoxamine combined with individual cognitive-behavior therapy in binge-eating disorder: a one-year follow-up study, Psychotherapy and Psychosomatics, 70:298-306.
Altomonte et al., 1988, Effect of fenfluramine on insulin/growth hormone ratio in obese subjects, Pharmacology, 36(2):106-111.
Bengtsson, 1993, The consequences of growth hormone deficiency in adults, Acta Endocrinol. (Copenh.), 128(Suppl 2):2-5.
Carson et al., May 1996, Pilot study of the use of naltrexone to treat the severe pruritis of cholestatic liver disease, Amer. J. Gastroenterology, 91(5):1022-1023.
Clinical Trials.gov, A Multicenter, randomized, double-blind, placebo-controlled study assessing the occurrence of major adverse cardiovascular events (MACE) such as cardiovascular death, non-fatal myocardial infarction, and non-fatal stroke in overweight and obese subjects who are at a higher risk of having these events because they ahv diabetes and/or other cardiovascular risk factors, NTC01601704, May 7, 2013, 4 pp.
Das et al., 2003, Controlled-release of oral dosage forms, Formulation, Fill & Finish, pp. 10-16.
De Boer et al., 1995, Clinical aspects of growth hormone deficiency in adults, Endocrine Reviews, 16(1):6386.
Eid et al., 2005, Effective treatment of polycystic ovarian syndrome with roux-en-y gastric bypass, Surgery for Obesity and Related Diseases, 1:77-80.
Ghisoli et al., 1980, Effects of dopaminergic receptor stimulation and opioid receptor blockade on GH incretion: preliminary findings, Boll. Soc. Ital. Biol. Sper., 56(12):1222-1225.
Ghisoli et al., 1980, Effects of interaction between 2-Br-α-ergocryptine (CB 154) and naloxone on the control of insulin secretion in normal man, Boll. Soc. Ital. Biol. Sper., 56(12):1215-1221.
Goodman & Gillman's, The Pharmacological Basis of Therapeutics, 10th Ed., Edited by J. Hardman and L. Limbird, 2001, p. 6.
Gudmundur et al., 1997, Growth hormone treatment of abdominally obese men reduces abdominal fat mass, improves glucose and lipoprotein metabolism, and reduces diastolic blood pressure, J. Clin. Endocrin. And Metab., 82(3):727-734.
Guidance for Industry Estimating the Maximum Safe Starting Dose in Initial Clinical Trials for Therapeutics in Adult Healthy Volunteers, U.S. Department of Health and Human Services, U.S. Food and Drug Administration Center for Drug Evaluation and Research (CDER), Pharmacology and Toxicology, Jul. 2005.
Herper, Mar. 5, 2015, Top Fda Official Says Orexigen Study Result 'Unreliable,' 'Misleading, http://www/forbes.com/sites/matthewherper/, 4 pp.
Hollander et al., Oct. 21, 2013, Effects of naltrexone sustained-release/bupropion sustained release combination therapy on body weight and glycemic parameters in overweight and obese patients with type 2 diabetes, Diabetes Care, 36(12):4022-4029.
Husten, Mar. 3, 2015, Orexigen Released Interim Data Without Approval of Trial Leaders, http://ww/forbes.com/sites/harryhusten, 6 pp.
Laessle et al., May 1997, A comparison of resting metabolic rate, self-rated food intake, growth hormone, and insulin levels in obese and nonobese preadolescents, Physiol. Behav., 61(5):725-729.
Meyer et al., Sep. 1984, Bioequivalence, dose-proportionality, and pharmacokinetics of naltrexone after oral administration, J. Clin. Psychiatry, 45(9)(Sec. 2):15-19.
Oncken et al., 2001, Adverse effects of Oral naltrexone: an analysis of data from two clinical trials, Psychopharmacology, 154:397-402.
Patel et al., Jun. 2011, a hospital-based observational study of type 2 diabetic subjects from Gujarat, India, Journal of Health, Population and Nutrition, 29(3):265-272.
Ramlo-Halsted et al., 2000, The natural history of type 2 diabetes: practical points to consider in developing prevention and treatment strategies, Clin. Diabetes, 18(2).
Rao, Mar. 2001, Insulin resistance syndrome, American Family Physician, 63(6):1159-1163.
Remington's Pharmaceutical Sciences, 1980, 16th ed., Mack Publishing Company, Arthur Osol. Editor, pp. 1553-1594.
Remington's Pharmaceutical Sciences, 1980, 16th ed., Mack Publishing Company, Arthur Osol. Editor, pp. 1592-1597.
Richelsen et al., Feb. 1994, Growth hormone treatment of obese women for 5 wk: effect on body composition and adipose tissue LPL activity, Am J. Physiol., 266(2 Pt 1):11-16.
Stedman's Medical Dictionary, 28th ed., Lippincott Williams & Wilkins, Philadelphia, 1999, pp. 490-491 and 1552.
Tallarida, 2001, Drug synergism: its detection and applications, J. Pharmacol. And Expt. Therap., 298(3):865-872.

(56) References Cited

OTHER PUBLICATIONS

Wellbutrin® (bupropion hydrochloride) tablets, in Physicians' Desk Reference, 49th edition, 1995, pp. 824-827,150.
White et al., 2003, Clarifying the role of insulin in type 2 diabetes management, Clinical Diabetes, 21(1):1421.
Wong et al., Aug. 2004, Starting insulin treatment in type 2 diabetes, Australian Prescriber, 27(4):93-96.
Cleveland Clinic Press Release: "Clinical Trial Testing Safety of Obesity Drug Contrave Halted; 50 Percent Interim Data Released by the Study's Executive Committee", May 12, 2015, retrieved from http://my.clevelandclinic.org/about-cleveland-clinic/newsroom/releases-videos-newsletters/2015-5-12-clinical-trial-testing-safety-of-obesity-drug-contrave-halted.
Orexigen Therapeutics Press Release: "Orexigen Therapeutics Provides Statement on Termination of the Light Study and Updates on Contrave Collaboration with Takeda Pharmaceuticals", May 12, 2015, retrieved from http://ir.orexigen.com/phoenix.zhtml?c=207034&p=irol-newsArticle_Print&ID=2047312.
Orexigen Therapeutics Press Release: "Takeda Pharmaceuticals and Orexigen Therapeutics Announce Termination of the Cardiovascular Outcomes Study (Light Study) of the Obesity Drug Contrave® (naltrexone HCI and bupropion HCI)", May 12, 2015, retrieved from http://ir.orexigen.com/phoenix.zhtml?c=207034&p=irol-newsArticle_Print&ID=2046959.
Herper, "Heart Benefit for Orexigen Drug Nearly Vanishes with New Data", Forbes, May 12, 2015, retrieved from http://www.forbes.com/sites/matthewherper/2015/05/12/heart-benefit-for-orexigen-drug-nearlyvanishes-with-new-data/.
Herper, "A Top Cardiologist Says a Diet Drug Maker Misled Patients and Investors", Forbes, May 12, 2015, retrieved from http://www.forbes.com/sites/matthewherper/2015/05/12/a-top-cardiologist-says-a-diet-drugmaker-misled-patients-and-investors/#.
Mukherjee, "Update: Takeda threatens to break off Orexigen collab after Contrave data drama", BioPharmaDive, May 12, 2015, retrieved from http://www.biopharmadive.com/news/update-takedathreatens-to-break-off-orexigen-collab-after-contrave-data-d/396940/.

* cited by examiner

SUSTAINED RELEASE FORMULATION OF NALTREXONE

RELATED APPLICATION INFORMATION

The present application is a continuation of U.S. application Ser. No. 11/757,773, filed Jun. 4, 2007, now U.S. Pat. No. 8,916,195, which claims the benefit of priority to U.S. Provisional Patent Application Ser. No. 60/811,251, filed Jun. 5, 2006, and U.S. Provisional Patent Application Ser. No. 60/841,114, filed Aug. 29, 2006, all of which are hereby incorporated by reference in their entireties.

BACKGROUND OF THE INVENTION

1. Field of the Invention

The present invention relates to pharmaceutical compositions comprising sustained-release opioid receptor antagonists and methods of administration and use thereof

2. Description of the Related Art

Obesity is a major health concern in Western societies. It is estimated that about 97 million adults in the United States are overweight or obese. Epidemiological studies have shown that increasing degrees of overweight and obesity are important predictors of decreased life expectancy. Obesity causes or exacerbates many health problems, both independently and in association with other diseases. The medical problems associated with obesity, which can be serious and life-threatening, include hypertension; type 2 diabetes mellitus; elevated plasma insulin concentrations; insulin resistance; dyslipidemias; hyperlipidemia; endometrial, breast, prostate and colon cancer; osteoarthritis; respiratory complications, such as obstructive sleep apnea; cholelithiasis; gallstones; arteriosclerosis; heart disease; abnormal heart rhythms; and heart arrythmias (Kopelman, P. G., Nature 404, 635-643 (2000)). Obesity is further associated with premature death and with a significant increase in mortality and morbidity from stroke, myocardial infarction, congestive heart failure, coronary heart disease, and sudden death.

Obesity is often treated by encouraging patients to lose weight by reducing their food intake or by increasing their exercise level and therefore increasing their energy output. A sustained weight loss of 5% to 10% of body weight has been shown to improve the co-morbidities associated with obesity, such as diabetes and hypertension, and can lead to improvement of obesity-related conditions such as osteoarthritis, sleep apnea and pulmonary and cardiac dysfunction.

Naltrexone, having the chemical name (17-(cyclopropylmethyl)-4,5α-epoxy-3,14-dihydroxymorphinan-6-one) and the chemical structure shown below, is an opioid receptor antagonist used primarily in the management of alcohol dependence and opioid dependence.

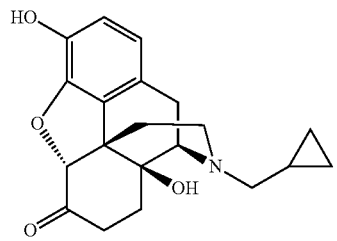 [SMILES: O=C1CC[C@@]2(O)[C@H]3Cc4ccc(O)c5c4[C@@]2(CCN3CC2CC2)[C@H]1O5]

Naltrexone for oral administration has been commercially available for a number of years from various sources as the hydrochloride salt, naltrexone hydrochloride, e.g., under the trade names REVIA™ (50 mg) and DEPADE™ (25 mg, 50 mg and 100 mg). The currently approved forms of oral naltrexone are immediate release formulations that are efficacious even when dosed as infrequently as once every 72 hours. For example, the label of the DEPADE® brand of naltrexone hydrochloride indicates that naltrexone is a potent opioid antagonist with a prolonged pharmacological effect (24 to 72 hours) and recommends a dose of 50 mg once daily. The DEPADE® label discloses that clinical studies indicate that 50 mg of naltrexone hydrochloride will block the pharmacologic effects of 25 mg of intravenously administered heroin for periods as long as 24 hours. The DEPADE® label goes on to indicate that other data suggest that doubling the dose of naltrexone hydrochloride provides blockade for 48 hours, and tripling the dose of naltrexone hydrochloride provides blockade for about 72 hours. Thus, despite reaching a peak serum concentration quickly ($T_{max}$ of approximately 1 hour) after oral administration, the immediate release form of naltrexone has relatively long lasting effects.

The long-lasting effects of the immediate release form of oral naltrexone may be used to encourage patient compliance by utilizing a dosing frequency that is less than once per day, e.g. every other day or every three days. For example, the DEPADE® label indicates that a flexible approach to a dosing regimen may be employed to enhance compliance. Thus, the DEPADE® label discloses, patients may receive 50 mg of naltrexone hydrochloride every weekday with a 100 mg dose on Saturday or patients may receive 100 mg every other day, or 150 mg every third day. The DEPADE® label refers to clinical studies reported in the literature that have employed the following dosing regimen: 100 mg on Monday, 100 mg on Wednesday, and 150 mg on Friday. Thus, use of the immediate release oral form allows a patient to take a relatively large dose of naltrexone at a time when the temptation to abuse alcohol or opioids may be less (e.g., during the week), with the effects lasting to a time when temptation may be greater (e.g., over the weekend).

The DEPADE® label indicates that naltrexone has not been shown to cause significant increases in complaints in placebo-controlled trials in patients known to be free of opioids for more than 7 to 10 days. Although a subset of the patient population reports nausea upon initial administration of 25 mg or 50 mg dosages of the immediate release oral form of naltrexone, the nausea often subsides as those patients develop a tolerance. The DEPADE® label indicates that, in an open label safety study with approximately 570 individuals with alcoholism receiving naltrexone, the following new-onset adverse reactions occurred in 2% or more of the patients: nausea (10%), headache (7%), dizziness (4%), nervousness (4%), fatigue (4%), insomnia (3%), vomiting (3%), anxiety (2%) and somnolence (2%). Moderate to severe nausea was reported by 18 patients (15%) in a 10-week open label study of naltrexone among alcohol dependent participants, involving a initial 25 mg dose followed by a dose of 50 mg daily for 10 weeks (O'Malley, S. S. J. Clin. Psychopharmacol. 2000 February; 20(1):69-76). Eight of the eighteen patients that experienced moderate to severe nausea discontinued treatment, nausea resolved within one week for five subjects and within two weeks for four, and it continued off and on throughout the ten-week period for one subject. The authors linked the moderate to severe nausea to poorer medication compliance and heavier drinking by the patients during treatment.

It appears that while some patients experience adverse effects upon administration of 25 mg or 50 mg dosages of immediate release oral naltrexone, the adverse effects often subside within a relatively short period of time and many patients are able to tolerate significantly higher oral dosages, e.g., 100 mg or 150 mg. A once-monthly injectable form of naltrexone is commercially available under the tradename VIVITROL® for the treatment of alcoholism. The prescribing information for VIVITROL® indicates that patients should be advised that they may experience nausea following the initial injection of the VIVITROL® naltrexone; that these episodes of nausea tend to be mild and subside within a few days post-injection, and that patients are less likely to experience nausea in subsequent injections.

U.S. Patent Publication No. 2004/0254208 A1 discloses the use of naltrexone in combination with other compounds for affecting weight loss, but does not disclose any particular adverse effects associated with the combinations.

SUMMARY OF THE INVENTION

An unexpectedly high incidence of adverse effects associated with co-administration of naltrexone with bupropion and/or fluoxetine has now been identified as a problem. For example, during a clinical trial described in greater detail below, the incidence of adverse events of moderate severity associated with co-administration of immediate-release naltrexone with bupropion was 30.7%. This incidence of adverse effects was significantly higher than would be expected based on the typical incidence of adverse effects associated with administration of immediate-release naltrexone alone or bupropion alone.

In an embodiment, sustained release naltrexone formulations have now been developed that provide a solution to this problem.

An embodiment provides an oral dosage form, comprising a sustained-release naltrexone formulation that is formulated to provide a reduction in at least one adverse effect, wherein the adverse effect is associated with co-administration of an immediate-release naltrexone formulation and a second compound. In an embodiment, the second compound comprises a monoamine reuptake inhibitor, such as bupropion or fluoxetine. Another embodiment provides a method of administering naltrexone, comprising administering a sustained-release naltrexone formulation to a subject, e.g., in a manner that is effective to cause weight loss and/or inhibit weight gain.

Another embodiment provides an oral unit dosage form, comprising a sustained-release naltrexone formulation that is effective to provide, after administration, an in vivo plasma concentration profile comprising at least one selected from:
   (a) a naltrexone $C_{max}$ that is about 80% or less of the naltrexone $C_{max}$ of REVIA™ immediate-release naltrexone hydrochloride, and a naltrexone $AUC_{last}$ that is in the range of about 80% to about 125% of the naltrexone $AUC_{last}$ of REVIA™ immediate-release naltrexone hydrochloride; and
   (b) a 6-beta naltrexol $C_{max}$ that is about 80% or less of the 6-beta naltrexol $C_{max}$ of REVIA™ immediate-release naltrexone hydrochloride, and a 6-beta naltrexol $AUC_{last}$ that is in the range of about 80% to about 125% of the 6-beta naltrexol $AUC_{last}$ of REVIA™ immediate-release naltrexone hydrochloride.

Another embodiment provides an oral dosage form, comprising naltrexone or a pharmaceutically acceptable salt thereof and a sustained-release carrier composition, wherein the oral dosage form provides an in vitro release rate of the naltrexone or pharmaceutically acceptable salt thereof of less than about 90% in about 4 hours.

Another embodiment provides a method of administering a sustained-release naltrexone formulation as described herein.

For example, an embodiment provides a method of administering naltrexone, comprising administering a sustained-release naltrexone formulation to a subject in an amount that is effective to provide an in vivo plasma concentration profile comprising at least one selected from:
   (a) a naltrexone $C_{max}$ that is about 80% or less of the naltrexone $C_{max}$ of REVIA™ immediate-release naltrexone hydrochloride, and a naltrexone $AUC_{last}$ that is in the range of about 80% to about 125% of the naltrexone $AUC_{last}$ of REVIA™ immediate-release naltrexone hydrochloride; and
   (b) a 6-beta naltrexol $C_{max}$ that is about 80% or less of the 6-beta naltrexol $C_{max}$ of REVIA™ immediate-release naltrexone hydrochloride, and a 6-beta naltrexol $AUC_{last}$ that is in the range of about 80% to about 125% of the 6-beta naltrexol $AUC_{last}$ of REVIA™ immediate-release naltrexone hydrochloride.

In an embodiment, a sustained-release naltrexone formulation as described herein is administered to a subject in a manner that is effective to treat a weight related condition, e.g., to cause weight loss and/or inhibit weight gain.

These and other embodiments are described in greater detail below.

DETAILED DESCRIPTION OF THE PREFERRED EMBODIMENTS

Figure 1:
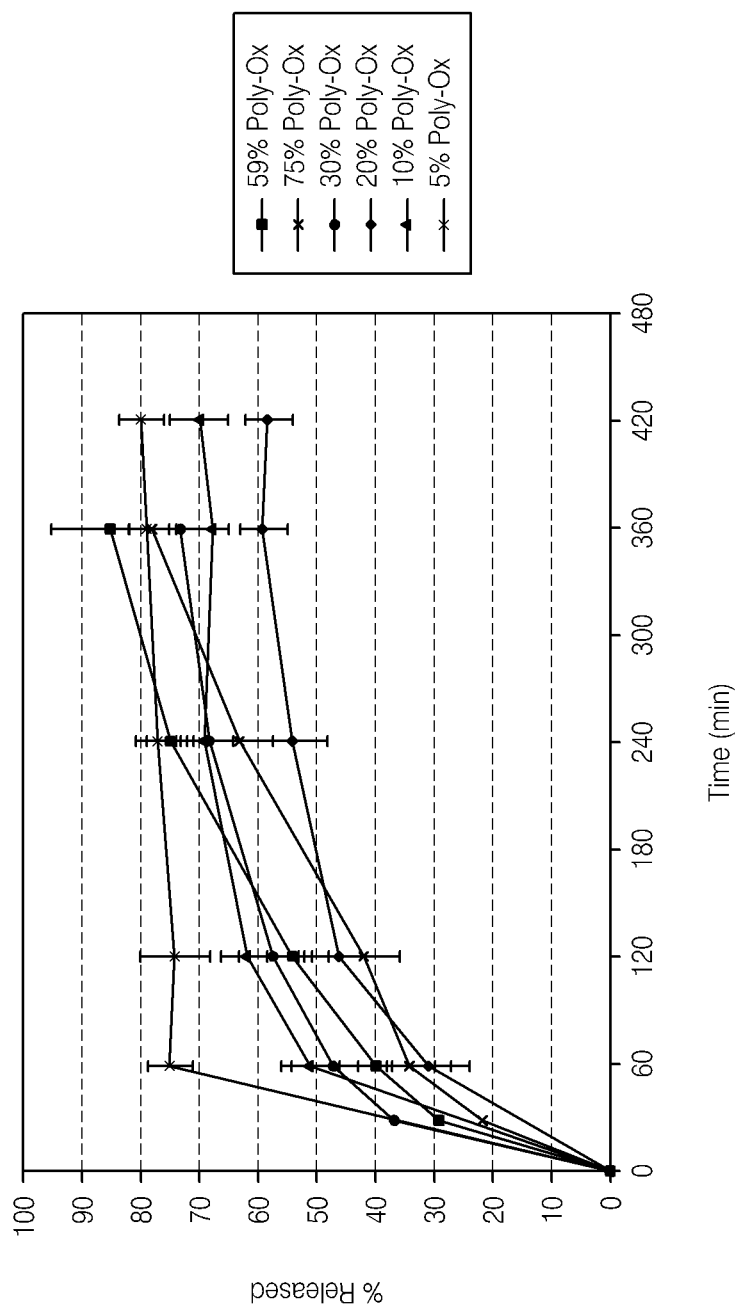
FIG. 1 shows the dissolution profile of sustained release 5 mg naltrexone tablets containing polyethylene oxide.

Various embodiments provide an oral dosage form that comprises a sustained-release naltrexone formulation. Co-administration of a sustained-release naltrexone formulation with a second compound may provide a reduction in at least one adverse effect as compared to co-administration of an immediate-release naltrexone formulation with the second compound. The second compound may be an monoamine reuptake inhibitor, such as bupropion or a pharmaceutically acceptable salt thereof or fluoxetine or a pharmaceutically acceptable salt thereof. The at least one adverse effect may include nausea.

A sustained-release naltrexone formulation may provide a naltrexone $C_{max}$ and/or a 6-beta naltrexol $C_{max}$ that is about 80% or less of the naltrexone $C_{max}$ and/or the 6-beta naltrexol $C_{max}$ of REVIA™ immediate-release naltrexone hydrochloride. A sustained-release naltrexone formulation may provide a naltrexone $AUC_{last}$ and/or a 6-beta naltrexol $AUC_{last}$ that is in the range of about 80% to about 125% of the naltrexone $AUC_{last}$ and/or the 6-beta naltrexol $AUC_{last}$ of REVIA™ immediate-release naltrexone hydrochloride.

Definitions

The term "naltrexone" may be used in a general way herein to refer to a free base of naltrexone, a pharmaceutically acceptable naltrexone salt (including hydrates and anhydrous forms, e.g., naltrexone hydrochloride dihydrate and anhydrous naltrexone hydrochloride), a naltrexone metabolite, a naltrexone isomer, a naltrexone prodrug or mixtures thereof. Reference herein to "naltrexone" will be understood as encompassing all such forms, unless the context clearly indicates otherwise.

The term "pharmaceutically acceptable salt" refers to a formulation of a compound that does not cause significant irritation to an organism to which it is administered and does not abrogate the biological activity and properties of the compound. Pharmaceutical salts of basic compounds can be obtained by reacting the compound with an acid such as hydrochloric acid, hydrobromic acid, sulfuric acid, nitric acid, phosphoric acid, methanesulfonic acid, ethanesulfonic acid, p-toluenesulfonic acid, salicylic acid and the like. For example, naltrexone hydrochloride is a pharmaceutically acceptable salt of naltrexone. Pharmaceutical salts of acidic compounds can be obtained by reacting the compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts thereof with amino acids such as arginine, lysine, and the like.

The term "oral dosage form", as used herein, has its ordinary meaning as understood by those skilled in the art and thus includes, by way of non-limiting example, a formulation of a drug or drugs in a form administrable to a human. The illustrative embodiments of the invention have been described primarily as being directed to oral dosage forms such as tablets, cores, capsules, caplets and loose powder, but other suitable dosage forms such as solutions and suspensions are also contemplated.

The term "sustained release", as used herein, has its ordinary meaning as understood by those skilled in the art and thus includes, by way of non-limiting example, the controlled release of a drug from a dosage form over an extended period of time. For example, in some embodiments, sustained-release dosage forms are those that have a release rate that is substantially longer than that of a comparable immediate release form, e.g., greater than 125% of the release rate of an immediate-release dosage form.

The term "immediate release", as used herein, has its ordinary meaning as understood by those skilled in the art and thus includes, by way of non-limiting example, release of a drug from a dosage form in a relatively brief period of time after administration. Examples of immediate-release dosage forms of naltrexone hydrochloride include REVIA™ immediate-release naltrexone hydrochloride and DEPADE™ immediate-release naltrexone hydrochloride. In some embodiments, immediate-release dosage forms are those that have a release rate that is up to and including 125% of the release rate for one or more of REVIA™ immediate-release naltrexone hydrochloride and DEPADE™ immediate-release naltrexone hydrochloride. The REVIA™ immediate-release naltrexone hydrochloride may be a 50 mg dosage form. The DEPADE™ immediate-release naltrexone hydrochloride may be a 25 mg, 50 mg or 100 mg dosage form. As used herein, an immediate-release formulation may refer to REVIA™ immediate-release naltrexone hydrochloride. In some embodiments, the dosage of the immediate-release formulation is substantially the same as a sustained-release dosage form described herein, while in other embodiments it is not.

The term "release rate", as used herein, has its ordinary meaning as understood by those skilled in the art and thus includes, by way of non-limiting example, a characteristic related to the amount of an active ingredient released per unit time as defined by in vitro or in vivo testing. An in vitro release rate is determined by a "standard dissolution test," conducted according to United States Pharmacopeia 24th edition (2000) (USP 24), pp. 1941-1943, using Apparatus 2 described therein at a spindle rotation speed of 100 rpm and a dissolution medium of water, at 37° C., or other test conditions substantially equivalent thereto.

The term "pharmacokinetic profile," as used herein, has its ordinary meaning as understood by those skilled in the art and thus includes, by way of non-limiting example, a characteristic of the curve that results from plotting blood serum concentration of a drug over time, following administration of the drug to a subject. A pharmacokinetic profile thus includes a pharmacokinetic parameter or set of parameters that can be used to characterize the pharmacokinetics of a particular drug or dosage form when administered to a suitable patient population. Various pharmacokinetic parameters are known to those skilled in the art, including area under the blood plasma concentration vs. time curve (AUC) and maximum blood plasma concentration after administration ($C_{max}$). $AUC_{last}$ indicates the area under the blood plasma concentration vs. time curve from the time of administration until the time of the last measurable concentration. Pharmacokinetic parameters may be measured in various ways known to those skilled in the art, e.g., single dosage or steady-state. Differences in one or more of the pharmacokinetic profiles (e.g., $C_{max}$) may indicate pharmacokinetic distinctness between two formulations.

Those skilled in the art will understand that pharmacokinetic parameters may be determined by comparison to a reference standard using clinical trial methods known and accepted by those skilled in the art, e.g., as described in the examples set forth herein. Since the pharmacokinetics of a drug can vary from patient to patient, such clinical trials generally involve multiple patients and appropriate statistical analyses of the resulting data (typically ANOVA at 90% confidence). Comparisons of pharmacokinetic parameters are on a dose-adjusted basis, as understood by those skilled in the art.

In various embodiments related to the sustained-release naltrexone formulations described herein, the reference standard is an immediate-release naltrexone formulation. Those skilled in the art will understand that an immediate-release naltrexone formulation appropriate for use as the reference standard in the determination of pharmacokinetic parameters is the legend immediate-release naltrexone formulation, widely available commercially as the REVIA® brand of naltrexone hydrochloride, or an immediate-release naltrexone formulation that is formulated to have a pharmacokinetic profile that is substantially similar to the REVIA® brand of naltrexone hydrochloride. The U.S. government regulates the manner in which prescription drugs can be labeled and thus reference herein to the REVIA® brand of naltrexone hydrochloride has a well-known, fixed and definite meaning to those skilled in the art.

Co-Administration of Naltrexone and a Second Compound

In some embodiments, it is recognized that co-administration of immediate-release naltrexone with a second compound may be associated with at least one adverse effect. The at least one adverse effect may be of greater severity, duration and/or probability of occurrence than expected by separate administration of the immediate-release naltrexone and of the second compound. In some embodiments, it is thought that the second compound can potentiate naltrexone-induced effects in the chemoreceptor trigger zone (CTZ) and/or the vomiting center, thereby potentiating an adverse effect associated with administration of naltrexone. While the adverse effect may generally be characterized as tolerable when immediate-release naltrexone is administered alone, the potentiated adverse effect may be characterized as less tolerable.

Co-administration of sustained-release naltrexone with the second compound may provide a reduction in at least one adverse effect as compared to the co-administration of immediate-release naltrexone with the second compound. The reduction may include a decrease in the severity, duration and/or probability of occurrence of the at least one adverse effect. In some cases, e.g., involving individual patients, such reductions may be in comparison to the adverse effects that would be expected by one of skill in the art in view of the known side effects of a immediate release form, and thus it is not necessary that the patient actually experience side effects from the immediate release form in order to benefit from such reductions in adverse effects. While not wishing to be bound to any particular theory, the reduction in the at least one adverse effect may be a result of a lower peak blood concentration of naltrexone or a metabolite thereof associated with the administration of sustained-release naltrexone as compared to that associated with the administration of immediate-release naltrexone. A sustained-release form of naltrexone with dissolution over a longer period may provide reduced excitation, antagonism and/or inhibition to the chemoreceptor trigger zone and vomiting center (VC) in the area postrema of the brain. Further, sustained-release oral dosage forms may result in a lower concentration available to be taken up by stomach opioid receptors.

In some embodiments, the at least one adverse effect is primarily associated with administration of the second compound. Co-administration of sustained-release naltrexone can reduce the at least one adverse effect. In other embodiments, the at least one adverse effect is primarily associated with administration of the immediate-release naltrexone. Sustained-release naltrexone can provide a reduction in the at least one adverse effect as compared to the immediate-release formulation, and the sustained-release naltrexone may then be co-administered with the second compound. In still other embodiments, the at least one adverse effect is primarily associated with the combination of the second compound and the immediate-release naltrexone. The type of adverse effect associated with the combination may be one that is also associated with the administration of naltrexone alone and/or by the administration of the second compound alone. The severity, duration and/or probability of occurrence of the adverse effect may be greater when immediate-release naltrexone is co-administered with the second compound than would be expected from the separate administrations of immediate-release naltrexone and of the second compound. Co-administration of sustained-release naltrexone and the second compound can provide a reduction in the at least one adverse effect as compared to the co-administration of immediate-release naltrexone and the second compound.

The immediate-release naltrexone may comprise REVIA™ immediate-release naltrexone hydrochloride. The dosage of naltrexone in the immediate-release naltrexone may be substantially similar to that in the sustained-release naltrexone. In an embodiment, the immediate-release naltrexone is one that is substantially free of a sustained-release carrier composition.

The second compound may include an antidepressant. The second compound may include a monoamine reuptake inhibitor and/or a monoamine modulator. The monoamine may include norepinephrine, dopamine and/or serotonin. The second compound may include a dopamine reuptake inhibitor and/or a dopamine modulator. Dopamine modulation may be an effect of serotonin modulation. The second compound may include a selective serotonin reuptake inhibitor and/or a serotonin modulator. The second compound may include a compound that acts on the chemoreceptor trigger zone (CTZ) and/or the vomiting center in the lateral medullary reticular formation. The second compound may include bupropion or a pharmaceutically acceptable salt thereof and/or fluoxetine or a pharmaceutically acceptable salt thereof. The pharmaceutically acceptable salt may comprise a hydrochloride salt. The second compound may be a sustained release formulation.

The sustained-release naltrexone may be provided in an oral dosage form. In some embodiments, the oral dosage form also includes the second compound, while in other embodiments, it does not.

Co-administration of immediate-release naltrexone or sustained-release naltrexone with the second compound may include administering an oral dosage form comprising both the naltrexone and the second compound. The co-administration may include administering the naltrexone and the second compound separately but at substantially the same time. The co-administration may include administering the naltrexone and the second compound at different times (e.g., at different dosing schedules), but such that blood plasma simultaneously includes naltrexone or a naltrexone metabolite concentrations above a first threshold and concentrations for the second compound or for metabolites of the second compound above a second threshold. These thresholds may be the minimum detectable level (e.g., zero). This latter co-administration may be appropriate, for example, if the in vivo $T_{max}$ or the dissolution rate of the naltrexone formulation is substantially different from that of the second compound.

The at least one adverse effect may include an effect associated with the chemoreceptor trigger zone (CTZ) and/or the vomiting center. In some embodiments, the at least one adverse effect includes one or more of nausea, retching, dizziness, stomach upset, vertigo and vomiting. The at least one adverse effect may include one or more of anxiety, nervousness, headache, sleeping trouble, sneezing, nasal stuffiness, muscle pain, decreased sexual function or desire, blurred vision, thirst, ringing in the ears, weakness, tiredness, skin rash, confusion, mood changes, hallucinations, severe diarrhea, and breathing trouble.

The at least one adverse effect may be associated with a weight-loss treatment. The weight-loss treatment may comprise, for example, administration of one or more of an atypical antipsychotic, an antidepressant, a monoamine reuptake inhibitor, a monoamine modulator, a norepinephrine reuptake inhibitor, a dopamine reuptake inhibitor, and/or a nicotinic antagonist. The weight-loss treatment may comprise administration of bupropion or a pharmaceutically acceptable salt thereof and/or fluoxetine or a pharmaceutically acceptable salt thereof. The weight-loss treatment may comprise administration of naltrexone. In some embodiments, a sustained-release naltrexone dosage form results in the reduction of one or more adverse effects attributed, partially or wholly, to one or more non-naltrexone active ingredients of a weight-loss treatment. In some embodiments, a sustained-release naltrexone dosage form results in the reduction of one or more adverse effects attributed, partially or wholly, to a naltrexone active ingredients of a weight-loss treatment.

Pharmacokinetic Profile of Sustained-Release Naltrexone Formulations

In some embodiments, a sustained-release naltrexone formulation provides a pharmacokinetic profile that is pharmacokinetically distinct from an immediate-release naltrexone formulation (e.g., REVIA™ immediate-release naltrexone hydrochloride). The pharmacokinetic distinction may be due to a difference between the $C_{max}$ values associated with the immediate-release and sustained-release formulations. The sustained-release naltrexone formulation may provide a naltrexone $C_{max}$ and/or a 6-beta naltrexol $C_{max}$ that is about 80% or less of the naltrexone $C_{max}$ and/or the 6-beta naltrexol $C_{max}$ of an immediate-release naltrexone formulation (e.g., REVIA™ immediate-release naltrexone hydrochloride).

In some embodiments, the sustained-release naltrexone formulation provides a naltrexone $AUC_{last}$ and/or a 6-beta naltrexol $AUC_{last}$ that substantially similar to (e.g., between about 80% to about 125% of) a naltrexone $AUC_{last}$ and/or a 6-beta naltrexol $AUC_{last}$ of an immediate-release naltrexone formulation (e.g., REVIA™ immediate-release naltrexone hydrochloride).

In some embodiments, the naltrexone dosage of the immediate-release naltrexone formulation is substantially the same as the naltrexone dosage of the sustained-release naltrexone formulation. In some embodiments in which a $C_{max}$ value differs between the immediate-release and sustained release formulations, the naltrexone formulation is identified as one that provides a naltrexone $AUC_{last}$ and/or a 6-beta naltrexol $AUC_{last}$ that is substantially similar to (e.g., between about 80% to about 125% of) a naltrexone $AUC_{last}$ and/or a 6-beta naltrexol $AUC_{last}$ of the sustained-release naltrexone formulation The pharmacokinetic profile may be related to an effectiveness and/or a reduced side effect produced by the dosage form. For example, a sustained-release naltrexone formulation may produce substantially similar or improved efficacy as compared to an immediate-release naltrexone formulation due to a substantially similar naltrexone and/or 6-beta naltrexol $AUC_{last}$. As another example, a sustained-release naltrexone formulation may provide a reduction in an adverse effect as compared to that of an immediate-release naltrexone formulation due to a lower naltrexone and/or 6-beta naltrexol $C_{max}$.

Pharmacokinetic profiles can be determined by analyzing the plasma of a patient population that has received sustained-release naltrexone oral dosage forms, and comparing them to a comparable patient population that has received an immediate-release formulation, using the appropriate clinical trial methodology and statistical analyses.

In some embodiments, the pharmacokinetic properties are after a single-drug dosage, while in others, they are at steady-state. For the single-dosage measurements, patients may be provided with a single dosage of a composition comprising the sustained-release naltrexone, and plasma specimens may be collected from the patient at different time periods relative to the administration of the composition to determine pharmacokinetic profiles. For the steady-state measurements, patients may be provided with a dosing regimen across a plurality of days comprising administering oral dosage forms comprising sustained-release naltrexone. Plasma specimens may then be collected from the patient at different time periods relative to a particular dosage during steady state. In some embodiments, the steady state can be determined by monitoring a plasma naltrexone and/or active naltrexone metabolite (e.g., 6 beta-naltrexol) concentration profiles at specific times of anticipated peak and trough blood levels relative to the administration of a dosage across hours and days and determining when the profile has reached steady state. For example, the in vivo plasma naltrexone and/or active naltrexone metabolite (e.g., 6 beta-naltrexol) concentration may be measured one hour after dosing across days, until the concentration no longer significantly varies from day to day. In other embodiments, the steady state may be estimated as a specific number of days after the dosing regimen began. For example, steady state may be estimated as six days after the dosing regimen began. In some embodiments, steady state is estimated after dosing over about five times the half-life of the drug.

Plasma may be analyzed using any appropriate method. In some embodiments, blood is collected from a patient. Any suitable amount of blood may be collected. Blood samples may then be centrifuged until separation of red cells from plasma occurs. In some embodiments, naltrexone and/or naltrexone metabolite analysis is performed according to the analytical method validation entitled "Validation of a High Performance Liquid Chromatographic Method Using Tandem Mass Spectrometry Lithium Heparinized Plasma," hereby incorporated by reference in its entirety.

In order to measure the pharmacokinetic parameters mentioned above, in vivo naltrexone and/or naltrexone metabolite (e.g., 6 beta-naltrexol) concentrations may be measured at various time intervals with respect to a naltrexone dosage. In some embodiments, these concentrations are measured at least 10 times within a 24 hour period.

In some embodiments, a patient population undergoes a dosing regimen comprising the administration of a sustained-release naltrexone oral dosage form as described herein, and the reported pharmacokinetic parameters are the average of the pharmacokinetic parameters across patients. The average may be obtained by calculating the parameters for each patient and then averaging across patients. In some embodiments, the averaging comprises a least-squares arithmetic mean or a least-squares geometric mean. In some embodiments, pharmacokinetic parameters are obtained from cross-over studies.

Methods of Treating

In some embodiments, a sustained-release naltrexone formulation is provided and/or administered as an oral dosage form. The oral dosage form may also include a second compound, which is described above. In an embodiment, oral dosage forms described herein are effective in the treatment of one or more of a weight-related condition. The weight-related condition may comprise a condition characterized by a body-mass index of greater than or equal to about 25 kg/m$^2$, greater than or equal to about 30 kg/m$^2$ or less than or equal to about 18.5 kg/m$^2$. The weight-related condition may comprise obesity. The weight-related condition may be caused or expected to be caused by administration of a medication. Oral dosage forms described herein may be effective in affecting (e.g., causing) weight loss, inhibiting weight gain and/or at least partially reversing weight gain.

The oral dosage form may be distributed, provided to a patent for self-administration or administered to a patient. The patient may be overweight or obese. The patient may have a body-mass index (BMI) of about 20 kg/m$^2$ or greater, about 25 kg/m$^2$ or greater, or about 30 kg/m$^2$ or greater. The patient may be obese. The patient may be suffering from diabetes.

Administration of sustained-release oral dosage forms described herein may provide substantially the same or better efficacy than immediate-release formulations. The sustained-release oral dosage forms may be associated with reduced adverse effects as compared to immediate-release formulations. In some embodiments, the administration of an oral dosage form described herein may result in improved patient compliance with a treatment (e.g., a weight-loss treatment and/or a naltrexone treatment).

In some embodiments, methods of the present invention include identifying a patient suffering from at least one adverse side effect and/or who is particularly susceptible to at least one adverse side effect associated with a weight-loss treatment (e.g., a weight-loss treatment that comprises administration of bupropion) and/or treatment with an immediate-release naltrexone formulation (e.g., REVIA™ immediate-release naltrexone hydrochloride), and providing or administering to the patient a sustained-release naltrexone dosage form as described herein.

Methods of use can include the step of administering a therapeutically-effective amount of the sustained-release dosage form to a mammal in need thereof by any suitable route or method of delivery, including those described herein. Actual dosage levels of the compounds in the pharmaceutical dosage forms may be varied so as to administer an amount of naltrexone that is effective to achieve the desired therapeutic response for a particular patient.

Dosages

It will be understood that the specific dose level of the sustained-released dosage forms described herein for any particular patient can depend upon any of a variety of factors including the genetic makeup, body weight, general health, diet, time and route of administration, combination with other drugs and the particular condition being treated, and its severity. In some embodiments, the naltrexone dosage of the sustained-release dosage forms is at least partially determined based upon the frequency of which the oral dosage form is administered. Sustained-release oral dosage forms may be administered more frequently, less frequently, or at substantially the same frequency as immediate-release formulations (e.g., REVIA™ immediate-release naltrexone hydrochloride).

In some embodiments, a sustained-release oral dosage form comprising naltrexone provides dosages in a naltrexone free base equivalent amount in the range of from about 4 mg to about 50 mg or in the range of about 10 mg to about 25 mg. The oral dosage form may include about 4 mg, about 8 mg, about 12 mg, about 16 mg, about 32 mg, or about 48 mg of naltrexone. The selection of a particular dosage may be based on the weight of the patient. The selection of a particular dosage may be based on the identity, dosage and/or dosing schedule of another compound being co-administered. Unit dosage forms suitable for administration to a human may be configured to provide a naltrexone free base equivalent dosage in the range of about 0.75 mg/kg to about 10 mg/kg, e.g., about 2 mg/kg (basis is mg of drug per kilogram of body weight). Dosages may be at least partially determined by a pharmacokinetic profile. For example, an amount of a sustained-release naltrexone oral dosage form may be administered that is sufficient to provide an $AUC_{last}$ substantially similar to that of an immediate-release naltrexone oral dosage form.

The sustained-release dosage forms described herein may be administered one, two or more times per day, with or without a loading dose. In some embodiments, the number of administrations per day is constant (e.g., one time per day). In other embodiments, it is variable. The number of administrations may change depending on effectiveness of the dosage form, observed side effects, external factors (e.g., a change in another medication), or the length of time that the dosage form has been administered.

In an embodiment, a sustained-release naltrexone dosage form further comprises a second compound, as described herein. The second compound may be present in any appropriate dosage. In an embodiment, the second compound comprises bupropion or a pharmaceutically acceptable salt thereof. The bupropion or pharmaceutically acceptable salt thereof may be a sustained release (SR) formulation. In an embodiment, the dosage form comprises both naltrexone and bupropion, e.g., in the form of a tri-layer tablet as described in U.S. Provisional Patent Application Ser. No. 60/865,157, filed Nov. 9, 2006. Examples of suitable unit dosage forms include those in which the tri-layer tablet includes, e.g., about 4 mg naltrexone SR and 90 mg of bupropion SR; about 8 mg naltrexone SR and 90 mg of bupropion SR; or about 12 mg naltrexone SR and 90 mg of bupropion SR. In an embodiment, the dosage form may be administered as two tablets twice a day, e.g., for a daily dosage of about 16 mg, about 32 mg, or about 48 mg naltrexone, and about 360 mg bupropion or a pharmaceutically acceptable salt thereof. In an embodiment, the second compound (e.g., bupropion or a pharmaceutically acceptable salt thereof) and naltrexone are co-administered separately, e.g., as separate dosage forms that are co-administered within about an hour of each other. In an embodiment, the separate dosage forms are administered at about the same time.

Formulations

Oral dosage forms may comprise naltrexone and a sustained-release carrier. A sustained release carrier includes, by way of non-limiting example, an ingredient or ingredients that are included in a pharmaceutical formulation in amounts that are effective to extend the release rate of naltrexone from the formulation as compared to an immediate-release formulation (e.g., REVIA™ immediate-release naltrexone hydrochloride). A sustained release carrier may be referred to herein as a retardant excipient. Examples of sustained release carriers include hydroxypropylmethyl cellulose, polyethylene oxide, polyacrylate, copolymer of acrylate and methacrylate, methacrylate polymer, copolymer of acrylate and methacrylate, copolymer of acrylate and methacrylate with ammonium group, copolymer of maleic anhydride and methyl vinyl ether, hydroxy propyl ethyl cellulose, hydroxy propyl cellulose, hydroxy ethyl cellulose, methyl cellulose, hydroxymethyl methacrylate, maltodextrin, natural gum and xanthan gum. In some embodiments, the sustained-release carrier composition comprises at least one of hydroxypropylmethylcellulose and polyoxyethylene. A sustained release carrier composition may contain one or more sustained release carriers, along with other suitable ingredients.

In some embodiments, an oral dosage form comprising naltrexone comprises an amount of a sustained-release carrier composition that is effective to render the dosage form pharmacokinetically distinct from an immediate-release formulation (e.g., REVIA™ immediate-release naltrexone hydrochloride). For example, relative to the immediate-release formulation, the amount and type of sustained-release carrier composition may be selected to reduce the naltrexone $C_{max}$ and/or the 6-beta naltrexol $C_{max}$ (e.g., to about 80% or less than the naltrexone $C_{max}$ of or 6-beta naltrexol $C_{max}$ of immediate-release naltrexone).

The amount of the sustained-release carrier composition may be effective to provide an in vitro release rate of the naltrexone of less than about 90%, or less than about 80%, in about 2 hours. The amount of the sustained-release carrier composition may be effective to provide an in vitro release rate of the naltrexone of less than about 98% in about 4 hours. The amount of the sustained-release carrier composition may be effective to provide an in vitro release rate of the naltrexone of less than about 80% or than about 70% in about 1 hour. In vitro release rate is determined by a standard dissolution test as described above.

A description of representative sustained release carrier materials can be found in the Remington: The Science and Practice of Pharmacy ($20^{th}$ ed, Lippincott Williams & Wilkens Publishers (2003)), which is incorporated herein by reference in its entirety. Those skilled in the art can formulate sustained-release carrier compositions using routine experimentation informed by the detailed guidance provided herein.

Dosage forms described herein may be formulated to comprise various excipients, binders, carriers, disintegrants, coatings, etc. Pharmaceutical preparations can be obtained by mixing one or more solid excipients with a pharmaceutical composition as described herein, optionally grinding the resulting mixture, and processing the mixture of granules, after adding suitable auxiliaries, if desired, to obtain pharmaceutical compositions suitable for use in various forms, e.g., as pills, tablets, powders, granules, dragees, capsules, liquids, sprays, gels, syrups, slurries, suspensions and the like, in bulk or unit dosage forms, for oral ingestion by a patient to be treated. Various examples of unit dosage forms are described herein; non-limiting examples include a pill, a tablet, a capsule, a gel cap, and the like. Examples of suitable excipients are listed below, some of which are mentioned above as having particular dissolution properties. Pharmaceutically acceptable carriers or diluents for therapeutic use are well known in the pharmaceutical art, and are described, for example, in Remington: The Science and Practice of Pharmacy (2003), which is hereby incorporated by reference in its entirety. The term "carrier" material or "excipient" herein can mean any substance, not itself a therapeutic agent, used as a carrier, diluent, adjuvant, binder, and/or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. The glidants may be one or more of colloidal silicon dioxide, talc, corn starch, DL-leucine, sodium lauryl sulfate, and magnesium, calcium and sodium stearates. The diluents may be one or more of lactose, starch, mannitol, sorbitol, dextrose, microcrystalline cellulose, dibasic calcium phosphate, sucrose-based diluents, confectioner's sugar, monobasic calcium sulfate monohydrate, calcium sulfate dihydrate, calcium lactate trihydrate, dextrates, inositol, hydrolyzed cereal solids, amylose, powdered cellulose, calcium carbonate, glycine, or bentonite. Acceptable excipients include lactose, sucrose, starch powder, maize starch or derivatives thereof, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, saline, dextrose, mannitol, lactose, lecithin, albumin, sodium glutamate, cysteine hydrochloride, and the like. Examples of suitable excipients for soft gelatin capsules include vegetable oils, waxes, fats, semisolid and liquid polyols. Suitable excipients for the preparation of solutions and syrups include, without limitation, water, polyols, sucrose, invert sugar and glucose. The pharmaceutical compositions can additionally include preservatives, solubilizers, stabilizers, wetting agents, emulsifiers, sweeteners, colorants, flavorings, buffers, coating agents, or antioxidants. Dissolution or suspension of the active ingredient in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice. The compound can also be made in microencapsulated form. If desired, absorption enhancing preparations (for example, liposomes), can be utilized. Those skilled in the art can formulate sustained-release dosage forms containing one or more of the foregoing ingredients by routine experimentation informed by the detailed guidance provided herein.

Kits

In some embodiments, the present invention relates to a kit. The kit may include one or more unit dosage forms comprising sustained-release naltrexone. The unit dosage forms may be of an oral formulation. The unit dosage forms may comprise tablets. The kit may include a plurality of unit dosage forms.

The kit may include information. The information may be in a form prescribed by a governmental agency regulating the manufacture, use, or sale of pharmaceuticals, which notice is reflective of approval by the agency of the form of the drug for human or veterinary administration. Such information, for example, may be the labeling approved by the U.S. Food and Drug Administration for prescription drugs, or the approved product insert. Dosage forms comprising a sustained-release naltrexone formulation of the invention formulated in a compatible pharmaceutical carrier may also be prepared, placed in an appropriate container, and labeled for treatment of an indicated condition.

The information may comprise instructions to administer the unit dosage form at a dosage of about 4 mg, about 8 mg, about 12 mg, about 16 mg, about 32 mg or about 48 mg. These instructions may be provided in a variety of ways. The information may comprise instructions about when to administer the unit dosage forms. For example, the information may comprise instructions about when to administer the unit dosage forms relative to the administration of another medication or meal.

The information may be provided on a readable medium. The readable medium may comprise a label. The kit may comprise a therapeutic package suitable for commercial sale. The kit may comprise a container. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual dosages for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

The information can be associated with the container, for example, by being: written on a label (e.g., the prescription label or a separate label) adhesively affixed to a bottle containing a dosage form described herein; included inside a container as a written package insert, such as inside a box which contains unit dose packets; applied directly to the container such as being printed on the wall of a box; or attached as by being tied or taped, for example as an instructional card affixed to the neck of a bottle via a string, cord or other line, lanyard or tether type device. The information may be printed directly on a unit dose pack or blister pack or blister card.

EXAMPLES

The examples below are non-limiting and are merely representative of various aspects of the invention.

Example 1

A series of sustained-release naltrexone (5 mg) formulations were prepared. Each of the sustained-release formulations contained a "common excipient". The formulation for the common excipient is shown in Table 1. The formulation shown in Table 2 contained hydroxypropylmethyl cellulose as a sustained release carrier or retardant excipient. The formulation is shown in Table 3 contained polyethylene oxide as a retardant excipient.

To make the common excipient, the ingredients listed in Table 1 were placed into a Key KG-5 hi-shear granulator (Key International, Englishtown, N.J.) and granulated with a 10% hydroxypropyl cellulose (HPC) solution. The granulation was dried at room temperature to a final LOD of 2.71% and then screened through a 20-mesh sieve.

To manufacture the naltrexone formulations, the active pharmaceutical ingredient (API) was mixed with a colloidal silicon dioxide as a glidant, the extending release polymer (e.g., either HPMC or PolyOx) and the common excipient using a TURBULA mixer. Magnesium stearate was added as a lubricant to the final formulation.

Tablets with a 5Kp harness were compressed to determine the disintegration properties of the tablet. Under the conditions used, the 5Kp tablet did not disintegrate within 30 minutes in USP water. Accordingly, tablets with a higher hardness were compressed to 9Kp using ¼" round standard concave tooling on a Carver press.

Tablets compressed at 9Kp were produced, and the properties of the tablets are listed in Table 4.

TABLE 1

Formulation for the Common excipient

| Ingredient | Amount (Percent) |
| --- | --- |
| Hydroxypropyl cellulose (Klucel HXF) | 3.000 |
| Microcrystalline cellulose, NF (Avicel PH 102) | 77.000 |
| Lactose Fast Flo, (Type 316) NF | 20.000 |
| USP water | NA |
| Total | 100.000 |

TABLE 2

Formulations for Sustained Release 5 mg Strength Tablets Containing Hydroxypropylmethylcellulose (HPMC)

| Ingredient | 5% HPMC % per tablet | 10% HPMC % per tablet | 15% HPMC % per tablet | 22% HPMC % per tablet | 44% HPMC % per tablet | 66% HPMC % per tablet |
| --- | --- | --- | --- | --- | --- | --- |
| Naltrexone (5 mg) | 6.667 | 6.667 | 6.667 | 6.667 | 6.667 | 6.667 |
| Hydroxypropyl-methylcellulose (Methocel K15 Premium) | 5.000 | 10.000 | 15.000 | 22.000 | 44.333 | 66.000 |
| Common QBQ01 Placebo Granulation | 86.833 | 81.833 | 76.833 | 69.833 | 47.500 | 25.833 |
| Colloidal Silicon Dioxide, NF (Cab-O-Sil M5P) | 1.000 | 1.000 | 1.000 | 1.000 | 1.000 | 1.000 |
| Magnesium Stearate, NF, Ph. Eur.(Vegetable Source) (Grade, 905-G) | 0.500 | 0.500 | 0.500 | 0.500 | 0.500 | 0.500 |

TABLE 3

Formulations for Sustained Release 5 mg Strength Tablets Containing Polyethylene Oxide (PolyOx)

| Ingredient | 5% PolyOx % per tablet | 10% PolyOx % per tablet | 20% PolyOx % per tablet | 30% PolyOx % per tablet | 59% PolyOx % per tablet | 75% PolyOx % per tablet |
|---|---|---|---|---|---|---|
| Naltrexone (5 mg) | 6.667 | 6.667 | 6.667 | 6.667 | 6.667 | 6.667 |
| Polyethylene Oxide | 5.000 | 10.000 | 20.000 | 30.000 | 59.333 | 75.000 |
| Common QBQ01 Placebo Granulation | 86.833 | 81.833 | 71.833 | 61.833 | 32.500 | 16.833 |
| Colloidal Silicon Dioxide, NF (Cab-O-Sil M5P) | 1.000 | 1.000 | 1.000 | 1.000 | 1.000 | 1.000 |
| Magnesium Stearate, NF, Ph. Eur.(Vegetable Source) (Grade, 905-G) | 0.500 | 0.500 | 0.500 | 0.500 | 0.500 | 0.500 |

TABLE 4

In-Process Tablet Data

| Formulation | Weight (mg) (N = 3) | Thickness (mm) (N = 3) | Hardness (Kp) (N = 3) | Compression force (psi) |
|---|---|---|---|---|
| 5% HPMC | 75.0 | 2.47 | 9.2 | 850 |
| 10% HPMC | 75.8 | 2.5 | 8.7 | 800 |
| 15% HPMC | 75.5 | 2.52 | 8.7 | 800 |
| 22% HPMC | 74.2 | 2.45 | 9.2 | 850 |
| 44% HPMC | 75.1 | 2.64 | 8.7 | 750 |
| 66% HPMC | 73.9 | 2.65 | 9.6 | 650 |
| 5% PolyOx | 75.7 | 2.48 | 8.3 | 650 |
| 10% PolyOx | 76.6 | 2.53 | 8.9 | 750 |
| 20% PolyOx | 75.9 | 2.54 | 8.7 | 850 |
| 30% PolyOx | 74.5 | 2.53 | 8.9 | 650 |
| 59% PolyOx | 75.1 | 2.64 | 9.3 | 300 |
| 75% PolyOx | 75.9 | 2.84 | 9.4 | 250 |

The following example describes the dissolution profiles of the sustained release naltrexone formulations described above.

Example 2

Figure 2:
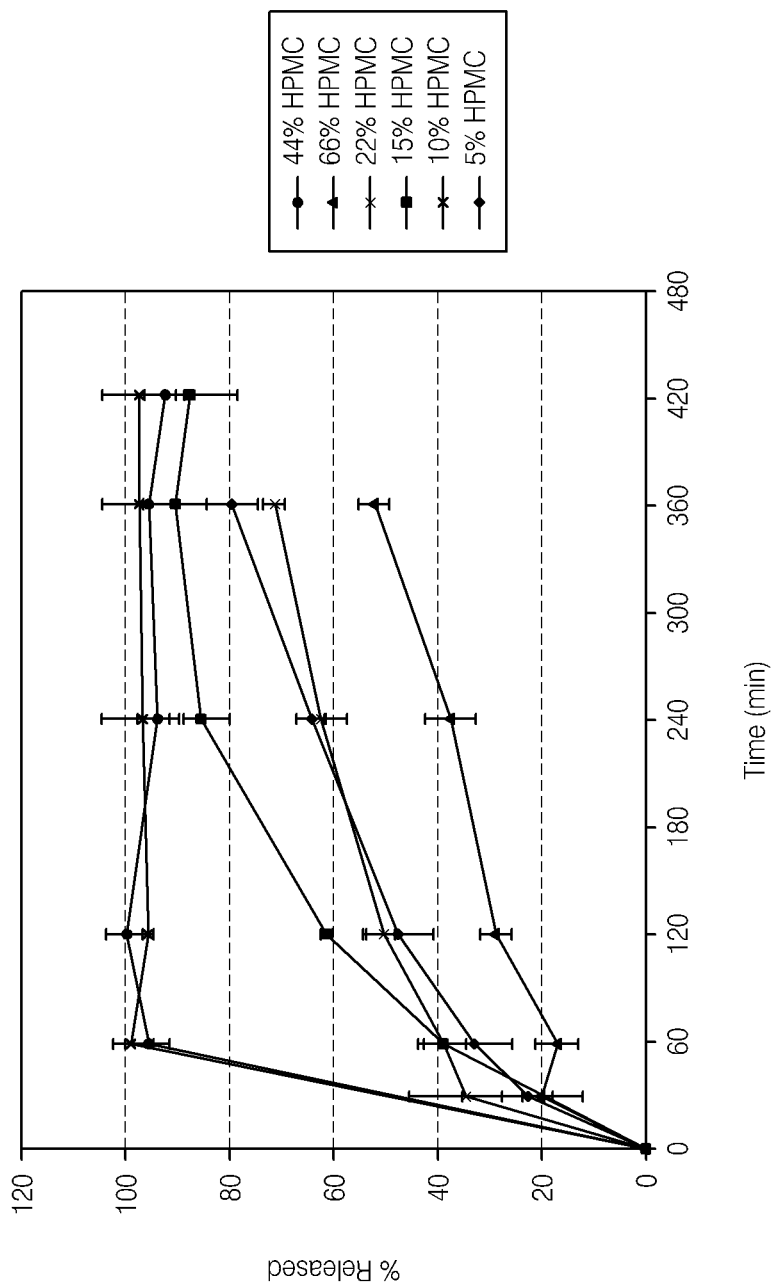
FIG. 2 shows the dissolution profile of sustained release 5 mg naltrexone tablets containing hydroxypropylmethyl cellulose.

The dissolution measurements for the tablets were completed using a 10-mesh baskets at 100 rpm. Samples were analyzed using a UV-VIS at $\lambda_{max}$ of 280. The dissolution data of the active pharmaceutical ingredient (API) for the HPMC formulations and PolyOx formulations are presented in Tables 5 and 6, respectively. Dissolution data for the HPMC formulations and PolyOx formulations are also plotted in FIGS. 1 and 2, respectively.

TABLE 5

Dissolution Data for HPMC Formulations

| Time (min) | % API Released 5% HPMC | Std. Dev. 5% HPMC | % API Released 10% HPMC | Std. Dev. 10% HPMC | % API Released 15% HPMC | Std. Dev. 15% HPMC | % API Released 22% HPMC | Std. Dev. 22% HPMC | % API Released 44% HPMC | Std. Dev. 44% HPMC | % API Released 66% HPMC | Std. Dev. 66% HPMC |
|---|---|---|---|---|---|---|---|---|---|---|---|---|
| 0 | 0 | 0 | 0 | 0 | 0 | 0 | 0 | 0 | 0 | 0 | 0 | 0 |
| 30 | | | | | | | 35 | 11 | 23 | 5 | 20 | 8 |
| 60 | 96 | 4 | 99 | 4 | 39 | 5 | 39 | 4 | 33 | 7 | 17 | 4 |
| 120 | 100 | 4 | 96 | 1 | 62 | 1 | 51 | 3 | 48 | 7 | 29 | 3 |
| 240 | 94 | 4 | 97 | 8 | 86 | 6 | 63 | 5 | 65 | 3 | 38 | 5 |
| 360 | 96 | 0 | 98 | 7 | 91 | 6 | 72 | 2 | 80 | 5 | 53 | 3 |
| 420 | 93 | 4 | 98 | 7 | 88 | 9 | | | | | | |

TABLE 6

Dissolution Data for Polyethylene Oxide Formulations

| Time (min) | % API Released 5% PolyOx | Std. Dev. 5% PolyOx | % API Released 10% PolyOx | Std. Dev. 10% PolyOx | % API Released 20% PolyOx | Std. Dev. 20% PolyOx | % API Released 30% PolyOx | Std. Dev. 30% PolyOx | % API Released 59.3% PolyOx | Std. Dev. 59.3% PolyOx | % API Released 75% PolyOx | Std. Dev. 75% PolyOx |
|---|---|---|---|---|---|---|---|---|---|---|---|---|
| 0 | 0 | 0 | 0 | 0 | 0 | 0 | 0 | 0 | 0 | 0 | 0 | 0 |
| 30 | | | | | | | 37 | 13 | 29 | 1 | 22 | 12 |
| 60 | 75 | 7 | 51 | 5 | 31 | 7 | 47 | 6 | 40 | 3 | 34 | 24 |
| 120 | 74 | 6 | 62 | 4 | 46 | 6 | 57 | 3 | 54 | 1 | 42 | 15 |
| 240 | 77 | 4 | 69 | 5 | 54 | 6 | 68 | 5 | 75 | 4 | 63 | 17 |
| 360 | 79 | 6 | 68 | 3 | 59 | 4 | 73 | 10 | 85 | 10 | 78 | 13 |
| 420 | 80 | 4 | 70 | 5 | 58 | 4 | | | | | | |

Example 3

Sustained-release naltrexone-bupropion tri-layer tablets were made using the ingredients listed in Table 7 through Table 9, in accordance with the general methods for making tri-layer tablets described in U.S. Provisional Patent Application Ser. No. 60/865,157, filed Nov. 9, 2006, which is hereby incorporated by reference in its entirety. A sustained-release naltrexone formulation was made by combining the following components:

TABLE 7

Naltrexone Blend Formulation

| Component | mg/tablet | mass (g) |
| --- | --- | --- |
| Naltrexone Hydrochloride | 13.22 | 1983.0 |
| Edetate Disodium, USP | 0.23 | 34.5 |
| Hydroxypropylmethylcellulose (Methocel K15 Premium CR) | 22.50 | 3375.0 |
| Hydroxypropylcellulose | 11.00 | 1650.0 |
| Lactose Monohydrate NF, Fast Flo 316 | 45.50 | 6825.0 |
| Microcrystalline cellulose (Avicel PH102) | 128.95 | 19342.5 |
| Colloidal silicon dioxide, NF | 2.30 | 345.0 |
| Magnesium Stearate, NF | 1.30 | 195.0 |
| Total | 225.0 | 33750.0 |

Thus, the sustained-release naltrexone formulation includes 10% HPMC. A bupropion blend was made by combining the following components:

TABLE 8

Bupropion Blend Formulation

| Component | mg/tablet | mass (g) |
| --- | --- | --- |
| Bupropion Hydrochloride Granulation | 315.00 | 47250.0 |
| Magnesium Stearate | 2.00 | 300.0 |
| Total | 317.00 | 47550.0 |

An inert layer blend was made by combining the following components:

TABLE 9

Inert Blend Formulation

| Component | mg/tablet | mass (g) |
| --- | --- | --- |
| Anhydrous Lactose | 30.00 | 4500.0 |
| Microcrystalline cellulose (Avicel PH101) | 84.70 | 12705.0 |
| Crospovidone | 3.60 | 540.0 |
| Magnesium Stearate | 1.20 | 180.0 |
| FDC Blue #2 Aluminum Lake | 0.50 | 75.0 |
| Total | 120.0 | 18000.0 |

The sustained-release naltrexone formulation, bupropion blend and inert layer blends were used to form 150 tri-layer tablets with the naltrexone and bupropion layers on opposite sides of the inert layer, such that each tablet was 662.00 mg. The tablets each contained 11.94 mg of naltrexone (13.22 mg naltrexone hydrochloride).

Figure 3:
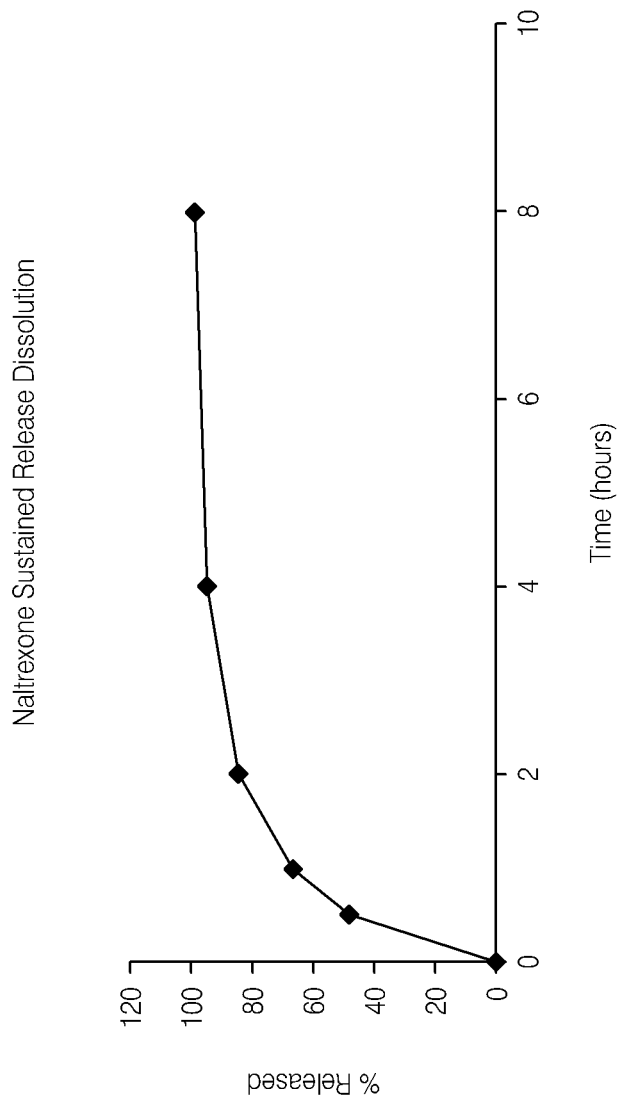
FIG. 3 shows the dissolution profile of sustained release naltrexone and bupropion tablets containing hydroxypropylmethyl cellulose.

The dissolution data of naltrexone for the tablets is presented in Table 10. Dissolution data is also plotted in FIG. 3.

TABLE 10

Dissolution Data for Naltrexone-Bupropion Tablets

| Time (Hours) | Naltrexone Released (Wt %) |
| --- | --- |
| 0 | 0 |
| 0.5 | 48 |
| 1 | 67 |
| 2 | 85 |
| 4 | 95 |
| 8 | 99 |

Example 4

A single center, double-blind, crossover study of immediate release naltrexone and sustained release naltrexone was conducted for 40 healthy obese volunteers.

Subjects were randomized to receive a naltrexone sustained-release formulation or an immediate-release formulation in a 1:1 ratio. Subjects were administered 40 mg of SR Naltrexone and 36 mg of IR Naltrexone. Subjects were randomly assigned to receive the sustained-release and immediate-release in one of two sequences: half of the subjects received the sustained-release formulation in period 1 followed by the immediate-release formulation in period 2; the remaining subjects received the treatments in the reverse order.

The administration of study drug in each period was separated by a five-day washout period. Serial blood samples were collected at predose and at 0.167, 0.33, 0.5, 0.67, 0.83, 1, 1.25, 1.5, 2, 3, 4, 6, 8, 10, 12, 16, 24, 36, 48, 60 and 72 hours post-dose. Samples were analyzed for the concentrations of naltrexone and 6-beta naltrexol by validated LCMS/MS methods. In addition to spontaneously collected adverse events, information on side effects was collected using the subject rated UKU Side Effect Rating Scale. The scale was administered predose, at 8, 24 and 72 hours post-dose.

The concentration-time data were imported directly into WinNonlin (Version 5.0, Pharsight Corporation). Data were analyzed by noncompartmental methods using WinNonlin using Model 200 for extravascular input.

Concentration-time data that were BLLOQ were excluded from calculations prior to data summarization and pharmacokinetic analysis. Data were summarized by scheduled (nominal) sampling times. Actual sampling times were used if the deviation from nominal was considered significant.

The following pharmacokinetic parameters were estimated for naltrexone and 6-beta naltrexol concentrations for each subject and each treatment:

$C_{max}$=measured maximal concentration
$T_{max}$=time to reach maximum concentration
Ke=terminal rate constant, estimated by log-linear regression
AUC(0-t)=area under the concentration-time curve calculated by the linear trapezoidal rule from time 0 to the time of last sample with a quantifiable concentration ($C_t$)
AUC(0-∞)=area under the concentration time curve from time 0 extrapolated to infinity, calculated as AUC (0-t)+ $C_t/K_e$
$T_{1/2}$=terminal half-life, calculated as $Ln(2)/K_e$ The AUC is used to describe the extent of drug absorption. The rate of absorption is characterized by $C_{max}$ and $T_{max}$. $K_e$ and $T_{1/2}$ describe the kinetics in the terminal phase, which, for many substances, is governed by elimination processes. Pharmacokinetic parameters were estimated for all cases.

Figure 4:
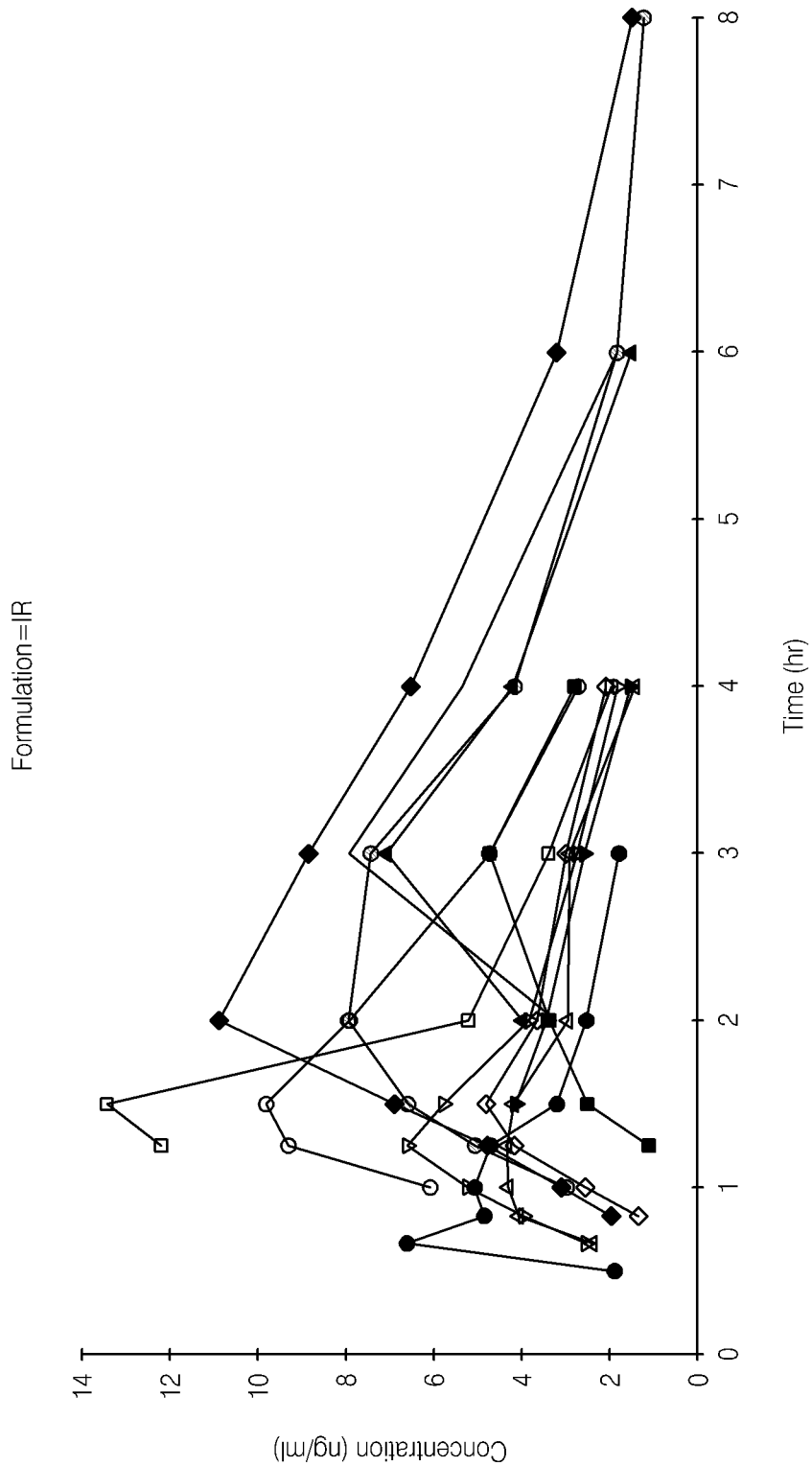
FIG. 4 shows the individual plasma concentration time curves of naltrexone in subjects receiving Naltrexone IR.
Figure 5:
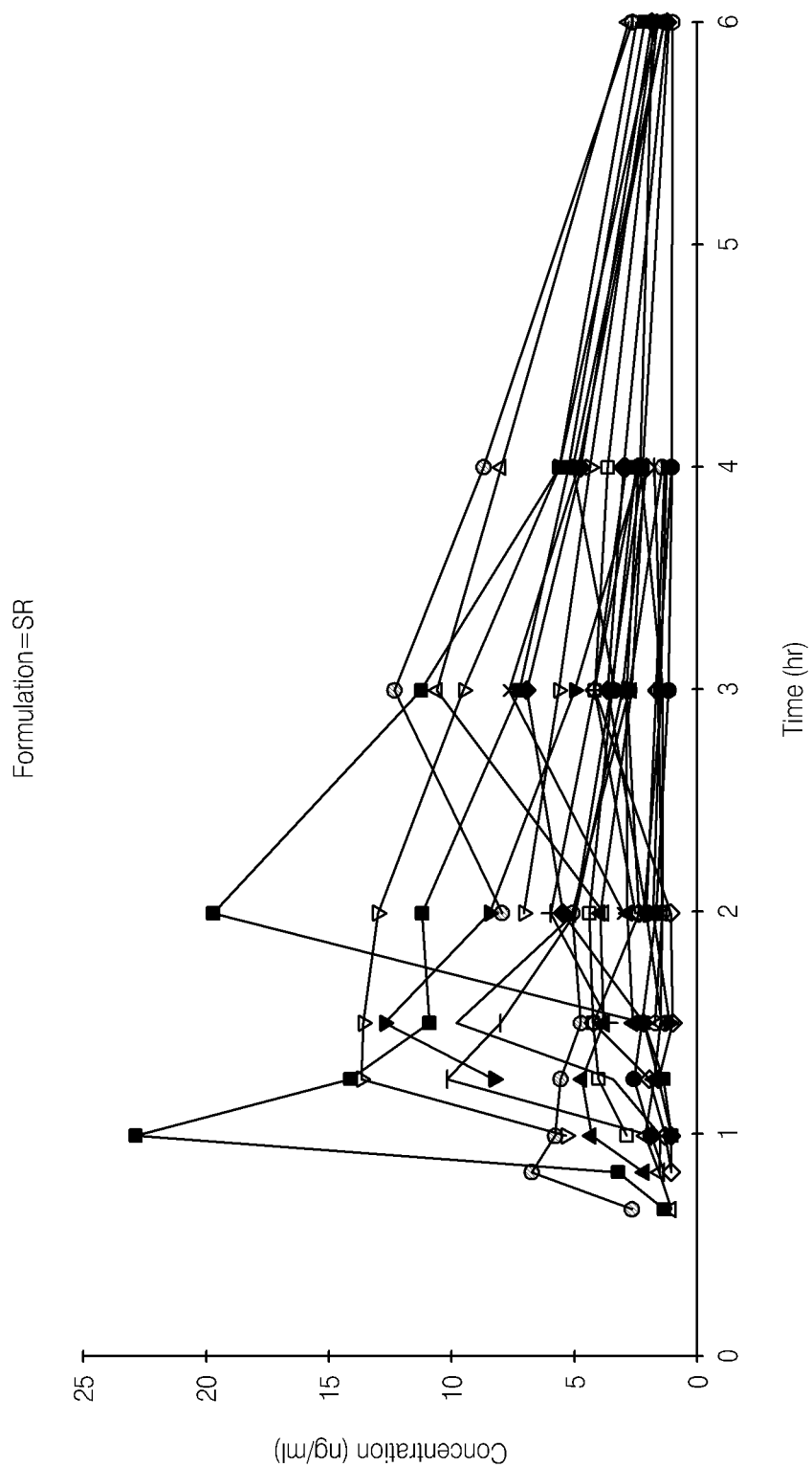
FIG. 5 shows the individual plasma concentration time curves of naltrexone in subjects receiving Naltrexone SR.
Figure 6:
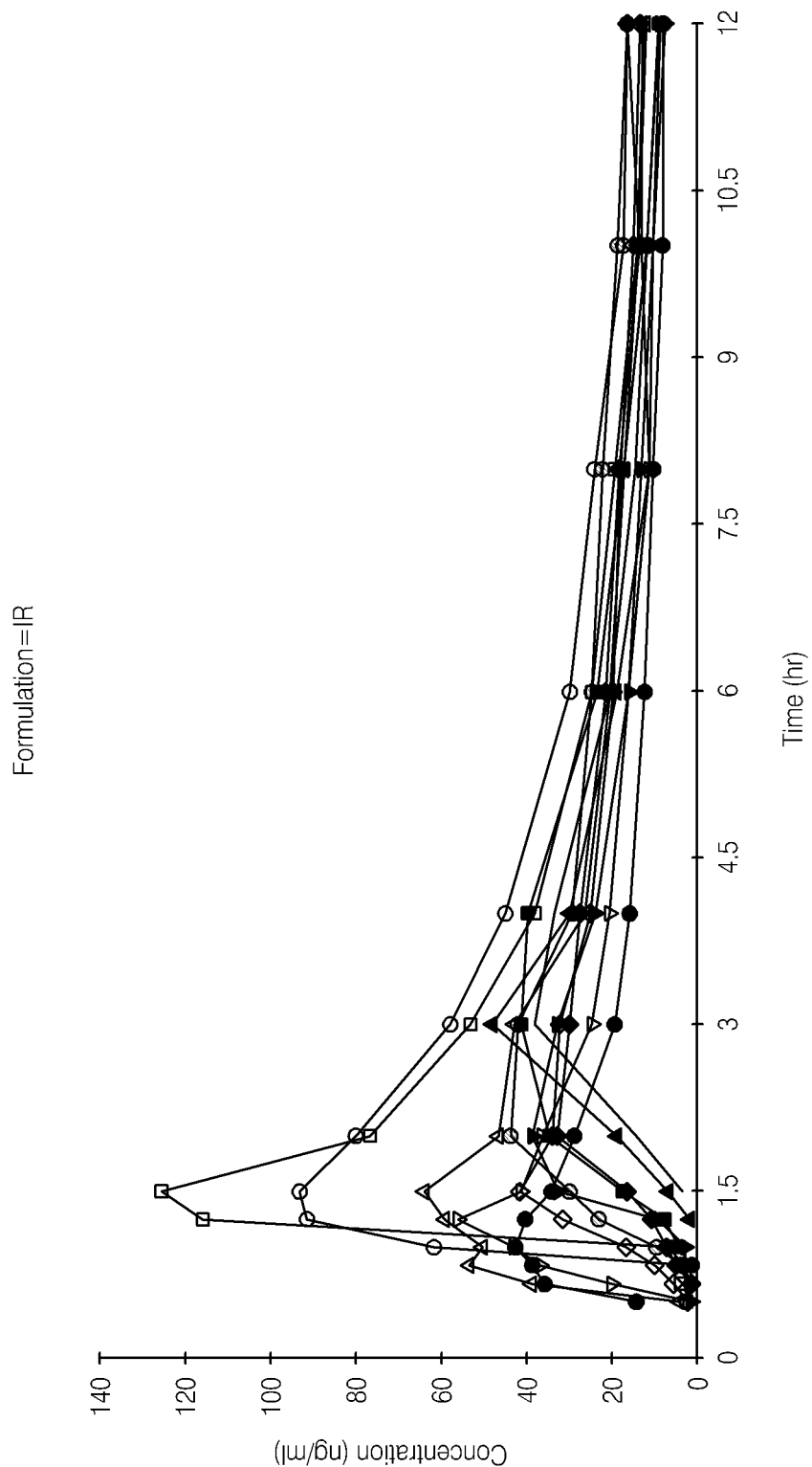
FIG. 6 shows the individual plasma concentration time curves of 6-beta naltrexol in subjects receiving Naltrexone IR.
Figure 7:
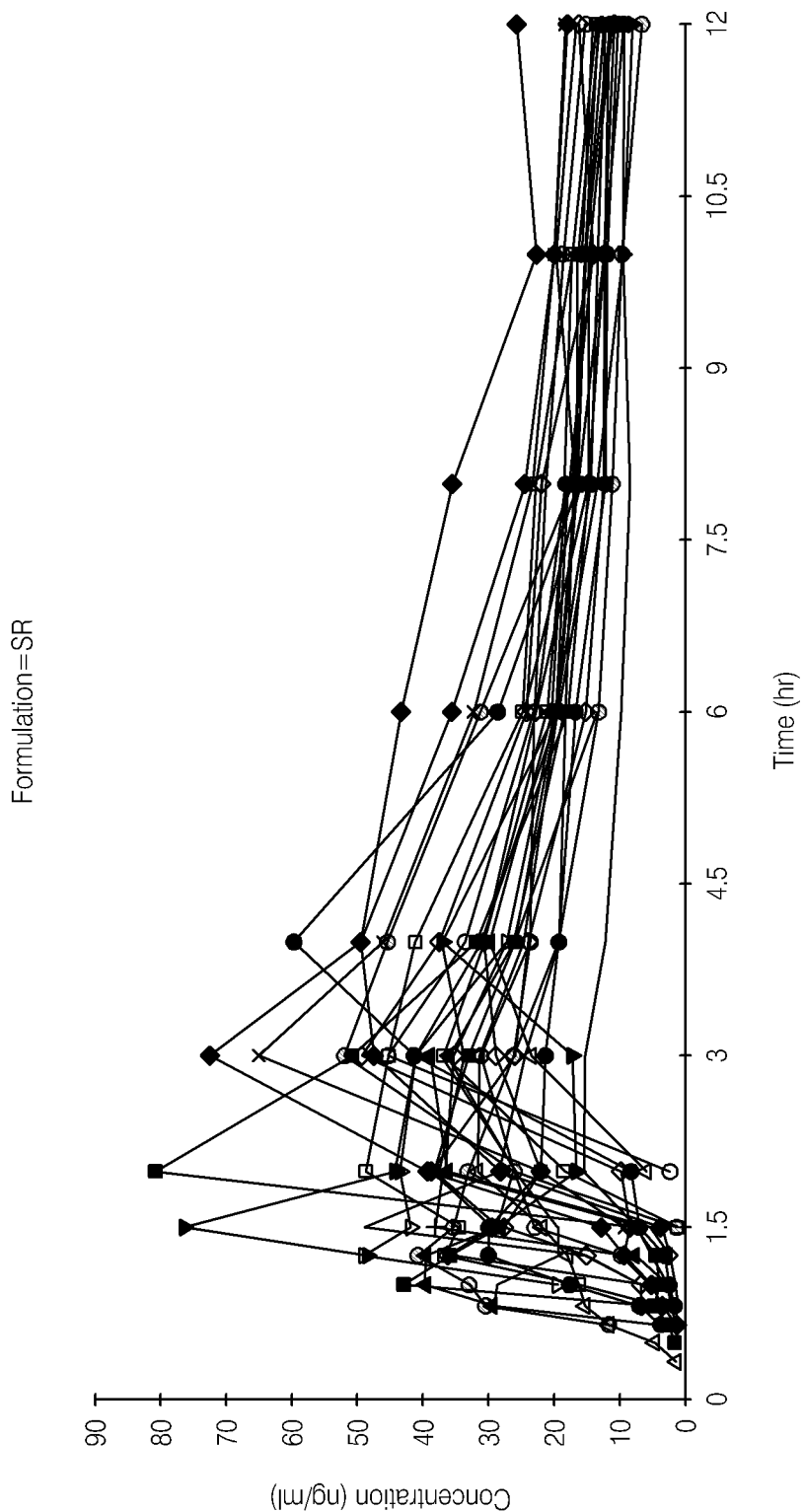
FIG. 7 shows the individual plasma concentration time curves of 6-beta naltrexol in subjects receiving Naltrexone SR.

FIGS. 4 and 5 show individual plasma concentration time curves of naltrexone in subjects receiving Naltrexone IR and in subjects receiving Naltrexone SR, respectively. FIGS. 6 and 7 show individual plasma concentration time curves of 6-beta naltrexol in subjects receiving Naltrexone IR and in subjects receiving Naltrexone SR, respectively.

Figure 8A:
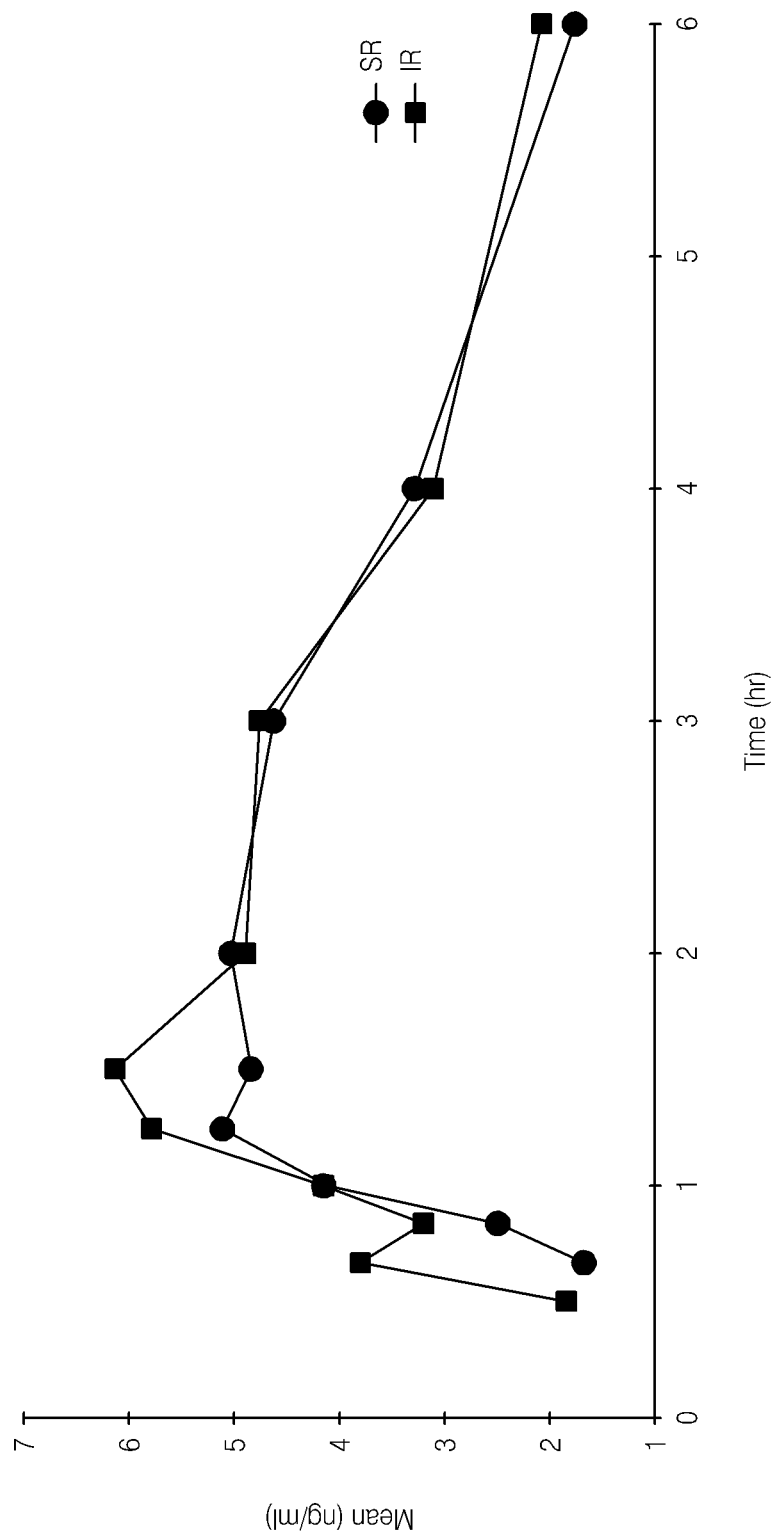
FIGS. 8A and 8B show the average plasma concentration time curves of naltrexone across subjects receiving Naltrexone SR (circles) or Naltrexone IR (squares) across two time scales.
Figure 8B:
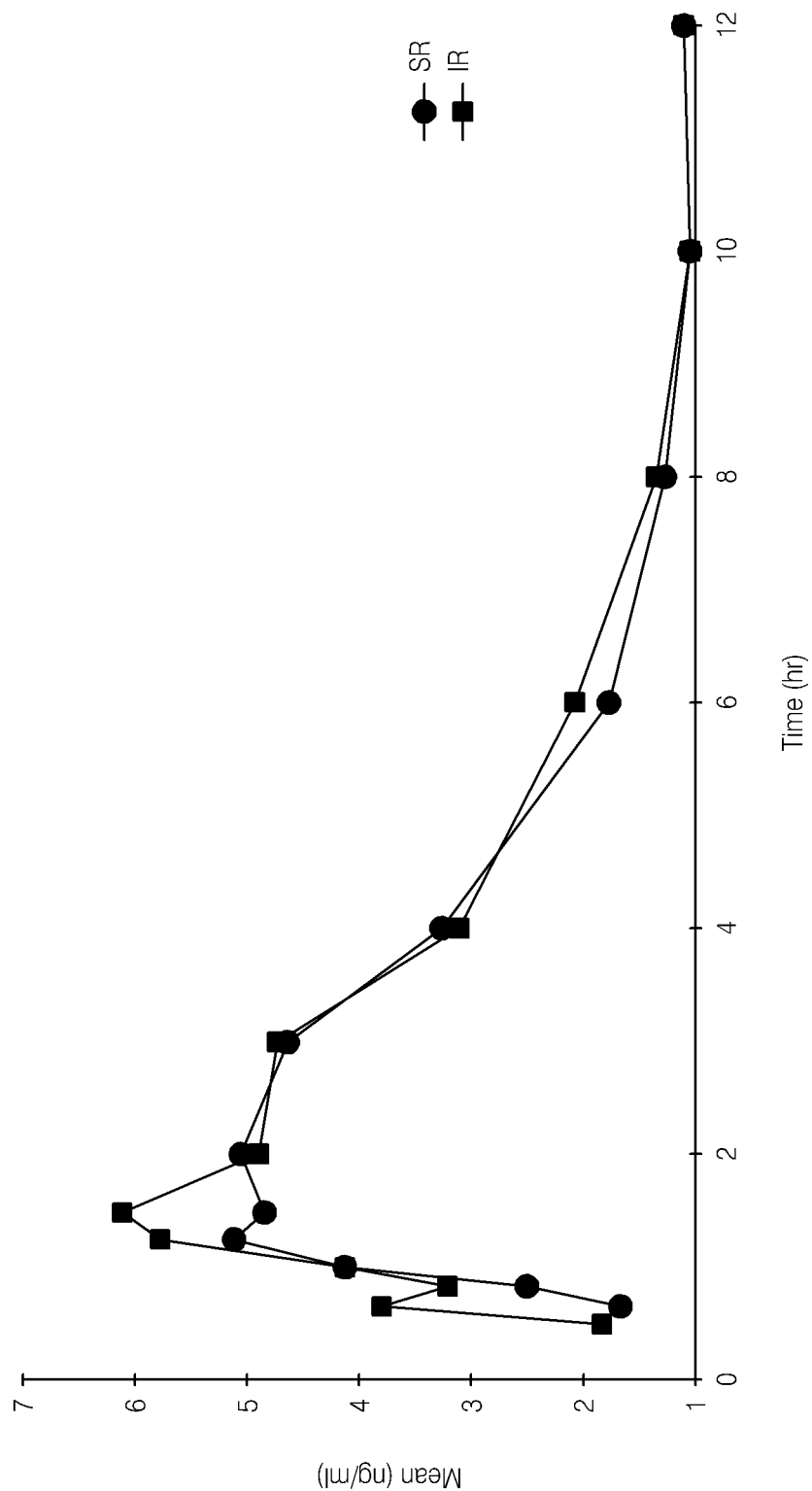

FIG. 8A shows the average plasma concentration time curves of naltrexone in subjects receiving Naltrexone SR (circle) or Naltrexone IR (square). FIG. 8B shows the entire plasma concentration time curve. The Naltrexone $C_{max}$ is higher for patients receiving Naltrexone IR than for those receiving Naltrexone SR though the area under the curve is comparable between both conditions. These results are dose normalized and quantified in Table 11.

TABLE 11

Summary of Pharmacokinetic Parameters in Subjects Receiving Naltrexone SR or Naltrexone IR

| Analyte | Formulation | $C_{max}$ (ng/mL) | $T_{max}$ (hr) | $AUC_{last}$ (ng * hr/mL) | $T_{1/2}$ (hr) |
|---|---|---|---|---|---|
| Naltrexone | SR | 5.10 | 1.25 | 27.48 | 4.01 |
|  | Dose Normalized | 4.59 |  | 24.7 |  |
|  | IR | 6.11 | 1.50 | 24.91 | 3.27 |

TABLE 11-continued

Summary of Pharmacokinetic Parameters in Subjects Receiving Naltrexone SR or Naltrexone IR

| Analyte | Formulation | $C_{max}$ (ng/mL) | $T_{max}$ (hr) | $AUC_{last}$ (ng * hr/mL) | $T_{1/2}$ (hr) |
|---|---|---|---|---|---|
| 6-beta naltrexol | SR | 37.45 | 3.00 | 486.00 | 16.55 |
|  | Dose Normalized | 33.7 |  | 437.4 |  |
|  | IR | 43.39 | 1.5 | 496.95 | 16.99 |

Figure 9A:
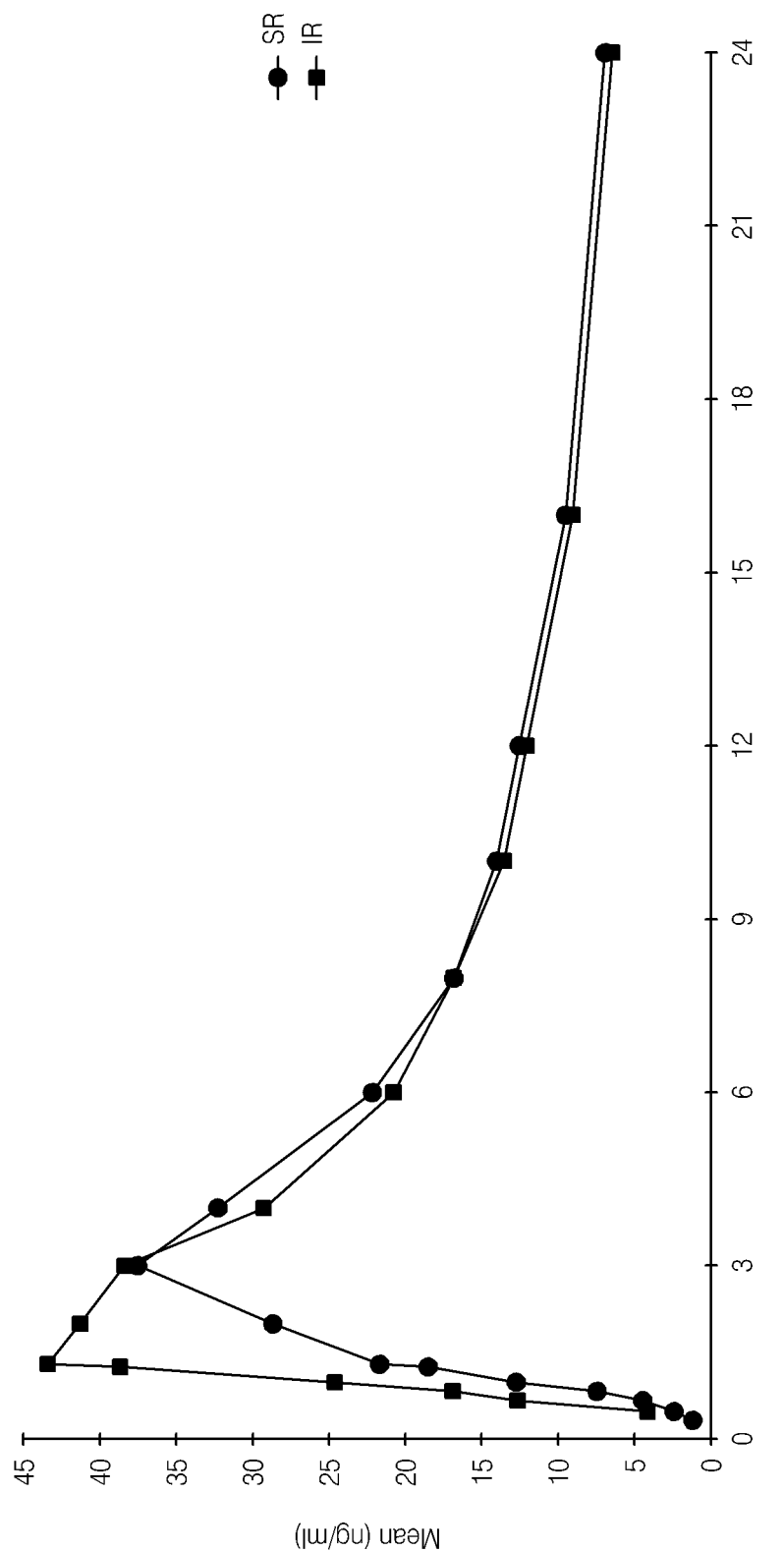
FIGS. 9A and 9B show the average plasma concentration time curves of 6-beta naltrexol across subjects receiving Naltrexone SR (circles) or Naltrexone IR (squares) across two time scales.
Figure 9B:
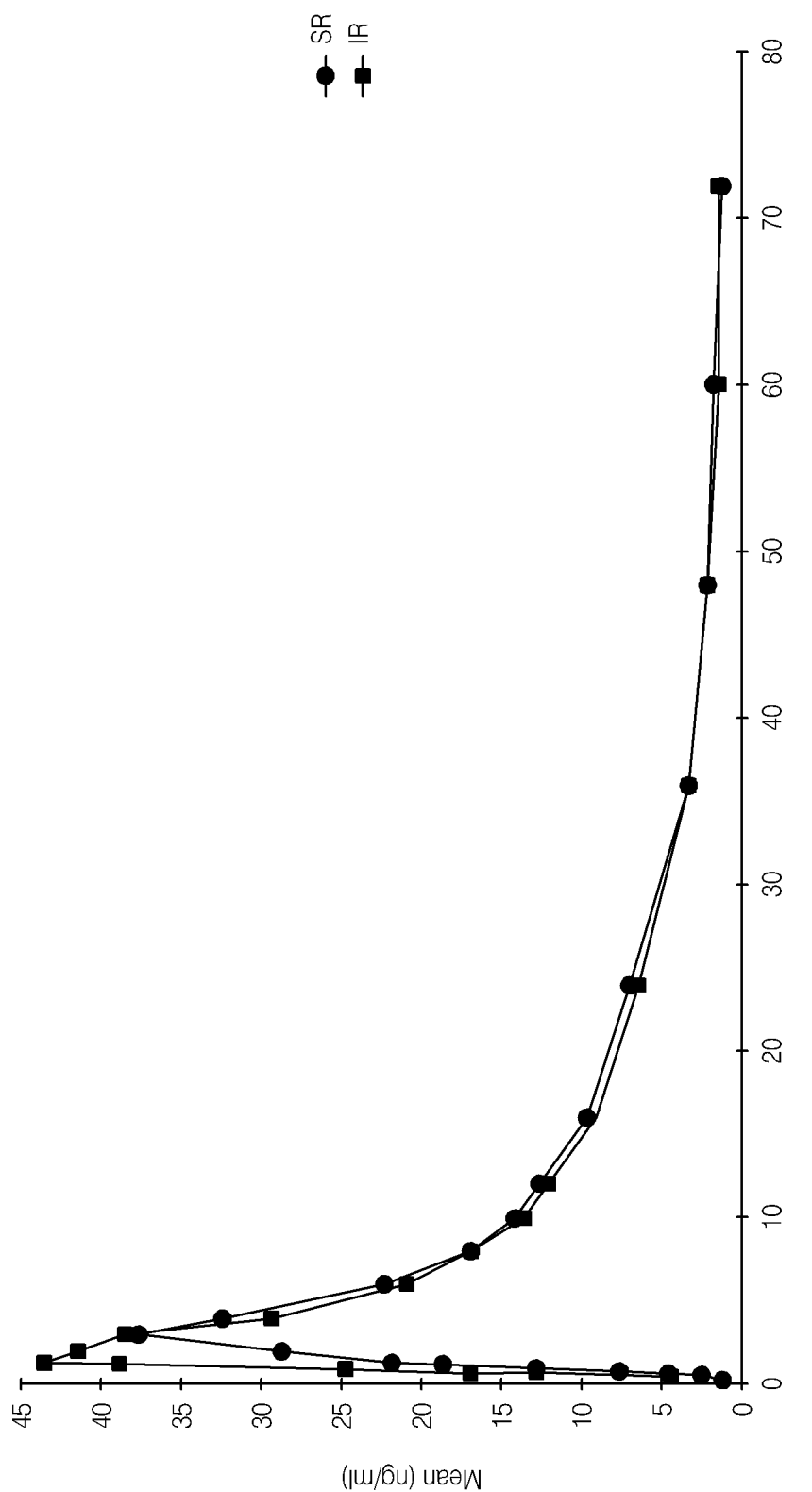

FIG. 9A shows the average plasma concentration time curves of 6-beta naltrexol in subjects receiving Naltrexone SR (circle) or Naltrexone IR (square). FIG. 9B shows the entire plasma concentration time curve. The 6-beta naltrexol $C_{max}$ is higher for patients receiving Naltrexone IR than for those receiving Naltrexone SR though the area under the curve is comparable between both conditions. These results are dose normalized and quantified in Table 11.

Table 12 provides the adverse events reported by patients receiving Naltrexone SR and by patients receiving Naltrexone IR. The adverse events are analyzed across patients for each of the treatment conditions. These results are summarized in Table 13. Individuals receiving Naltrexone SR were less likely to report an adverse event (45% versus 48%) and were also less likely to report more than one adverse event (13% versus 23%) than individuals receiving Naltrexone IR.

TABLE 12

Summary of Individual Adverse Events.

| Subject | Period | Treatment | AE YM | Adverse Event(s) | | | |
|---|---|---|---|---|---|---|---|
| 1 | 1 | SR | Yes | Nausea | | | |
| 4 | 1 | SR | Yes | Headache | Anemia | | |
| 5 | 1 | SR | Yes | Elevated platelet count | | | |
| 11 | 1 | SR | Yes | Hyperglycemia | | | |
| 16 | 1 | SR | Yes | Cramps, menstrual | | | |
| 17 | 2 | SR | Yes | Pyuria | | | |
| 19 | 1 | SR | Yes | Nausea | Elevated Leukocyte Esterase | Pyuria | |
| 22 | 1 | SR | Yes | Stomach pain | | | |
| 27 | 2 | SR | Yes | Hypophosphatemia | | | |
| 32 | 1 | SR | Yes | Hypertension | | | |
| 34 | 1 | SR | Yes | Headache | Headache | | |
| 35 | 1 | SR | Yes | Hyperleukemia | | | |
| 36 | 1 | SR | Yes | Nausea | Stomach Cramps | | |
| 37 | 1 | SR | Yes | Tingle in lips | | | |
| 39 | 1 | SR | Yes | Nausea | Diarrhea | Dizziness | |
| 40 | 2 | SR | Yes | Hematuria | Hypophosphatemia | | |
| 29 | 2 | SR | Yes | Increased TSH | | | |
| 1 | 2 | IR | Yes | Pyuria | | | |
| 2 | 2 | IR | Yes | Intermittent Diarrhea | Pyuria | Hematuria | |
| 4 | 2 | IR | Yes | Anemia | | | |
| 5 | 2 | IR | Yes | Elevated platelet count | | | |
| 7 | 2 | IR | Yes | Elevated blood pressure | | | |
| 11 | 2 | IR | Yes | Nausea | Hypertension | Proteinuria | Hematuria Hyperglycemia |
| 13 | 2 | IR | Yes | Hyperglycemia | | | |
| 15 | 2 | IR | Yes | Hyperleukemia | | | |
| 16 | 2 | IR | Yes | Blood in urine | | | |
| 18 | 2 | IR | Yes | Elevated Leukocyte Esterase | Pyuria | Leucocytosis | |
| 19 | 2 | IR | Yes | Nausea | | | |

TABLE 12-continued

Summary of Individual Adverse Events.

| Subject | Period | Treatment | AE YM | Adverse Event(s) | | |
|---|---|---|---|---|---|---|
| 22 | 2 | IR | Yes | Stomach pain | Vomited | Elevated Leukocyte Esterase |
| 23 | 1 | IR | Yes | Hyperglycemia | | |
| 25 | 2 | IR | Yes | Triglyceride | | |
| 27 | 1 | IR | Yes | Hypophosphatemia | | |
| 31 | 2 | IR | Yes | Hypertension | | |
| 32 | 2 | IR | Yes | Hypertension | Increased TSH | |
| 34 | 2 | IR | Yes | Elevated ALT | Increased TSH | |
| 35 | 2 | IR | Yes | Hyperglycemia | | |
| 36 | 2 | IR | Yes | Numbness in lips | Hyperglycemia | |

TABLE 13

Summary of Adverse Events, Gastrointestinal and Headache, in Subjects Receiving Naltrexone SR and Naltrexone IR.

| Item | Formulation | % | | |
|---|---|---|---|---|
| % Subjects Reporting AE | SR | 45% | 18 | 40 |
| | IR | 48% | 19 | 40 |
| % Subjects Reporting >1 AE | SR | 13% | 5 | 40 |
| | IR | 23% | 9 | 40 |
| % Subjects Reporting AEs in Both Periods | | 33% | 13 | 39 |
| % Subjects GI Reporting AE | SR | 13% | 5 | 40 |
| | IR | 10% | 4 | 40 |
| % Subjects Reporting >1 GI AE | SR | 5% | 2 | 40 |
| | IR | 3% | 1 | 40 |
| % Subjects Reporting GI AEs in Both Periods | (19, 22, 36) | 8% | 3 | |
| % Subjects GI Reporting Headache AE | SR | 5% | 2 | 40 |
| | IR | 0% | 0 | 40 |
| % Subjects Reporting Headache AEs in Both Periods | | 0% | 0 | 40 |

Figure 10:
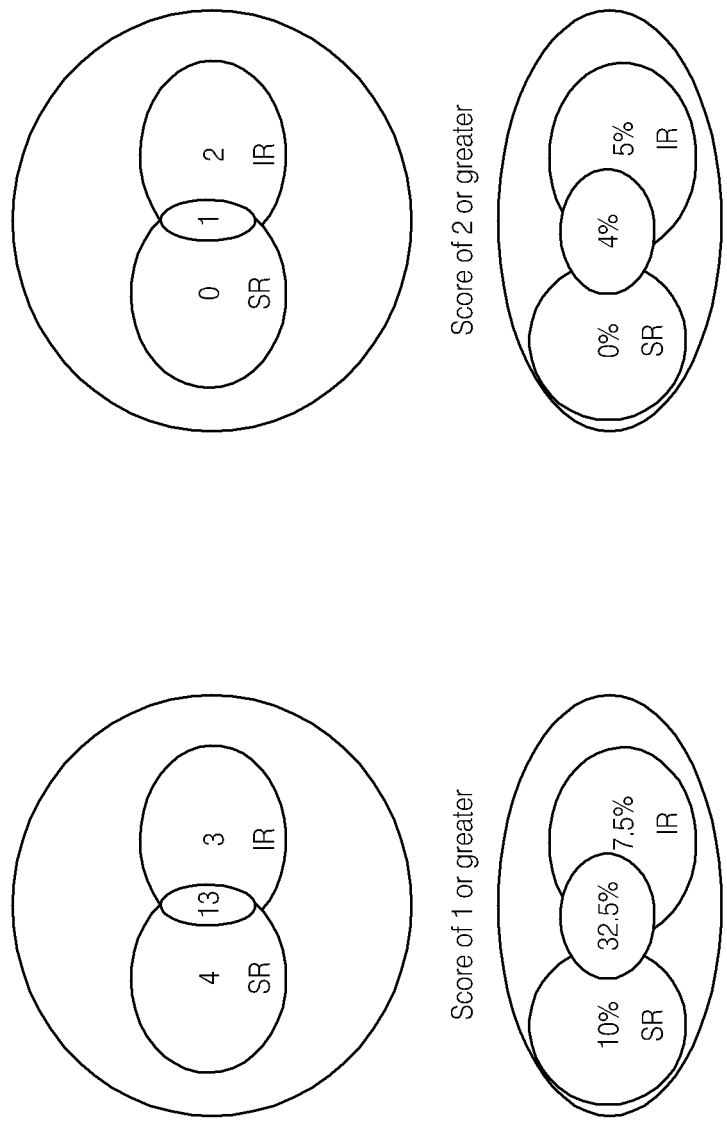
FIG. 10 is a schematic illustrating the population of subjects reporting nausea and vomiting using the UKU Adverse Event Rating Scale.

FIG. 10 is a schematic illustrating the population of subjects reporting nausea and vomiting using the UKU Adverse Event Rating Scale. Individuals receiving Naltrexone SR were less likely to report severe nausea (score of 2 or greater) than those receiving Naltrexone IR.

Those skilled in the art recognize that the incidence of adverse events reported using the UKU Adverse Event Rating Scale is typically higher than self-reporting. Patients have been reported to be more likely to report adverse events when prompted to report adverse events (Sheftell F D, Feleppa M, Tepper S J, Rapoport A M, Ciannella L, Bigal M E. Assessment of adverse events associated with triptans-methods of assessment influence the results. Headache: The Journal of Head and Face Pain 44 (10), 978-982). Thus, the incidence of adverse events obtained by the methods used in this example is not directly comparable to the incidence of adverse events obtained by the methods described in Example 5.

Example 5

A randomized double-blind, parallel, multiple dose study compared the pharmacokinetics of a naltrexone SR/bupropion SR combination product with a naltrexone IR/bupropion SR combination product.

Naltrexone SR/bupropion SR group: Each capsule contained two and one-half 5 mg mini tablets (prepared in accordance with Example 1) of sustained release naltrexone plus one 90 mg bupropion HCl SR tablet (total dose of naltrexone SR 12.5 mg/bupropion SR 90 mg per capsule) which was titrated over 7 days to a total daily dose of naltrexone SR 37.5 mg/bupropion SR 270 mg.

Naltrexone IR/bupropion SR group: Each capsule contained capsules containing one 12 mg naltrexone HCl IR tablet plus one 90 mg bupropion HCl SR tablet (total dose of 12 mg naltrexone IR/90 mg bupropion SR per capsule) which was titrated over 7 days to a final daily dose of naltrexone IR 36 mg/bupropion SR 270 mg. The naltrexone IR formulation is formulated to have a pharmacokinetic profile that is substantially similar to the REVIA® brand of naltrexone hydrochloride.

Healthy obese volunteers randomly received one of the two drug administrations. A total of 60 subjects were expected to enroll, 59 subjects completed the study.

Blood was drawn on Day 1 (0.5, 1, 2, 4, 6, 8, 10, and 12 hrs) with trough samples drawn on Days 8 and 15. Plasma samples were drawn from each subject to determine naltrexone, 6-beta-naltrexol, bupropion, hydroxybupropion, threohydroxybupropion, and erthyrohydroxybupropion concentrations. Plasma samples were analyzed using the SFBCi/Anapharm validated methods for naltrexone and 6-beta naltrexol. The concentration-time data were imported directly into WinNonlin (Version 5.0, Pharsight Corporation). Data were analyzed by noncompartmental methods using WinNonlin using Model 200 for extravascular input.

Concentration-time data that were BLLOQ were excluded from calculations prior to data summarization and pharmacokinetic analysis. Data were summarized by scheduled (nominal) sampling times. Actual sampling times were used if the deviation from nominal was considered significant.

Pharmacokinetic parameters measured herein are known to those skilled in the art. Blood plasmas were collected at specific intervals relative to the administration of a combination product. The plasma was analyzed to determine the concentration of a compound (e.g., naltrexone). $C_{max}$ indicates the maximum blood plasma concentration of the compound after administration. $T_{max}$ indicates the time at which the maximum blood plasma concentration of the compound ($C_{max}$) was reached. AUC indicates the area under the curve of the concentration as a function of time following administration. $AUC_{last}$ indicates the area under the plasma-concentration curve from the time of administration until the time of the last measurable concentration.

Figure 11:
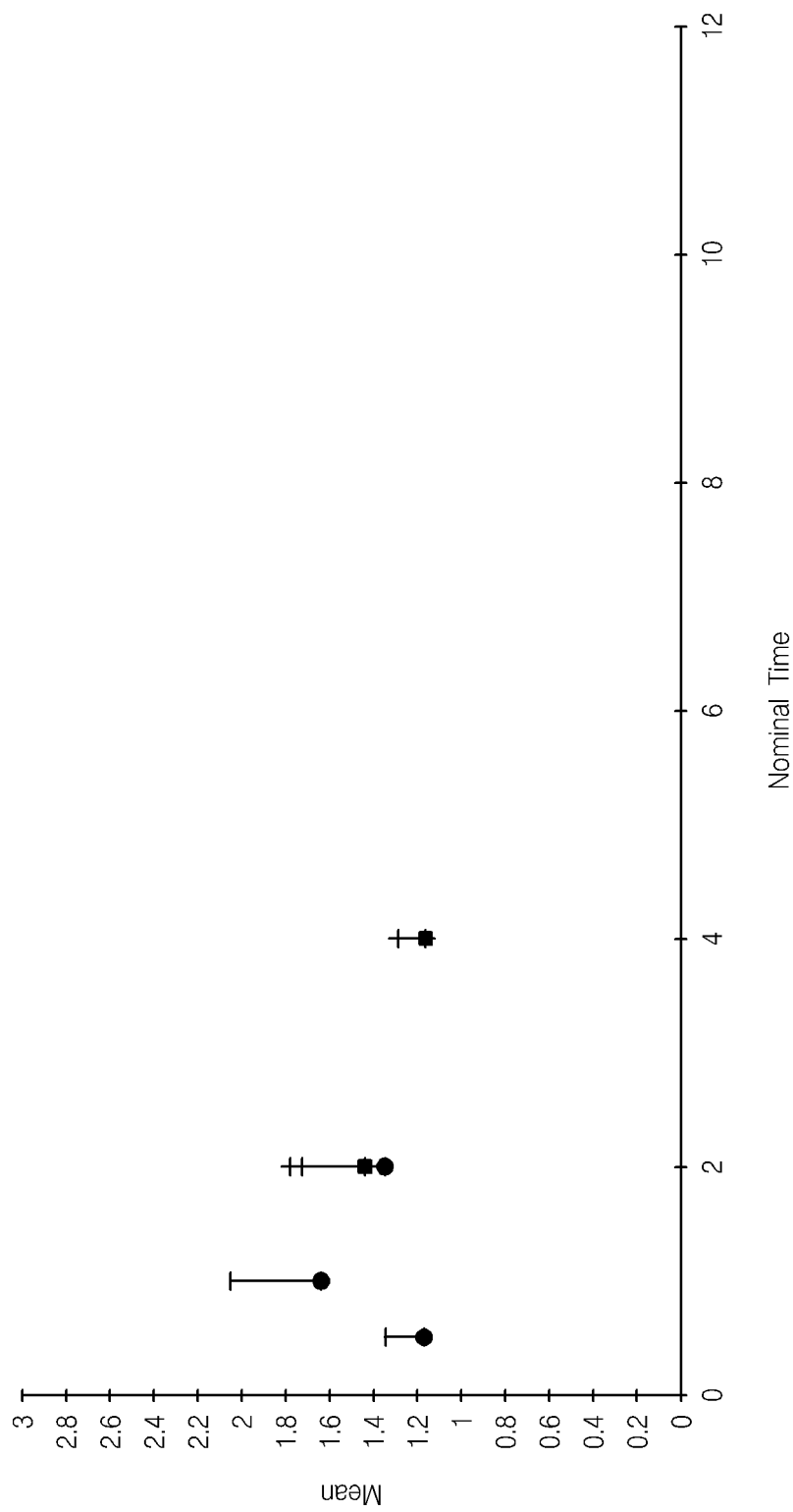
FIG. 11 shows the average plasma concentrations of naltrexone in subjects receiving naltrexone IR in combination with bupropion SR (●) or naltrexone SR in combination with bupropion SR (■).

Table 14 and FIG. 11 compare average naltrexone plasma concentrations in subjects receiving treatments of naltrexone IR and bupropion SR (IR/SR; circles) to that in subjects receiving treatments of naltrexone SR and bupropion SR (SR/SR; squares). The single dose of naltrexone at the onset of the titration schedule of 12 (IR) or 12.5 (SR) produces plasma concentrations during the first 24 hours that are primarily below the lower limit of quantitation (BLLOQ).

TABLE 14

Mean plasma concentrations of naltrexone in subjects receiving naltrexone IR in combination with bupropion SR (IR/SR) or naltrexone SR in combination with bupropion SR (SR/SR).

| Treatment | Time (hr) | N | Mean (ng/mL) | SD (ng/mL) | CV % |
|---|---|---|---|---|---|
| IR/SR | 0 | 0 | NC | NC | NC |
|  | 0.5 | 8 | 1.17 | 0.18 | 15.45 |
|  | 1 | 18 | 1.64 | 0.41 | 25.28 |
|  | 2 | 10 | 1.36 | 0.37 | 27.44 |
|  | 4 | 0 | NC | NC | NC |
|  | 6 | 0 | NC | NC | NC |
|  | 8 | 0 | NC | NC | NC |
|  | 10 | 0 | NC | NC | NC |
|  | 12 | 0 | NC | NC | NC |
|  | 168 | 0 | NC | NC | NC |
|  | 336 | 1 | 6.78 | NC | NC |
| SR/SR | 0 | 0 | NC | NC | NC |
|  | 0.5 | 0 | NC | NC | NC |
|  | 1 | 0 | NC | NC | NC |
|  | 2 | 11 | 1.44 | 0.34 | 23.59 |
|  | 4 | 3 | 1.17 | 0.12 | 10.45 |
|  | 6 | 0 | NC | NC | NC |
|  | 8 | 0 | NC | NC | NC |
|  | 10 | 0 | NC | NC | NC |
|  | 12 | 0 | NC | NC | NC |
|  | 168 | 1 | 1.18 | NC | NC |
|  | 336 | 2 | 2.55 | 1.64 | 64.1 |

Figure 12:
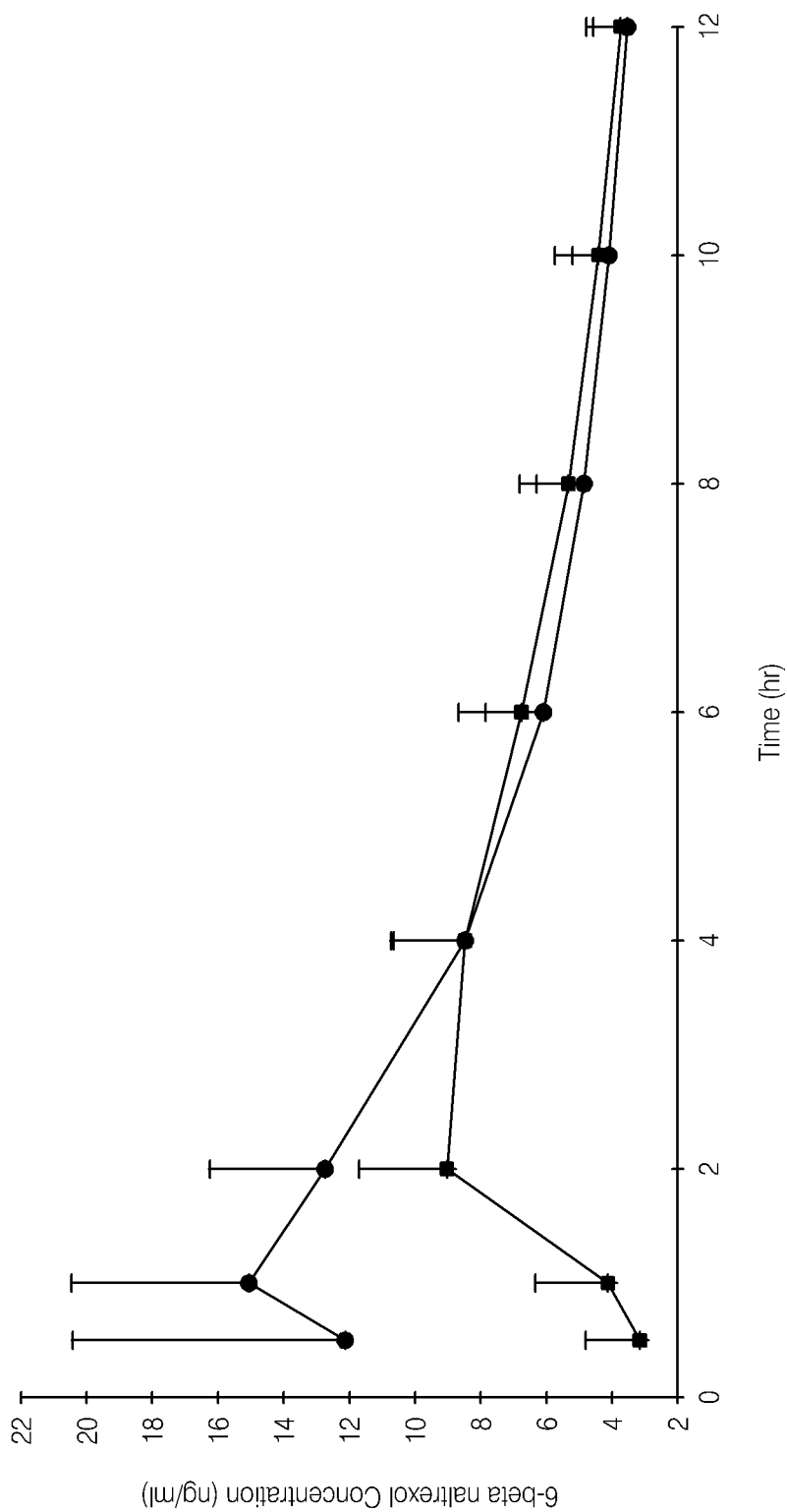
FIG. 12 shows the average plasma concentrations of 6-beta naltrexol in subjects receiving naltrexone IR in combination with bupropion SR (●) or naltrexone SR in combination with bupropion SR (■).

Table 15 and FIG. 12 compare average 6-beta naltrexol plasma concentrations in subjects receiving treatments of naltrexone IR and bupropion SR (squares) to that in subjects receiving treatments of naltrexone SR and bupropion SR (circles). The plasma concentrations associated with the SR/SR treatment are lower during the first few hours following administration than those associated with the IR/SR treatment. As reported in Table 16, the SR/SR treatment is associated with a lower $C_{max}$ but a similar AUC as compared to the IR/SR treatment.

TABLE 15

Mean plasma concentrations of 6-beta naltrexol in subjects receiving naltrexone IR in combination with bupropion SR (IR/SR) or naltrexone SR in combination with bupropion SR (SR/SR).

| Treatment | Time (hr) | N | Mean (ng/ml) | SD (ng/ml) | CV % |
|---|---|---|---|---|---|
| IR/SR | 0 | 0 | NC | NC | NC |
|  | 0.5 | 27 | 12.14 | 8.3 | 68.33 |
|  | 1 | 30 | 15.05 | 5.44 | 36.15 |
|  | 2 | 30 | 12.74 | 3.55 | 27.87 |
|  | 4 | 30 | 8.45 | 2.3 | 27.21 |
|  | 6 | 30 | 6.11 | 1.8 | 29.43 |
|  | 8 | 30 | 4.86 | 1.45 | 29.81 |
|  | 10 | 30 | 4.09 | 1.17 | 28.59 |
|  | 12 | 30 | 3.56 | 1.05 | 29.54 |
|  | 168 | 27 | 10.59 | 4.13 | 39.03 |
|  | 336 | 27 | 15.66 | 6.71 | 42.88 |
| SR/SR | 0 | 0 | NC | NC | NC |
|  | 1 | 13 | 3.2 | 1.65 | 51.66 |
|  | 1 | 27 | 4.16 | 2.21 | 52.99 |
|  | 2 | 29 | 9.05 | 2.69 | 29.74 |
|  | 4 | 29 | 8.51 | 2.17 | 25.47 |
|  | 6 | 29 | 6.77 | 1.95 | 28.84 |
|  | 8 | 29 | 5.37 | 1.49 | 27.82 |
|  | 10 | 29 | 4.43 | 1.35 | 30.53 |
|  | 12 | 29 | 3.72 | 1.09 | 29.37 |
|  | 168 | 28 | 11.21 | 4.54 | 40.52 |
|  | 336 | 26 | 18.67 | 10.74 | 57.52 |

TABLE 16

Mean pharmacokinetic parameters for 6-beta naltrexol on Day 1 in subjects receiving naltrexone IR in combination with bupropion SR (IR/SR) or naltrexone SR in combination with bupropion SR (SR/SR).

| | IR/SR | | | | SR/SR | | | |
|---|---|---|---|---|---|---|---|---|
| Parameter | N | Mean | SD | CV % | N | Mean | SD | CV % |
| Tmax | 30 | 1.117 | 0.536 | 48 | 29 | 2.621 | 0.942 | 35.9 |
| Cmax | 30 | 16.731 | 6.391 | 38.2 | 29 | 9.686 | 2.323 | 24 |
| AUClast | 30 | 86.658 | 23.457 | 27.1 | 29 | 71.623 | 16.711 | 23.3 |
| AUCINF_obs | 30 | 118.445 | 35.191 | 29.7 | 29 | 115.771 | 45.398 | 39.2 |
| HL_Lambda_z | 30 | 5.989 | 1.796 | 30 | 29 | 7.838 | 4.58 | 58.4 |

Figure 13:
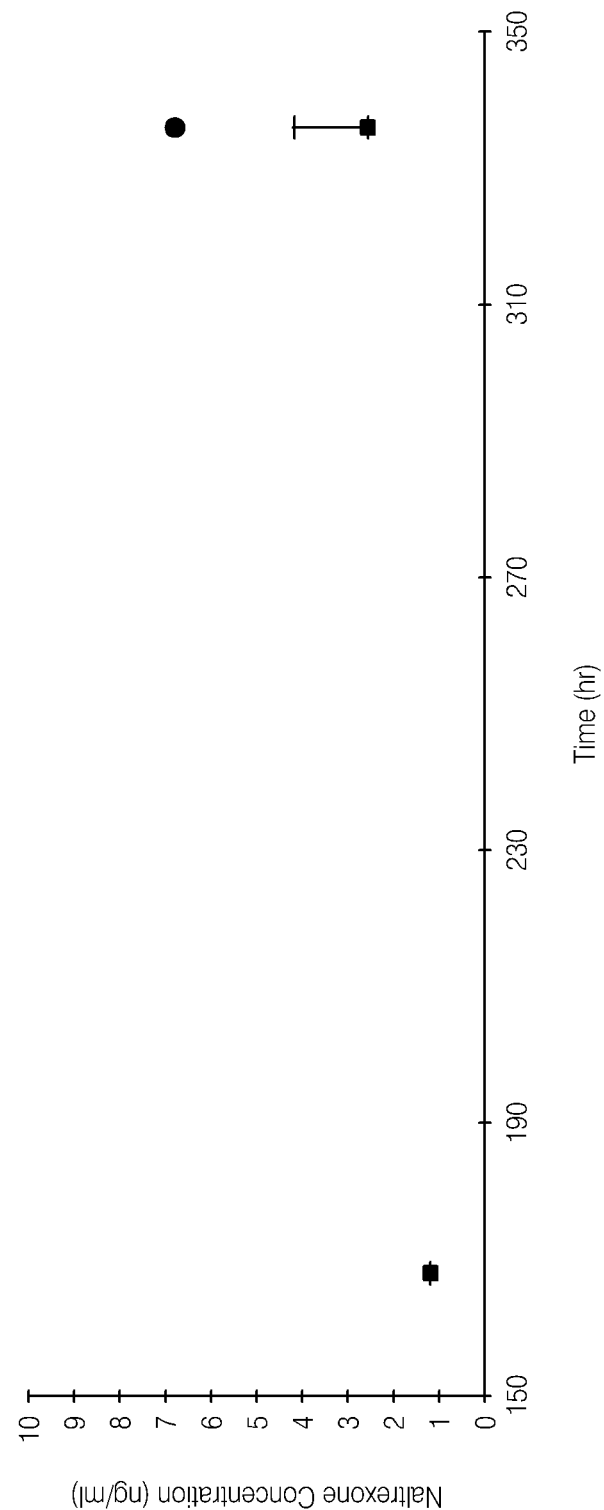
FIG. 13 shows the average trough plasma concentrations of naltrexone in subjects receiving naltrexone IR in combination with bupropion SR (●) or naltrexone SR in combination with bupropion SR (■).
Figure 14:
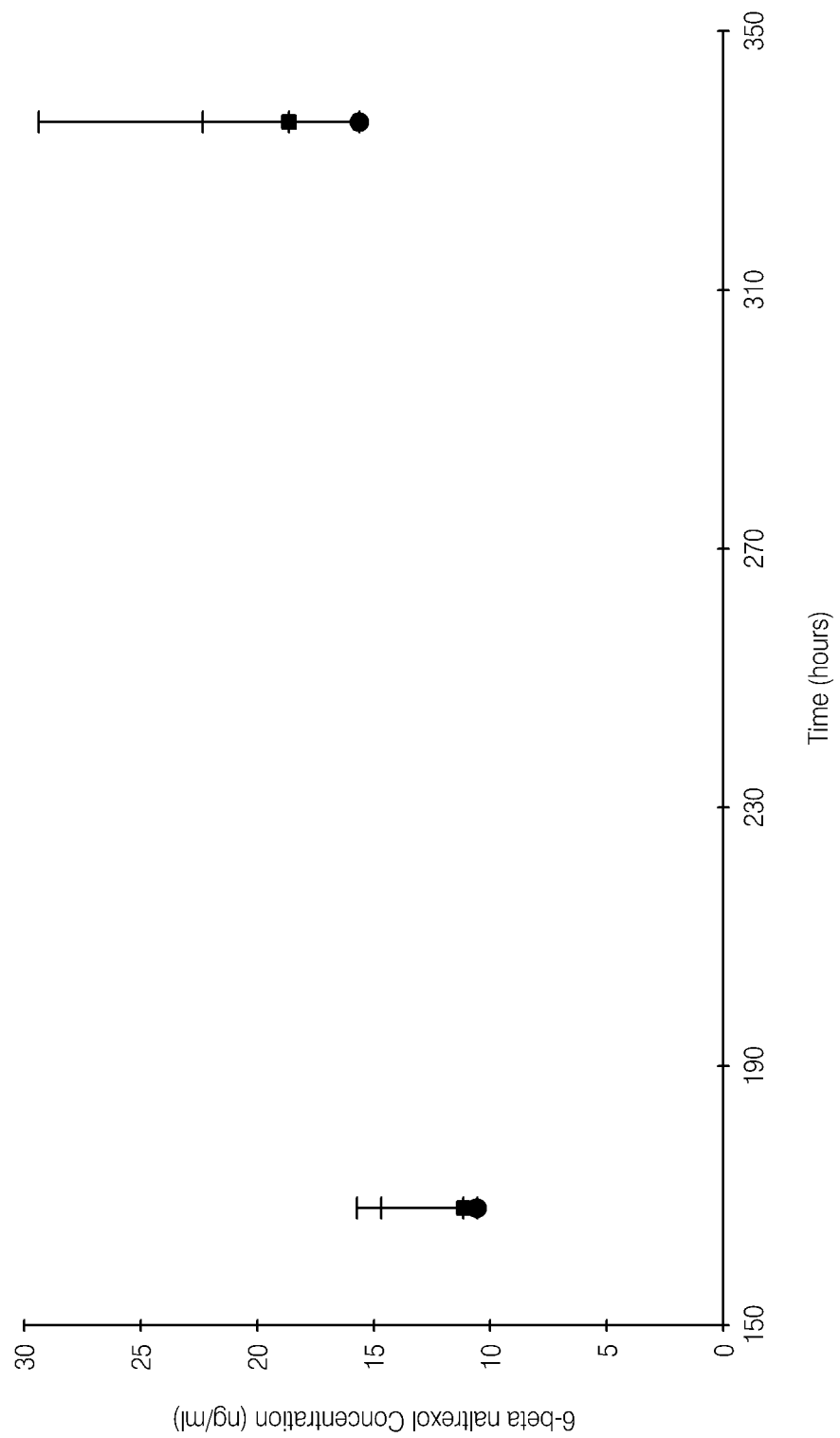
FIG. 14 shows the average trough plasma concentrations of 6-beta naltrexol in subjects receiving naltrexone IR in combination with bupropion SR (●) or naltrexone SR in combination with bupropion SR (■).

FIGS. 13 and 14 compare the trough plasma concentrations of naltrexone and 6-beta naltrexol, respectively, in subjects receiving treatments of naltrexone IR and bupropion SR (circles) to that in subjects receiving treatments of naltrexone SR and bupropion SR (squares). For naltrexone, the trough levels on Day 8 and Day 15 are primarily BLLOQ, with the exception of 1 subject in the IR group, and 2 subjects in the SR group. For 6-beta naltrexol, the trough levels of Day 8 and Day 15 are similar between treatment groups.

Figure 15:
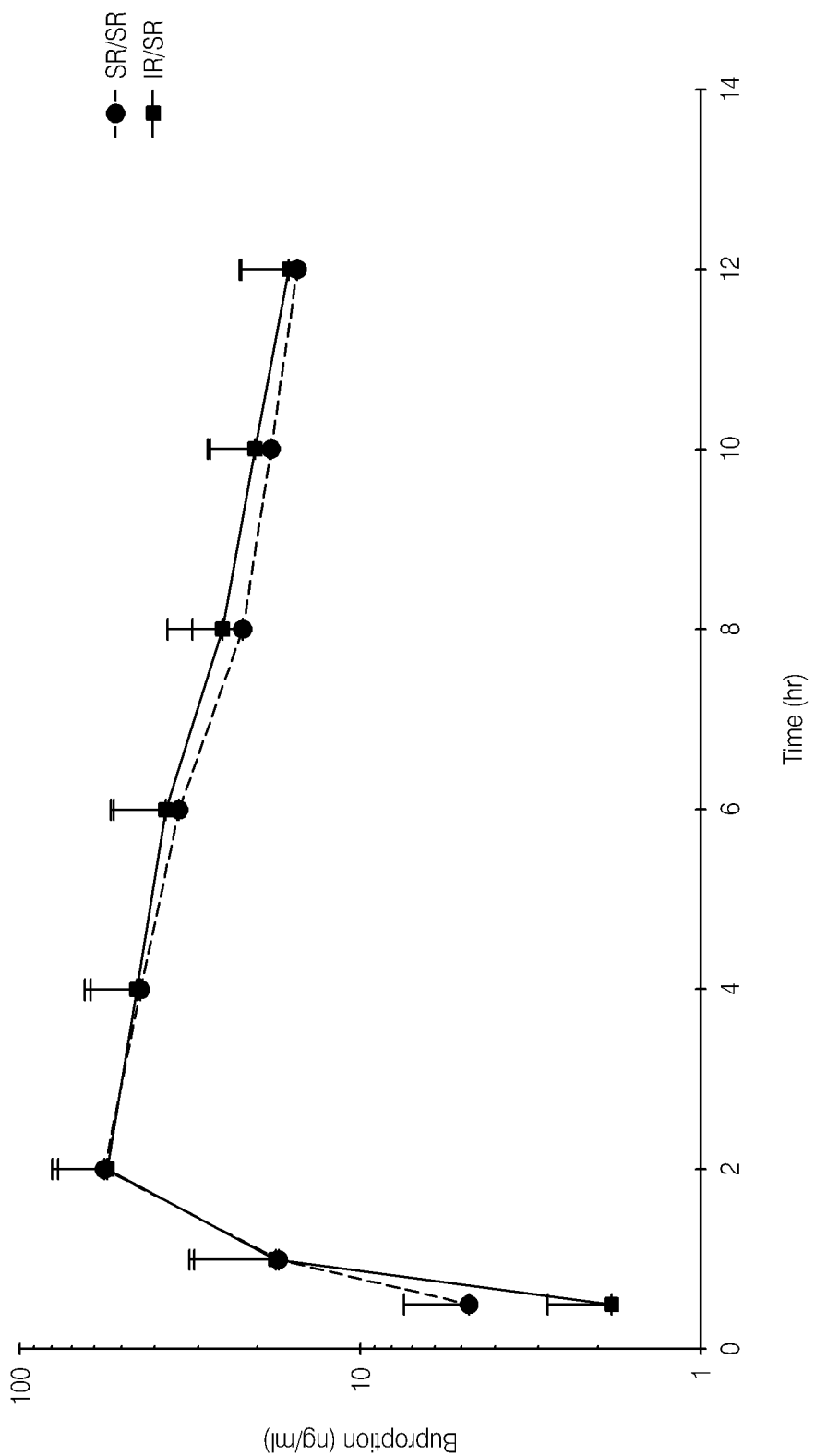
FIG. 15 shows the average plasma concentrations of bupropion in subjects receiving bupropion SR in combination with naltrexone SR (●) or in combination with naltrexone IR (■).

Table 17 and FIG. 15 compare average bupropion plasma concentrations in subjects receiving treatments of naltrexone IR and bupropion SR (squares) to that in subjects receiving treatments of naltrexone SR and bupropion SR (circles). The plasma concentration profiles are similar across the treatment conditions.

TABLE 17

Mean Buproprion Plasma Concentrations in subjects receiving bupropion SR in combination with naltrexone IR (IR/SR) or in combination with naltrexone SR (SR/SR).

| Treatment | Time (hr) | N | Mean (ng/ml) | SD (ng/ml) | CV % |
|---|---|---|---|---|---|
| IR/SR | 0 | 0 | NC | NC | NC |
| | 0.5 | 6 | 1.83 | 0.99 | 54.07 |
| | 1 | 23 | 17.62 | 13.86 | 78.66 |
| | 2 | 23 | 54.23 | 21.64 | 39.9 |
| | 4 | 23 | 44.83 | 16.83 | 37.53 |
| | 6 | 23 | 37.1 | 16.32 | 43.99 |
| | 8 | 23 | 25.29 | 11.28 | 44.59 |
| | 10 | 23 | 20.1 | 7.89 | 39.27 |
| | 12 | 23 | 16.03 | 6.44 | 40.19 |
| SR/SR | 0 | 0 | NC | NC | NC |
| | 0.5 | 7 | 4.77 | 2.62 | 54.95 |
| | 1 | 20 | 17.14 | 13.41 | 78.23 |
| | 2 | 20 | 55.04 | 24.96 | 45.35 |
| | 4 | 20 | 43.96 | 20.3 | 46.18 |
| | 6 | 20 | 33.77 | 18.18 | 53.83 |
| | 8 | 20 | 21.98 | 8.77 | 39.89 |
| | 10 | 20 | 18.13 | 9.43 | 52.02 |
| | 12 | 20 | 15.22 | 7.03 | 46.18 |

Figure 16:
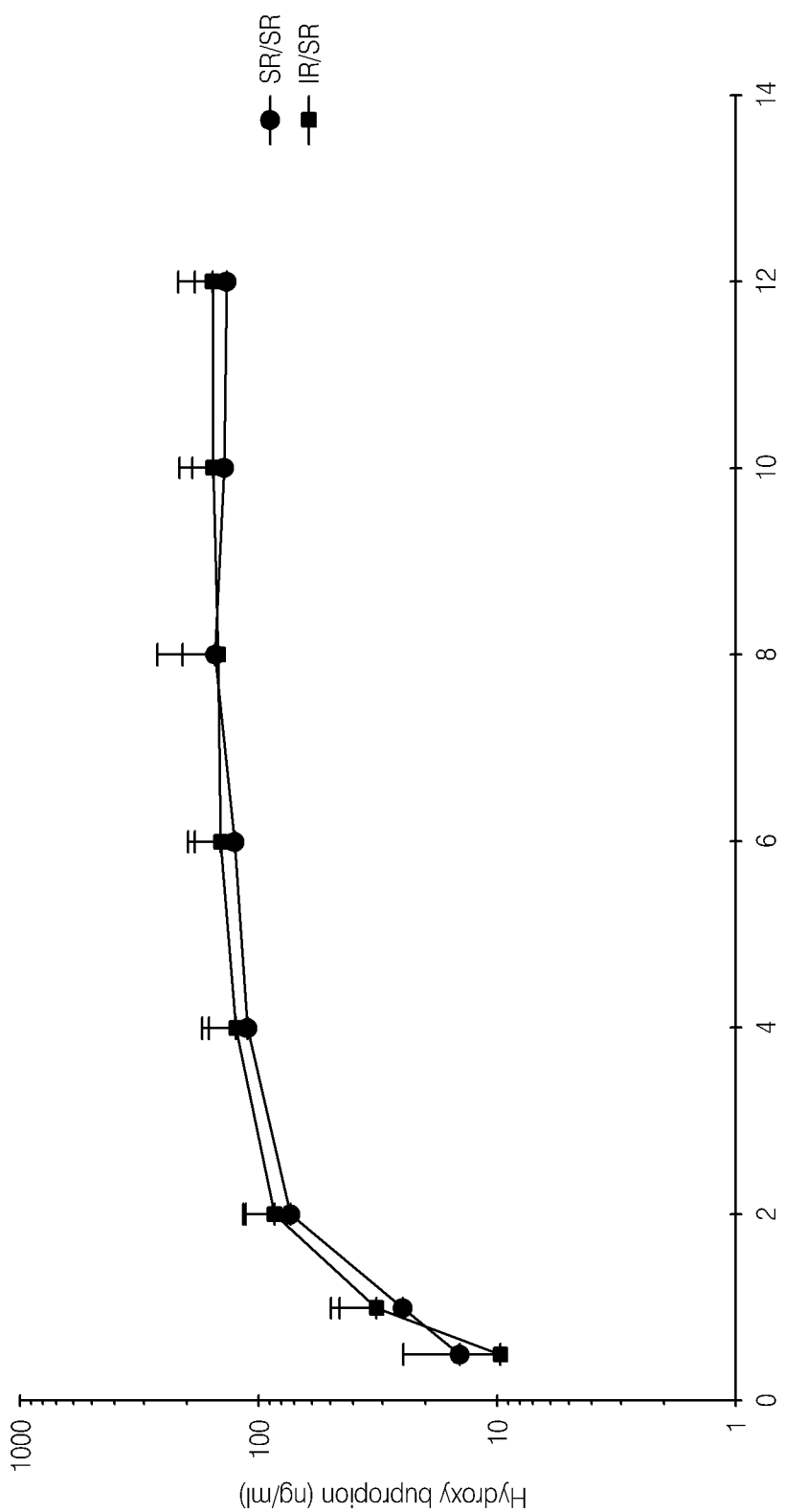
FIG. 16 shows the average plasma concentrations of the bupropion metabolite hydroxybupropion in subjects receiving bupropion SR in combination with naltrexone SR (●) or in combination with naltrexone IR (■).
Figure 17:
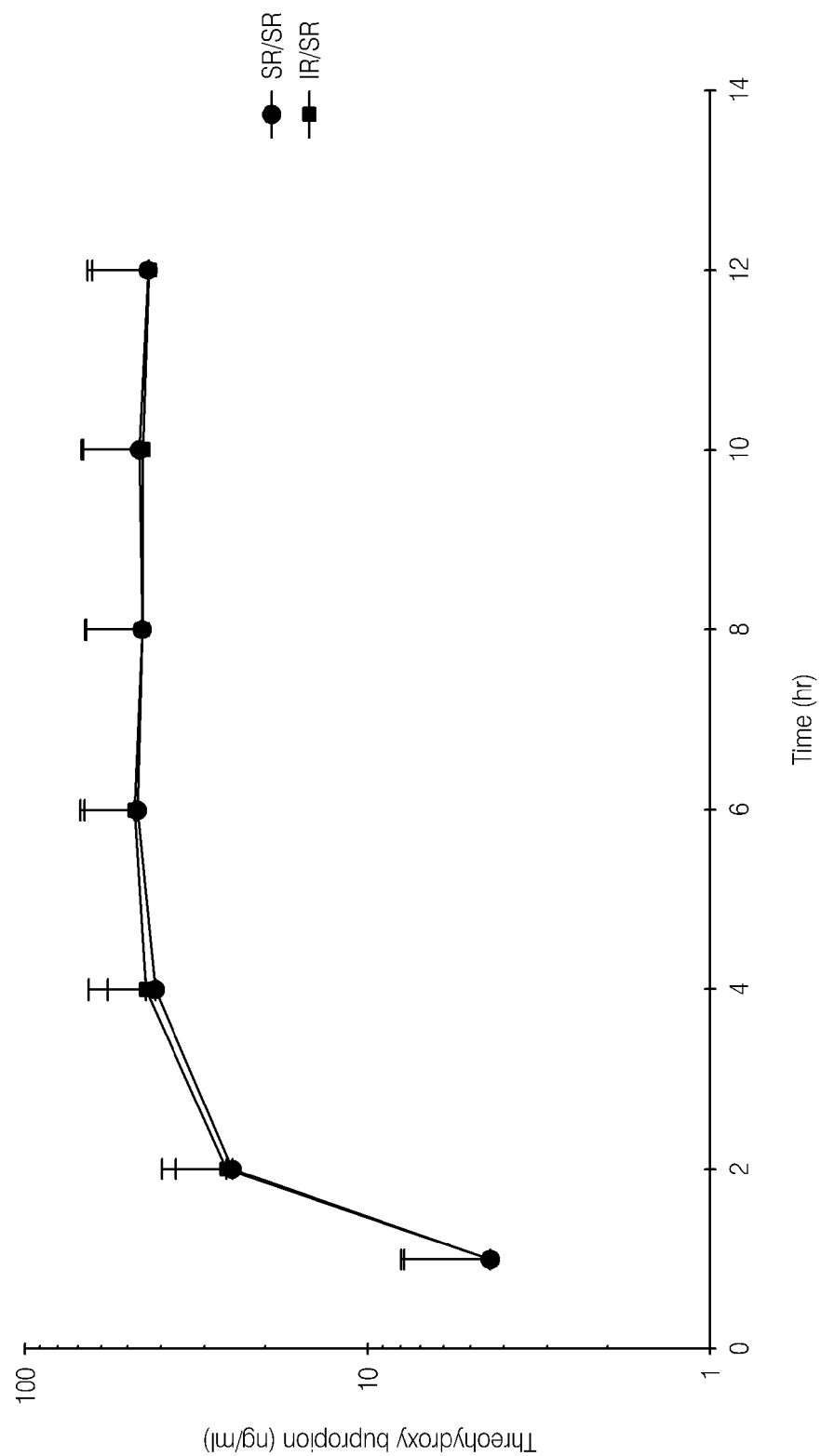
FIG. 17 shows the average plasma concentrations of the bupropion metabolite threohydroxybupropion in subjects receiving bupropion SR in combination with naltrexone SR (●) or in combination with naltrexone IR (■).
Figure 18:
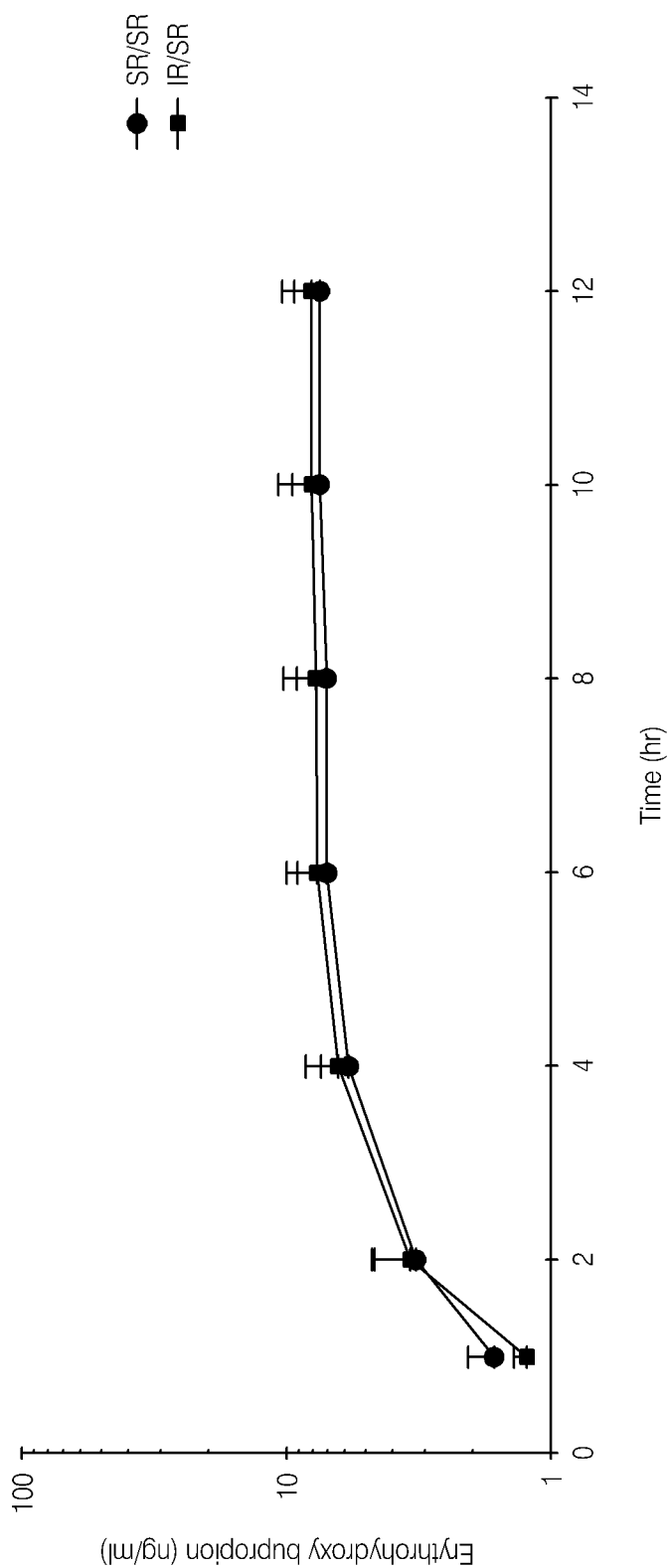
FIG. 18 shows the average plasma concentrations of the bupropion metabolite erythrohydroxybupropion in subjects receiving bupropion SR in combination with naltrexone SR (●) or in combination with naltrexone IR (■).

Tables 18-20 and FIGS. 16-18 compare average plasma concentrations for the bupropion metabolites of hydroxybupropion, threohydroxybupropion and erythrohydroxybupropion in subjects receiving treatments of naltrexone IR and bupropion SR (squares) to that in subjects receiving treatments of naltrexone SR and bupropion SR (circles). The plasma concentration profiles are similar across the treatment conditions.

TABLE 18

Mean plasma concentrations of the bupropion metabolite hydroxybupropion in subjects receiving bupropion SR in combination with naltrexone IR (IR/SR) or in combination with naltrexone SR (SR/SR).

| Treatment | Time (hr) | N | Mean (ng/ml) | SD (ng/ml) | CV % |
|---|---|---|---|---|---|
| IR/SR | 0 | 0 | NC | NC | NC |
| | 0.5 | 7 | 9.72 | 4.43 | 45.59 |
| | 1 | 26 | 32.41 | 17.36 | 53.58 |
| | 2 | 26 | 85.82 | 31.03 | 36.16 |
| | 4 | 27 | 125.34 | 47.16 | 37.63 |
| | 6 | 27 | 142.53 | 56.45 | 39.6 |
| | 8 | 27 | 147.57 | 59.78 | 40.51 |
| | 10 | 27 | 155.42 | 61.9 | 39.82 |
| | 12 | 27 | 157.17 | 62.65 | 39.86 |
| SR/SR | 0 | 0 | NC | NC | NC |
| | 0.5 | 6 | 14.48 | 10.64 | 73.45 |
| | 1 | 24 | 25.07 | 21.07 | 84.02 |
| | 2 | 24 | 74.36 | 39.09 | 52.56 |
| | 4 | 25 | 112.29 | 50.81 | 45.24 |

TABLE 18-continued

Mean plasma concentrations of the bupropion metabolite hydroxybupropion in subjects receiving bupropion SR in combination with naltrexone IR (IR/SR) or in combination with naltrexone SR (SR/SR).

| Treatment | Time (hr) | N | Mean (ng/ml) | SD (ng/ml) | CV % |
|---|---|---|---|---|---|
| | 6 | 25 | 127.44 | 58.1 | 45.59 |
| | 8 | 25 | 150.85 | 114.97 | 76.22 |
| | 10 | 25 | 139.93 | 50.44 | 36.05 |
| | 12 | 25 | 137.81 | 49.48 | 35.9 |

TABLE 19

Mean plasma concentrations of the bupropion metabolite threohydroxybupropion in subjects receiving bupropion SR in combination with naltrexone IR (IR/SR) or in combination with naltrexone SR (SR/SR).

| Treatment | Time (hr) | N | Mean (ng/ml) | SD (ng/ml) | CV % |
|---|---|---|---|---|---|
| IR/SR | 0 | 0 | NC | NC | NC |
| | 0.5 | 0 | NC | NC | NC |
| | 1 | 20 | 4.44 | 3.41 | 76.95 |
| | 2 | 27 | 26.16 | 13.99 | 53.48 |
| | 4 | 27 | 44.57 | 21.2 | 47.57 |
| | 6 | 27 | 48.28 | 21.57 | 44.68 |
| | 8 | 27 | 45.88 | 21.29 | 46.4 |
| | 10 | 27 | 45.39 | 22.2 | 48.92 |
| | 12 | 27 | 43.61 | 22.5 | 51.58 |
| SR/SR | 0 | 0 | NC | NC | NC |
| | 0.5 | 0 | NC | NC | NC |
| | 1 | 15 | 4.39 | 3.62 | 82.52 |
| | 2 | 24 | 25.15 | 11.2 | 44.51 |
| | 4 | 25 | 41.77 | 15.84 | 37.92 |
| | 6 | 25 | 47.17 | 20.4 | 43.24 |
| | 8 | 24 | 45.65 | 20.85 | 45.68 |
| | 10 | 25 | 46.44 | 21.98 | 47.34 |
| | 12 | 25 | 44.08 | 20.09 | 45.57 |

TABLE 20

Mean plasma concentrations of the bupropion metabolite erythrohydroxybupropion in subjects receiving bupropion SR in combination with naltrexone IR (IR/SR) or in combination with naltrexone SR (SR/SR).

| Treatment | Time (hr) | N | Mean (ng/ml) | SD (ng/ml) | CV % |
|---|---|---|---|---|---|
| IR/SR | 0 | 0 | NC | NC | NC |
| | 0.5 | 0 | NC | NC | NC |
| | 1 | 4 | 1.24 | 0.15 | 12.42 |
| | 2 | 26 | 3.5 | 1.3 | 37.26 |
| | 4 | 27 | 6.47 | 2.07 | 32.03 |
| | 6 | 27 | 7.7 | 2.42 | 31.38 |
| | 8 | 27 | 7.77 | 2.56 | 32.94 |
| | 10 | 27 | 8.04 | 2.71 | 33.67 |
| | 12 | 27 | 8.05 | 2.4 | 29.8 |
| SR/SR | 0 | 0 | NC | NC | NC |
| | 0.5 | 0 | NC | NC | NC |
| | 1 | 2 | 1.64 | 0.43 | 26.22 |
| | 2 | 24 | 3.26 | 1.5 | 46.01 |
| | 4 | 25 | 5.87 | 1.65 | 28.14 |
| | 6 | 25 | 7.07 | 2.17 | 30.75 |
| | 8 | 24 | 7.18 | 2.06 | 28.63 |
| | 10 | 25 | 7.58 | 2.04 | 26.89 |
| | 12 | 25 | 7.51 | 1.92 | 25.51 |

Table 21 reports the bupropion and bupropion metabolite $AUC_{last}$ and the $C_{max}$ values for the two treatment conditions. These values are similar for both treatments.

TABLE 21

Mean pharmacokinetic parameters for bupropion and metabolites on Day 1 in subjects receiving bupropion SR in combination with naltrexone IR (IR/SR) or in combination with naltrexone SR (SR/SR).

| | IR/SR | | | | SR/SR | | | |
|---|---|---|---|---|---|---|---|---|
| Analyte | N | Mean | SD | CV % | N | Mean | SD | CV % |
| Bupropion | | | | | | | | |
| AUClast | 23 | 367.6 | 122.4 | 33.3 | 20 | 348.7 | 149.1 | 42.8 |
| Cmax | 23 | 58.0 | 19.6 | 33.8 | 20 | 57.5 | 23.7 | 41.2 |
| Hydroxybupropion | | | | | | | | |
| AUClast | 27 | 1452.6 | 556.8 | 38.3 | 25 | 1334.0 | 584.5 | 43.8 |
| Cmax | 27 | 162.3 | 64.4 | 39.7 | 25 | 163.3 | 114.0 | 69.8 |
| Erythrohydroxybupropion | | | | | | | | |
| AUClast | 27 | 74.8 | 22.5 | 30.1 | 25 | 69.6 | 18.5 | 26.7 |
| Cmax | 27 | 8.5 | 2.7 | 31.5 | 25 | 8.0 | 2.1 | 26.6 |
| Threohydroxybupropion | | | | | | | | |
| AUClast | 27 | 456.5 | 209.2 | 45.8 | 25 | 452.0 | 185.0 | 40.9 |
| Cmax | 27 | 51.2 | 23.0 | 44.8 | 25 | 50.7 | 21.7 | 42.8 |

Adverse event listings as well as dosing logs were used for this analysis. Data was entered into spreadsheets, QA'd, and then summarized for frequency of event, % of subjects reporting various events, time to onset from first dose and day in titration schedule. The incidence of adverse effects obtained using the unprompted method of this example is not directly comparable to the incidence obtained using the methods of Example 4.

As shown in Table 22, the percent of subjects reporting any adverse events was 26% and 30% for the SR and IR groups, respectively. The percent of subjects reporting any GI related adverse events was 10% and 16% for the SR and IR groups; similar percentages were observed for subjects reporting any CNS related adverse events. More subjects reported more than one adverse event in the IR group (6/30, 20%), than in the SR group (2/30, 6.6%). Lastly, more subjects reported adverse events that were moderate or greater in severity in the IR group (30.7%) compared with the SR group (16.7%).

TABLE 22

Adverse events associated with IR and SR naltrexone with SR bupropion treatment

| | Group 1 | Group 2 |
|---|---|---|
| % Subjects Reporting Any AEs | 26% | 30% |
| Number of Subjects | 8/30 | 9/30 |
| % Subjects Reporting Any GI related AEs* | 10% | 16% |
| Number of Subjects | 3/30 | 5/30 |
| % Subjects Reporting Any CNS related AEs** | 10% | 16% |
| Number of Subjects | 3/30 | 5/30 |
| % Subjects Reporting More Than 1 AE | 6.6% | 20% |
| Number of Subjects | 2/30 | 6/30 |
| Average Day in Titration Schedule of Onset of AEs | 2 | 4 |
| % AEs Reported as | 16.7% | 30.7% |

TABLE 22-continued

Adverse events associated with IR and SR naltrexone with SR bupropion treatment

| | Group 1 | Group 2 |
|---|---|---|
| Moderate Severity Distribution of Events | 10 events as mild<br>2 events as moderate<br>0 events as severe | 18 events as mild<br>8 events as moderate<br>0 events as severe |

*GI related events defined as any report of: nausea, stomach pain, stomach cramps, loss of appetite, diarrhea, emesis, queasiness, dry heaves, increased bowel movements
**CNS related events defined as any report of: headache, dizziness, drowsiness, lightheadedness, sleepiness, lethargy
*** Subjects reporting >1 type of GI or CNS adverse event were included in each event frequency Thus, the group that received the sustained-release naltrexone with bupropion was less likely to experience adverse events than the group that received the immediate-release naltrexone with bupropion. Additionally, the reported adverse events from the group that received the sustained-release naltrexone with bupropion were less severe than those reported from the immediate-release naltrexone group.

4 subjects withdrew consent from the study; none are listed as having not completed the study due to an adverse event. These subjects are not removed from the calculations presented. Three of the 4 subjects reported an adverse event, but none dropped out on the day the event was reported. Three of the subjects were receiving IR, the fourth was receiving SR.

All events (n=12) in the SR group were reported as mild, with the exception of one instance of euphoria and one instance of stomach cramps (both moderate). Most of the events (n=26) were reported as mild. There were five GI-related (emesis, stomach pain, nausea) and 3 CNS-related events that were described as moderate (headache, fatigue).

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of treating overweight or obesity having reduced adverse effects comprising:
    selecting for treatment a subject in need of a treatment for obesity or overweight; and
    orally administering at least daily about 4 mg to about 32 mg of naltrexone and about 90 mg to about 360 mg of bupropion, or pharmaceutically acceptable salts thereof to said subject, wherein the bupropion or pharmaceutically acceptable salt thereof is administered as a sustained-release formulation, wherein the naltrexone or pharmaceutically acceptable salt thereof is administered as a sustained-release formulation having an in vitro naltrexone dissolution profile in a dissolution test of USP Apparatus 2 Paddle Method at 100 rpm in a dissolution medium of water at 37° C. of:
    a) 67% to 80% of naltrexone released in 1 hour; and
    b) 85% to 96% of naltrexone released in 2 hours;
    whereby at least one adverse effect associated with administration of the same amount of an immediate-release naltrexone formulation and said sustained-release formulation of bupropion or a pharmaceutically acceptable salt thereof is reduced.

2. The method of claim 1, wherein the amount of bupropion or pharmaceutically acceptable salt thereof administered per day is selected from the group consisting of about 90 mg, about 180 mg, about 270 mg, and about 360 mg, and the amount of naltrexone or pharmaceutically acceptable salt thereof administered per day is selected from the group consisting of about 4 mg, about 8 mg, about 12 mg, about 16 mg, about 24 mg and about 36 mg.

3. The method of claim 1, wherein said sustained-release naltrexone or pharmaceutically acceptable salt thereof and said sustained-release bupropion or pharmaceutically acceptable salt thereof are administered in a single oral unit dosage form.

4. The method of claim 1, wherein said sustained-release formulation of naltrexone provides an in vivo plasma concentration profile of:
    a) a naltrexone $C_{max}$ that is less than 80% of the naltrexone $C_{max}$ of an equal amount of immediate-release naltrexone hydrochloride; and
    b) a naltrexone $AUC_{last}$ that is between 80% and 125% of the naltrexone $AUC_{last}$ of an equal amount of immediate-release naltrexone hydrochloride.

5. The method of claim 4, wherein said sustained-release naltrexone or a pharmaceutically acceptable salt thereof and said sustained-release bupropion or a pharmaceutically acceptable salt thereof are administered in a single oral unit dosage form.

6. The method of claim 1, wherein said sustained-release formulation of naltrexone further provides an in vivo plasma concentration profile of:
    c) a 6-beta naltrexol $C_{max}$ that is less than 80% of the 6-beta naltrexol $C_{max}$ of an equal amount of immediate-release naltrexone hydrochloride; and
    d) a 6-beta naltrexol $AUC_{last}$ that is between 80% and 125% of the 6-beta naltrexol $AUC_{last}$ of an equal amount of immediate-release naltrexone hydrochloride.

7. The method of claim 1, wherein said sustained-release formulation of naltrexone or a pharmaceutically acceptable salt thereof provides an in vitro release rate of naltrexone in the dissolution test of at least 99% in 8 hours.

8. The method of claim 1, wherein said sustained-release formulation of naltrexone or a pharmaceutically acceptable salt thereof is administered twice daily.

9. The method of claim 1, wherein said sustained-release formulation of naltrexone or pharmaceutically acceptable salt thereof provides an in vitro release rate of naltrexone in the dissolution test of less than 98% in 4 hours.

10. The method of claim 9, wherein said sustained-release formulation of naltrexone or a pharmaceutically acceptable salt thereof provides an in vitro release rate of naltrexone in the dissolution test of at least 99% in 8 hours.

11. The method of claim 1, wherein said at least one adverse effect comprises at least one adverse effect selected from the group consisting of nausea, headache and dizziness.

12. The method of claim 11, wherein said at least one adverse effect comprises nausea.

13. The method of claim 1, wherein said sustained-release naltrexone or pharmaceutically acceptable salt thereof and said sustained-release bupropion or pharmaceutically acceptable salt thereof are administered in separate oral dosage forms.

14. A method of treating overweight or obesity having reduced adverse effects comprising orally administering daily about 32 mg of naltrexone and about 360 mg of bupropion, or pharmaceutically acceptable salts thereof, to a person in need thereof, wherein the bupropion or pharmaceutically acceptable salt thereof is administered as a sustained-release formulation, wherein the naltrexone or pharmaceutically acceptable salt thereof is administered as a sustained-release formulation, and wherein said sustained-release formulation of naltrexone has an in vitro naltrexone dissolution profile in a dissolution test of USP Apparatus 2 Paddle Method at 100 rpm in a dissolution medium of water at 37° C. of:
    a) 67% to 80% of naltrexone released in 1 hour; and
    b) 85% to 96% of naltrexone released in 2 hours; and
    c) at least 99% of naltrexone released in 8 hours;
    wherein about 16 mg of said sustained-release formulation of naltrexone or a pharmaceutically acceptable salt thereof is administered twice daily, and about 180 mg of said sustained-release formulation of bupropion or a pharmaceutically acceptable salt thereof is administered twice daily.

15. The method of claim 14, wherein said sustained-release naltrexone or pharmaceutically acceptable salt thereof and said sustained-release bupropion or pharmaceutically acceptable salt thereof are administered in a single oral unit dosage form.

16. The method of claim 14, wherein said at least one adverse effect comprises at least one adverse effect selected from the group consisting of nausea, headache and dizziness.

17. The method of claim 16, wherein said at least one adverse effect comprises nausea.

* * * * *